United States Patent
Kaplan et al.

(10) Patent No.: US 9,925,301 B2
(45) Date of Patent: Mar. 27, 2018

(54) METHODS OF PRODUCING AND USING SILK MICROFIBERS

(71) Applicant: TRUSTEES OF TUFTS COLLEGE, Medford, MA (US)

(72) Inventors: David L. Kaplan, Concord, MA (US); Biman B. Mandal, Kolkata (IN)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 14/390,362

(22) PCT Filed: Apr. 5, 2013

(86) PCT No.: PCT/US2013/035389
§ 371 (c)(1),
(2) Date: Oct. 2, 2014

(87) PCT Pub. No.: WO2013/152265
PCT Pub. Date: Oct. 10, 2013

(65) Prior Publication Data
US 2015/0165092 A1 Jun. 18, 2015

Related U.S. Application Data

(60) Provisional application No. 61/621,209, filed on Apr. 6, 2012.

(51) Int. Cl.
| | |
|---|---|
| *A61L 27/36* | (2006.01) |
| *A61L 27/56* | (2006.01) |
| *D02J 1/00* | (2006.01) |
| *D01C 3/00* | (2006.01) |
| *D04H 1/4266* | (2012.01) |
| *D06M 11/36* | (2006.01) |
| *A61L 27/54* | (2006.01) |
| *A61L 27/58* | (2006.01) |
| *C08J 5/04* | (2006.01) |
| *A61L 27/38* | (2006.01) |
| *C08K 7/02* | (2006.01) |
| *A61L 27/48* | (2006.01) |
| *D06M 101/12* | (2006.01) |

(52) U.S. Cl.
CPC ......... *A61L 27/3604* (2013.01); *A61L 27/365* (2013.01); *A61L 27/3687* (2013.01); *A61L 27/3821* (2013.01); *A61L 27/3834* (2013.01); *A61L 27/48* (2013.01); *A61L 27/54* (2013.01); *A61L 27/56* (2013.01); *A61L 27/58* (2013.01); *C08J 5/045* (2013.01); *C08K 7/02* (2013.01); *D01C 3/00* (2013.01); *D02J 1/00* (2013.01); *D04H 1/4266* (2013.01); *D06M 11/36* (2013.01); *A61L 2400/06* (2013.01); *A61L 2430/02* (2013.01); *D06M 2101/12* (2013.01)

(58) Field of Classification Search
None
See application file for complete search history.

(56) References Cited

U.S. PATENT DOCUMENTS

| | | | | |
|---|---|---|---|---|
| 5,853,764 A | * | 12/1998 | Tsubouchi | C08J 3/12 424/499 |
| 6,719,985 B1 | * | 4/2004 | Tsubouchi | A61K 8/64 424/400 |
| 7,674,882 B2 | | 3/2010 | Kaplan et al. | |
| 7,751,985 B2 | * | 7/2010 | Li | A61K 8/64 530/353 |
| 7,842,780 B2 | | 11/2010 | Kaplan et al. | |
| 8,071,722 B2 | | 12/2011 | Kaplan et al. | |
| 8,187,616 B2 | | 5/2012 | Wang et al. | |
| 8,361,617 B2 | | 1/2013 | Kaplan et al. | |
| 8,986,380 B2 | | 3/2015 | Kaplan et al. | |
| 2007/0212730 A1 | | 9/2007 | Vepari et al. | |
| 2010/0028451 A1 | | 2/2010 | Kaplan et al. | |
| 2010/0178304 A1 | | 7/2010 | Wang et al. | |
| 2011/0171239 A1 | | 7/2011 | Kaplan et al. | |
| 2012/0070427 A1 | | 3/2012 | Kaplan et al. | |
| 2012/0123519 A1 | | 5/2012 | Lovett et al. | |
| 2012/0187591 A1 | | 7/2012 | Wang et al. | |
| 2012/0244143 A1 | | 9/2012 | Lo et al. | |
| 2014/0222152 A1 | | 8/2014 | Kaplan et al. | |

FOREIGN PATENT DOCUMENTS

| | | | | |
|---|---|---|---|---|
| EP | 1938774 A1 | * | 7/2008 | ........... A61K 38/012 |
| JP | 2000-170029 A | | 6/2000 | |
| JP | 2007-224005 A | | 9/2007 | |

(Continued)

OTHER PUBLICATIONS

Walters, Roy H., and O. A. Hougen. "Silk degumming I. Degradation of silk sericin by alkalies." Textile Research Journal 5.2 (1934): 92-104.*
Jiang, Ping, et al. "Tensile behavior and morphology of differently degummed silkworm (Bombyx mori) cocoon silk fibres." Materials letters 60.7 (2006): 919-925.*
PubChem entry for Sodium Carbonate, National Center for Biotechnology Information. PubChem Compound Database; CID=10340, https://pubchem.ncbi.nlm.nih.gov/compound/10340 (accessed Aug. 5, 2016).*
U.S. Appl. No. 61/613,185, filed Mar. 20, 2012, Kaplan et al.
U.S. Appl. No. 61/696,405, filed Sep. 4, 2012, Kaplan et al.
U.S. Appl. No. 61/791,501, filed Mar. 15, 2013, Kaplan.

(Continued)

*Primary Examiner* — Robert J Yamasaki
(74) *Attorney, Agent, or Firm* — Choate, Hall & Stewart LLP

(57) ABSTRACT

Provided herein relates to methods for preparing micron range silk fibers (or silk microfibers) and compositions comprising a micron range silk fiber (or a silk microfiber). The micron range silk fibers (or silk microfibers) can be used in various applications ranging from fillers in cosmetics to reinforcement materials to design high strength composites, e.g., reinforced scaffolds. In some embodiments, the silk microfiber-reinforced scaffolds can be used for bone graft applications because of their high compressive strength.

14 Claims, 22 Drawing Sheets

(56) References Cited

FOREIGN PATENT DOCUMENTS

| WO | WO-02/29141 A1 | 4/2002 |
|---|---|---|
| WO | WO-03/043486 A2 | 5/2003 |
| WO | WO-2004/000255 A1 | 12/2003 |
| WO | WO-2004/000915 A2 | 12/2003 |
| WO | WO-2004/080346 A2 | 9/2004 |
| WO | WO-2005/012606 A2 | 2/2005 |
| WO | WO-2007/016524 A2 | 2/2007 |
| WO | WO-2008/106485 A2 | 9/2008 |
| WO | WO-2008/150861 A1 | 12/2008 |
| WO | WO-2009/023615 A1 | 2/2009 |
| WO | WO-2009/100280 A2 | 8/2009 |
| WO | WO-2009/126689 A2 | 10/2009 |
| WO | WO-2011/005381 A2 | 1/2011 |
| WO | WO-2011/008842 A2 | 1/2011 |
| WO | WO-2012/054582 A2 | 4/2012 |
| WO | WO-2012/145594 A2 | 10/2012 |
| WO | WO-2012/145652 A1 | 10/2012 |
| WO | WO-2013/044067 A1 | 3/2013 |
| WO | WO-2013/070907 A1 | 5/2013 |
| WO | WO-2013/071107 A1 | 5/2013 |
| WO | WO-2013/071123 A1 | 5/2013 |
| WO | WO-2013/119551 A1 | 8/2013 |
| WO | WO-2013/130937 A1 | 9/2013 |
| WO | WO-2013/142119 A1 | 9/2013 |
| WO | WO-2013/152265 A1 | 10/2013 |

OTHER PUBLICATIONS

Acharya, C. et al., Performance evaluation of a silk protein-based matrix for the enzymatic conversion of tyrosine to L-DOPA, 3:226-233 (2008).
Bayraktar, O. et al., Silk fibroin as a novel coating material for controlled release of theophylline, European Journal of Pharmaceutics and Biopharmaceutics, 60:373-381 (2005).
Demura, M. and Asakura, T., Immobilization of glucose oxidase with Bombyx mori silk fibroin by only stretching treatment and its application to glucose sensor, Biotechnol. Bioeng., 33(5):598-603 (1989).
Gil, E.S. et al., Mechanical improvements to reinforced porous silk scaffolds, J. Biomed. Mater. Res. A., 99(1):16-28 (2011).
Hofmann, S., et al., Silk fibroin as an organic polymer for controlled drug delivery, Journal of Controlled Release, 111:219-227 (2006).
Hu, X. et al., Regulation of silk material structure by temperature-controlled water vapor annealing, Biomacromolecules, 12(5):1686-1696 (2011).
International Search Report for PCT/US2013/035389, 5 pages (dated Aug. 23, 2013).
Jin, I.J. et al., Water-Stable Silk Films with Reduced Beta-Sheet Content, Adv. Funct. Mater., 15:1241-1247 (2005).
Li, M. et al., Study on Porous Silk Fibroin Materials. II. Preparation and Characteristics of Spongy Porous Silk Fibroin Materials, Journal of Applied Polymer Science, 79:2192-2199 (2001).
Liao, J. et al., Modulation of osteogenic properties of biodegradable polymer/extracellular matrix scaffolds generated with a flow perfusion bioreactor, Acta Biomater., 6(7):2386-93 (2010).
Lovett, M. et al., Gel spinning of silk tubes for tissue engineering, Biomaterials, 29(35):4650-4657 (2008).
Lu, S. et al., Stabilization of Enzymes in Silk Films, Biomacromolecules, 10:1032-1042 (2009).
Min, S. et al., Preparation and Characterization of Crosslinked Porous Silk Fibroin Gel, Sen'I Gakkaishi, 54(2):85-92 (1997).
Miyairi, S. and Sugiura, M., Properties of β-Glucosidase Immobilized in Sericin Membrane, Journal of Fermentation Technology, 56(4):303-308 (1978).
Nazarov, R. et al., Porous 3-D scaffolds from regenerated silk fibroin, Biomacromolecules, 5(3):718-26 (2004).
Rajkhowa, R. et al., Reinforcing silk scaffolds with silk particles, Macromol. Biosci., 10(6):599-611 (2010).
Rockwood, D. et al., Ingrowth of human mesenchymal stem cells into porous silk particle reinforced silk composite scaffolds: An in vitro study, Acta Biomater, 7(1):144-151 (2011).
Sikavitsas, V.I. et al., Formation of three-dimensional cell/polymer constructs for bone tissue engineering in a spinner flask and a rotating wall vessel bioreactor, J. Biomed. Mater. Res., 62:136-148 (2002).
Written Opinion for PCT/US2013/035389, 6 pages (dated Aug. 23, 2013).
Altman, G.H. et al., Silk matrix for tissue engineered anterior cruciate ligaments, Biomaterials, 23:4131-4141 (2002).
Discher, D.E. et al., Tissue cells feel and respond to the stiffness of their substrate, Science, 310: 1139-1143 (2005).
Engler, A.J. et al., Matrix elasticity directs stem cell lineage specification, Cell, 126:677-689 (2006).
Kim, H.J. et al., Bone regeneration on macroporous aqueous-derived silk 3-D scaffolds, Macromol. Biosci., 7:643-655 (2007).
Mandal, B.B. et al., Multilayered silk scaffolds for meniscus tissue engineering, Biomaterials, 32:639-651 (2011).
Meinel, L. et al., The inflammatory responses to silk films in vitro and in vivo, Biomaterials, 26:147-155 (2005).
Santin, M. et al., In vitro evaluation of the inflammatory potential of the silk fibroin, J. Biomed. Mater. Res. 46:382-389 (1999).
Vepari, C. and Kaplan, D.L., Silk as a biomaterial, Prog. Polym. Sci., 32:991-1007 (2007).
Wang, Y. et al., In vivo degradation of three-dimensional silk fibroin scaffolds, Biomaterials, 29:3415-3428 (2008).
Alford, A.I. and Hankenson, K.D., Matricellular proteins: extracellular modulators of bone development, remodeling, and regeneration, Bone, 38:749-757 (2006).
Balloni, S. et al., Effects of titanium surface roughness on mesenchymal stem cell commitment and differentiation signaling, Int. J. Oral. Maxillofac. Implants, 24:627-635 (2009).
Banse, X., et al. Inhomogeneity of human vertebral cancellous bone: Systematic density and structure patterns inside the vertebral body, Bone, 28:563-571 (2001).
Chiellini, F. et al. Micro/nanostructured polymeric systems for biomedical and pharmaceutical applications, Nanomed, 3:367-93 (2008).
Coleman, D. and Howitt, F.O., Studies on Silk Proteins. I. The Properties and Constitution of Fibroin. The Conversion of Fibroin into a Water-Soluble Form and Its Bearing on the Phenomenon of Denaturation, PRS London, Series A, Math Phy. Sci. 90:145-169 (1947).
Dawson, J.I. et al., Development of specific collagen scaffolds to support the osteogenic and chondrogenic differentiation of human bone marrow stromal cells, Biomaterials, 29(21):3105-16 (2008).
Del Gaudio, C. et al., Assessment of electrospun PCL scaffold fortissue engineering, Int. J. Artif. Organs, 29:537-537 (2006).
Desai, A.V. and Haque, M.A., Mechanics ofthe interface for carbon nanotube-polymer composites,Thin-Walled Struct, 43: 1787-1803 (2005).
Drosse, I. et al., Tissue engineering for bone defect healing: an update on a multi-component approach, Injury, 39 Suppl 2:S9-20 (2008).
Ganss, B., et al. Bone sialogrotein, Crit. Rev. Oral Biol. Med. 10:79-98 (1999).
Giachelli, CM. and Steitz, S., Osteopontin: a versatile regulator of inflammation and biomineralization, Matrix Biol. 19:615-622 (2000).
Hodgskinson, R. and Currey, J.D., Young modulus. Density and material properties in cancellous bone over a large density range, J. Mater. Sci. Mater. M., 3:377-381 (1992).
Hu, X., et al., The influence of elasticity and surface roughness on myogenic and osteogenic-differentiation of cells on silk elastin biomaterials, Biomaterials, 32:8979-8989 (2011).
Hutmacher, D.W. et al., Mechanical properties and cell cultural response of polycaprolactone scaffolds designed and fabricated via fused deposition modeling, J. Biomed. Mater. Res., 55(2):203-16 (2001).
Izquierdo, R. et al., Biodegradable PCL scaffolds with an interconnected spherical pore network fortissue engineering, J. Biomed. Mater. Res. A., 85(1):25-35 (2008).

(56) References Cited

OTHER PUBLICATIONS

Jutras, I. and Desjardins, M., Phagocytosis: at the crossroads of innate and adaptive immunity, Ann. rev. cell dev. biol., 21:511-527 (2005).
Kane, R.J. and Roeder, R.K, Effects of hydroxyapatite reinforcement on the architecture and mechanical properties of freeze-dried collagen scaffolds, J. Mech. Behav. Biomed. Mater, (doi:10.1016/j.jmbbm.2011.09.010) (2011).
Kang, Y. et al., Enhanced mechanical performance and biological evaluation of a PLGA coated b-TCP composite scaffold for load-bearing applications, Eur. Poly J., 47: 1569-1577 (2011).
Kasugai, S. et al., Temporal studies on the tissue compartmentalization of bone sialoprotein (BSP), Osteopontin (OPN), and SPARC protein during bone formation in vitro, J. Cell Physiol., 152:467-477 (1992).
Khan, Y. et al., Tissue engineering of bone: material and matrix considerations, J. Bone Joint Surg. Am., 90 Suppl 1:36-42 (2008).
Khan, Y.M. et al., Novel polymer-synthesized ceramic composite-based system for bone repair: an in vitro evaluation, J. Biomed. Mater. Res. A., 69(4):728-37 (2004).
Kim, H.J. et al., Influence of macroporous protein scaffolds on bone tissue engineering from bone marrow stem cells, Biomaterials, 26:4442-4452 (2005).
Langer, R. and Vacant!, JP., Tissue engineering, Science, 260(5110):920-6 (1993).
Lau, K.T. et al., a critical review on nanotube and nanotube/nanoclay related polymer composite materials, Compos Part B Eng. 37:425-436 (2006).
Leong, K.F. et al., Solid freeform fabrication of three-dimensional scaffolds for engineering replacement tissues and organs, Biomaterials, 24(13):2363-78 (2003).
Li, Z. et al. Chitosan-alginate hybrid scaffolds for bone tissue engineering, Biomaterials, 26:3919-3928 (2005).
Mandal, B.B. and Kundu, S.C., Cell proliferation and migration in 3D silk fibroin scaffolds, Biomaterials, 30:2956-2965 (2009c).
Mandal, B.B. and Kundu, S.C., Non-mulberry silk gland fibroin 3D scaffold for enhanced differentiation of human mesenchymal stem cells into osteocytes, Acta. Biomaterialia, 5:2579-2590 (2009a).
Mandal, B.B. and Kundu, S.C., Osteogenic and adipogenic differentiation of rat bone marrow cells on mulberry and non-mulberry silk gland fibroin 3D scaffolds, Biomaterials, 30:5019-5030 (2009b).
Marquis, M.E. et al., Bone cells-biomaterials interactions, Front. Biosci. (Landmark Ed), 14:1023-67 (2009).
Muller, R., et al. Morphometric analysis of human bone biopsies: A quantitative structural comparison of histological sections and micro-computed tomography, Bone, 23:59-66 (1998).
Nihouannen, D. L. et al., Micro-architecture of calcium phosphate granules and fibrin glue composites for bone tissue engineering, Biomaterials, 27(13):2716-22 (2006).
Nukavarapu, S.P. et al., Polyphosphazene/nano-hydroxyapatite composite microsphere scaffolds for bone tissue engineering, Biomacromolecules, 9: 1818-1825 (2008).
Ochi, K. et al., Use of isolated mature osteoblasts in abundance acts as desired-shaped bone regeneration in combination with a modified poly-DL-lactic-co-glycolic acid (PLGA)-collagen sponge, J. Cell Physiol., 194(1):45-53 (2003).
Oliveira, J.M. et al., Novel hydroxyapatite/chitosan bilayered scaffold for osteochondral tissue-engineering applications: Scaffold design and its performance when seeded with goat bone marrow stromal cells, Biomaterials, 27(36):6123-37 (2006).
Park, S.H. et al., Relationship between degradability of silk scaffolds and osteogenesis, Biomaterials, 31 :6162-6172 (2010).
Pek, Y.S. et al., Porous collagen-apatite nanocomposite foams as bone regeneration scaffolds, Biomaterials, 29(32):4300-5 (2008).
Pra, D. I., et al., De novo engineering of reticular connective tissue in vivo by silk fibroin nonwoven materials, Biomaterials, 26:1987-1999 (2005).
Rajkhowa, R. et al., Fabrication of ultra fine powder from eri silk through attritor and jet milling, Powder Technology, 191: 155-163 (2009).
Rajkhowa, R. et al., Ultra fine silk powder preparation through rotary and ball milling, Power Technology, 185:87-95 (2008).
Ramakrishna, S. et al., Biomedical applications of polymer-composite materials: a review, Compos Sci. Technol., 61:1189-1224 (2001).
Salgado, A.J. et al., Bone tissue engineering: state of the art and future trends, Macromol. Biosci., 4(8):743-65 (2004).
Shao, Z.Z. and Vollrath, F., The surprising strength of silkworm silk, Nature, 418:741 (2002).
Thein-Han, W.W. et al., Superior in vitro biological response and mechanical properties of an implantable nanostructured biomaterial: Nanohydroxyapatite-silicone rubber composite, Acta Biomater., 5(7):2668-79 (2009).
Vitale-Brovarone, C. et al., High strength bioactive glass-ceramic scaffolds for bone regeneration, J. Mater. Sci. Mater. Med., 20(2):643-53 (2009).
Wang, M., Developing bioactive composite materials for tissue replacement, Biomaterials, 24:2133-2151 (2003).
Wang, Y. et al., Stem cell-based tissue engineering with silk biomaterials, Biomaterials, 27:6064-6082 (2006).
Wang, Y. et al., Improved mechanical properties of hydroxyapatite/poly(caprolactone) scaffolds by surface modification of hydroxyapatite, App. Surf Sci., 256:6107-6112 (2010).
Wei, G. and Ma, P.X., Structure and properties of nano-hydroxyapatite/polymer composite scaffolds for bone tissue engineering, Biomaterials, 25(19):4749-57 (2004).
Xiao, Y. et al., Tissue engineering for bone regeneration using differentiated alveolar bone cells in collagen scaffolds, Tissue Eng., 9(6):1167-77 (2003).
Xu, C. et al., Biocompatibility and osteogenesis of biomimetic Bioglass-Collagen-Phosphatidylserine composite scaffolds for bone tissue engineering, Biomaterials, 32:1051-1058 (2011).
Yang, X.B. et al., Biomimetic collagen scaffolds for human bone cell growth and differentiation, Tissue Eng., 10(7-8):1148-59 (2004).
Yaszemski, M.J. et al., Evolution of bone transplantation: molecular, cellular and tissue strategies to engineer human bone, Biomaterials, 17(2):175-85 (1996).
Zhang, K. et al., Porous polymer/bioactive glass composites for soft-to-hard tissue interfaces, J. Biomed. Mater. Res., 61(4):551-63 (2002).
Zhang, Y. et al., The osteogenic properties of CaP/silk composite scaffolds, Biomaterials, 31(10):2848-56 (2010).
Zhou, Y. et al., Combined marrow stromal cell-sheet techniques and high-strength biodegradable composite scaffolds for engineered functional bone grafts, Biomaterials, 28(5):814-24 (2007).

* cited by examiner

METHODS OF PRODUCING AND USING SILK MICROFIBERS

CROSS REFERENCE TO RELATED APPLICATIONS

This application claims the benefit under 35 U.S.C. § 119(e) of U.S. Provisional Application No. 61/621,209 filed Apr. 6, 2012, the content of which is incorporated herein by reference in its entirety.

GOVERNMENT SUPPORT

This invention was made with government support under grants EB002520 and EB003210 awarded by the National Institutes of Health and FA9550-10-1-0172 awarded by the United States Air Force, respectively. The government has certain rights in the invention.

TECHNICAL FIELD

Provided herein relates to silk microfibers and methods of making and using the same. In some embodiments, silk microfibers can be used as reinforcing fillers in a scaffold for tissue engineering. In some embodiments, reinforced scaffolds comprising silk microfibers have a compressive modulus sufficient for applications in bone repair.

BACKGROUND

Bone defects, both large and small, from non-unions or trauma patients, pose a significant challenge and often require surgical intervention. See, e.g., Drosse I. (2008) "Tissue engineering for bone defect healing: an update on a multi-component approach." Injury 39:S9-20). In the U.S. alone, 1.3 million people undergo bone graft surgeries each year with skeletal defects either from accidents or disease (Langer R and Vacanti J P (1993) "Tissue Engineering". Science 260:920-926). However, current treatments mostly rely on autografts or allografts but have associated risks, with autografts needing an additional surgical site and limited in supply, while allografts have potential risks of disease transmission and long term complications. See, e.g., Marquis M E et al. (2009) "Bone cells biomaterials interactions." Front Biosci 14:1023-1067; Khan Y et al. (2008) "Tissue engineering of bone: material and matrix considerations." J Bone Joint Surg Am 90:36-42.

Tissue engineering represents a promising solution towards repair and replacement of these diseased and damaged bone tissues with engineered grafts. Towards this goal, a wide range of natural and synthetic biodegradable polymers has been evaluated, including hyaluronic acid, chitosan, poly(L-lactide-co-glycolide) (PLGA), polycaprolactone (PCL), polymethylmethacrylate (PMMA) as well as several ceramic materials such as calcium phosphate, calcium sulfate and bioactive glass. See, e.g., Dawson J I, et al. (2008) "Development of specific collagen scaffolds to support the osteogenic and chondrogenic differentiation of human bone marrow stromal cells." Biomaterials 29:3105-3116; Pek Y S et al. (2008) "Porous collagen apatite nanocomposite foams as bone regeneration scaffolds." Biomaterials 29:4300-4305; Oliveira J M et al. (2006) "Novel hydroxyapatite/chitosan bilayered scaffold for osteochondral tissue engineering applications: Scaffold design and its performance when seeded with goat bone marrow stromal cells." Biomaterials 27:6123-6137; Le Nihouannen D. et al. (2006) "Micro-architecture of calcium phosphate granules and fibrin glue composites for bone tissue engineering." Biomaterials 27:2716-2722; Sikavitsas V I et al. (2002) "Formation of three-dimensional cell/polymer constructs for bone tissue engineering in a spinner flask and a rotating wall vessel bioreactor." J Biomed Mater Res 62:136-148; Ochi K, et al., (2003) "Use of isolated mature osteoblasts in abundance acts as desired-shaped bone regeneration in combination with a modified poly-DL-lactic-co-glycolic acid (PLGA)-collagen sponge." J Cell Physiol 194:45-53; Zhang K et al. (2002) "Porous polymer/bioactive glass composites for soft to hard tissue interfaces." J Biomed Mater Res 61:551-563; Hutmacher D W et al. (2001) "Mechanical properties and cell cultural response of polycaprolactone scaffolds designed and fabricated via fused deposition modeling." J Biomed Mater Res 55:203-216. Each of these materials presents limitations in achieving the requirements for bone repair scaffolds mentioned earlier. For example, PCL is biocompatible, resorbable and slowly degradable; however its use is limited due to its failure to promote osteogenesis without premineralization. See, e.g., Del Gaudio C. et al. (2006) "Assessment of electrospun PCL scaffold for tissue engineering." Int J Artif Organs 29:537-537; Izquierdo R. et al. (2008) "Biodegradable PCL scaffolds with an interconnected spherical pore network for tissue engineering." J Biomed Mater Res A 8:25-35; Liao J. et al. (2010) "Modulation of osteogenic properties of biodegradable polymer/extracellular matrix scaffolds generated with a flow perfusion bioreactor." Acta Biomater 6:2386-2393. Similarly, collagen and/or collagen-based scaffold have a lower compressive modulus of 0.034 MPa, failing to reach 10-50 MPa of native cancellous bone. See, e.g., Dawson J I. et al. (2008) Biomaterials 29:3105-3116; Xiao Y. et al. (2003) "Tissue engineering for bone regeneration using differentiated alveolar bone cells in collagen scaffolds." Tissue Eng 9:1167-1177; Yang X B B. et al. (2004) "Biomimetic collagen scaffolds for human bone cell growth and differentiation." Tissue Eng 10:1148-1159; Hodgskinson R and Currey J D (1992) "Young modulus. Density and material properties in cancellous bone over a large density range." J Mater Sci Mater M 3:377-381; Yaszemski M J. et al. (1996) "Evolution of bone transplantation: Molecular, cellular and tissue strategies to engineer human bone." Biomaterials 17:175-185.

To improve on the mechanical properties and osteoinductive potential of bone scaffold materials, the use of composites has been explored. The use of ceramic materials such as tri-calcium phosphates, hydroxyapatite (HAP), or bioactive glass as inclusions in polymer matrices is often used to enhance mechanics. See, e.g., Zhang K. et al. (2002) J Biomed Mater Res 61:551-563; Khan Y M. et al. (2004) "Novel polymer-synthesized ceramic composite-based system for bone repair: an in vitro evaluation." J Biomed Mater Res A 69:728-737; Thein-Han W W. et al. (2009) "Superior in vitro biological response and mechanical properties of an implantable nanostructured biomaterial: nano hydroxyapatite-silicone rubber composite. "Acta Biomater 5:2668-2679; Wei G B and Ma P X (2004) "Structure and properties of nano-hydroxyapatite/polymer composite scaffolds for bone tissue engineering." Biomaterials 25:4749-4757; Zhang Y. et al. (2010) "The osteogenic properties of CaP/silk composite scaffolds." Biomaterials 31:2848-2856. The addition of PLGA microspheres with calcium phosphate followed by sintering yielded highly interconnected structures with mechanics similar to trabecular bone in the dry state (Khan Y M. et al. (2004) J Biomed Mater Res A 69:728-737). In another report, silicone rubber with dispersion of nano-hydroxyapatite (nHAP) had improved surface properties for pre-osteoblasts when compared to pure silicone rubber, resulting in enhanced cell attachment, viability and proliferation (Thein-Han W W. et al. (2009) Acta Biomater 5:2668-2679).

However, many challenges remain to satisfy an optimally functional bone regeneration scaffold system (Salgado A J. et al. (2004) "Bone tissue engineering: State of the art and future trends." Macromol Biosci 4:743-765). In particular, a need for polymer materials to meet the high compressive properties of load-bearing bone is an important prerequisite to function in vivo. See, e.g., Gil E S. et al. (2011) "Mechanical improvements to reinforced porous silk scaffolds." J Biomed Mater Res Part A 99:16-28; Rockwood D N. et al. (2011) "Ingrowth of human mesenchymal stem cells into porous silk particle reinforced silk composite scaffolds: An in vitro study." Acta Biomaterialia 7:144-151; Zhou Y F, et al. (2007) Combined marrow stromal cell-sheet techniques and high strength biodegradable composite scaffolds for engineered functional bone grafts. Biomaterials 28:814-824; Leong K F. et al. (2003) "Solid freeform fabrication of three-dimensional scaffolds for engineering replacement tissues and organs." Biomaterials 24:2363-2378; Vitale-Brovarone C. et al. (2009) "High strength bioactive glass-ceramic scaffolds for bone regeneration." J Mater Sci Mater M 20:643-653. Thus, there is still a need for development of engineered grafts with a compressive strength comparable to a load-bearing bone, which can be used for bone repair.

SUMMARY

While tissue engineering represents a promising solution toward repair and/or replacement of a diseased and/or damaged bone tissue with an engineered graft, most of natural and synthetic biodegradable polymers present limitations in achieving the requirements for bone repair scaffolds. In particular, one of the biggest challenges is the need for polymeric biomaterials to meet the high compressive properties of bone, a prerequisite to function in vivo. To this end, inventors inter alia enhanced the compressive properties of scaffolds, e.g., silk scaffolds, by incorporating silk microfiber reinforcements of various lengths in different amounts. A novel silk hydrolysis method using an alkaline solution was also developed to fabricate these silk microfibers, e.g., as fillers within a silk-based matrix for reinforcement. Further, the inventors have surprisingly discovered, in some embodiments, that silk microfiber-reinforced scaffolds are much stronger than silk particle-reinforced scaffolds that were previously reported in Rajkhowa et al., 2010 Macromol Biosci., 10: 599-611; and Gil et al., 2011 J Biomed Mater Res A, 99: 16-28). This indicates that shapes (e.g., particle vs. fiber) and/or size of the reinforcing fillers have unexpectedly different effects on the mechanical property of the bulk matrix. Accordingly, embodiments of various aspects described herein relates to novel methods of making silk microfibers and applications of these silk microfibers, e.g., as reinforcing fillers in materials where high mechanical strength such as compressive properties is desirable.

One aspect provided herein relates to methods of producing a silk microfiber of a desired length. The method comprises contacting a native silk fiber (e.g., a degummed silk fiber) with an alkaline solution. In some embodiments, the contact of a native silk fiber (e.g., a degummed silk fiber) with an alkaline solution comprises immersing the native silk fiber (e.g., a degummed silk fiber) into an alkaline solution.

In some embodiments, the native silk fiber (e.g., a degummed silk fiber) can be contacted with an alkaline solution under a condition such that the native silk fiber (e.g., a degummed silk fiber) becomes hydrolyzed into a plurality of silk microfibers, thereby producing a silk microfiber. The length of the silk microfibers can range from about 1 μm to about 4 mm. In some embodiments, the length of the silk microfibers ranges from about 10 μm to about 1000 μm.

Use of alkaline hydrolysis to generate silk microfibers from native silk fibers is novel in that the size of the microfibers can be modulated and controlled using a faster and cost-effective method as compared to expensive and time-consuming conventional ball-and-jet milling methods. For example, the desired microfiber size/length can be adjusted, in part, by controlling the concentration and/or strength of the alkaline solution, the duration of hydrolysis, hydrolysis temperature, or any combinations thereof. For example, where the alkaline solution comprises a strong basic solution, the concentration of the alkaline solution, the duration and/or temperature of the hydrolysis can be adjusted accordingly to produce silk microfiber(s) of a desired length Examples of a strong basic solution include, without limitations, sodium hydroxide, potassium hydroxide, lithium hydroxide, rubidium hydroxide, cesium hydroxide, calcium hydroxide, strontium hydroxide, barium hydroxide, or any combinations thereof. In one embodiment, the alkaline solution comprises sodium hydroxide.

The alkaline solution for use in hydrolysis of a native silk fiber (e.g., a degummed silk fiber) can be in any concentration. In some embodiments, the alkaline solution can have a concentration of about 0.1 M to about 30 M. In some embodiments, the alkaline solution can be a concentrated alkaline solution, e.g., at a concentration of at least about 1 M or higher.

The hydrolysis of a native silk fiber (e.g., a degummed silk fiber) into a plurality of silk microfibers can be performed at any temperature. Generally, higher temperatures increase the hydrolysis rate, while lower temperatures decrease the hydrolysis rate. In some embodiments, the hydrolysis temperature can range from about 4° C. to about 100° C. In some embodiments, the hydrolysis temperature can range from about room temperature to about 100° C.

Depending on the hydrolysis condition (e.g., hydrolysis temperature, and/or concentration and/or pH of the alkaline solution) and/or desired microfiber length, the contact of the native silk fiber (e.g., a degummed silk fiber) with the alkaline solution can be maintained for any period of time ranging from seconds to minutes to hours. In some embodiments, the duration of hydrolysis can range from about 5 seconds to about 5 hours. In some embodiments, the duration of hydrolysis can range from about 5 seconds to about 500 seconds. For example, the hydrolysis time can be shortened when the native silk fiber (e.g., a degummed silk fiber) is hydrolyzed in a higher concentration and/or higher pH of the alkaline solution, and/or at an elevated hydrolysis temperature.

After contact with an alkaline solution, in some embodiments, the method can further comprise neutralizing the mixture comprising the native silk fiber (e.g., a degummed silk fiber) and the alkaline solution. In some embodiments, the hydrolysis reaction of a native silk fiber (e.g., a degummed silk fiber) in an alkaline solution can be stopped by neutralizing the mixture.

In some embodiments, the method can further comprise annealing the silk microfibers. For example, the silk microfibers can be annealed by a process comprising lyophilization, gas-drying, solvent immersion, water annealing, water vapor annealing, heat annealing, shear stress, ultrasound (e.g., by sonication), pH reduction (e.g., pH titration and/or exposing a silk microfiber to an electric field), or any combination thereof.

In some embodiments, the method can further comprise separating a subset of the silk microfibers of the desired length from the plurality of silk microfibers. By way of example only, a subset of the silk microfibers of the desired length can be separated from the plurality of silk microfibers by sieving and/or filtering.

Another aspect provided herein relates to a silk microfiber produced by one or more embodiments of the silk microfiber production method described herein. The length of the silk microfibers produced by the method described herein can range from about 1 μm to about 4 mm. In some embodiments, the length of the silk microfibers ranges from about 10 μm to about 1000 μm. Depending on natures and/or requirements of applications, the silk microfiber can be adapted to be degradable or non-degradable.

A composition comprising at least one embodiment of a silk microfiber described herein is also provided. In some embodiments, a composition can comprise a plurality of (e.g., at least 2 or more) silk microfibers described herein.

The composition can be formulated in any form to suit the need of an application. By way of example only, the composition can be used to form a construction material, a cosmetic formulation, a consumer product, a medical device or component, a coating, a filler, or a tissue engineering or reconstruction scaffold. In some embodiments, the composition can be formulated as an injectable composition. In some embodiments, the composition can be in the form of a film, a sheet, a gel, a mesh, a mat, a non-woven mat, a fabric, a scaffold, a tube, a slab or block, a particle, a fiber, a 3-dimensional construct, an implant, a high-density material, a porous material, a reinforced material, a non-porous material, a machinable material, a magnetic responsive material, a microneedle, or any combinations thereof.

In some embodiments, the composition can further comprise a matrix material. The matrix material can comprise a polymeric and/or a ceramic material. In these embodiments, the silk microfiber(s) can be dispersed in the matrix material. Accordingly, a composite material comprising silk microfibers distributed in a matrix material, e.g., a polymeric material and/or a ceramic material, is also provided herein. In some embodiments, the silk microfibers can a length ranging from about 1 μm to about 4 mm. In some embodiments, the silk microfibers can have a length ranging from about 5 μm to about 1000 μm, or about 10 μm to about 700 μm.

Any natural or synthetic polymeric material can be used as a matrix material in the composite material described herein. The polymeric material can be degradable or non-degradable, e.g., based on the need of a selected application. In some embodiments, the polymeric material can be biocompatible and/or biodegradable. Examples of polymeric materials that can be used in the composite material include, but are not limited to, silk or silk fibroin, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, poly(lactide-co-glycolide) (PLA-PLA-PGA), polymethylmethacrylate, polyanhydride, polyorthoester, polycaprolactone, polyfumarate, chitosan, alginate, and any combinations thereof. In some embodiments, the polymeric material can comprise a silk-based material or a silk fibroin-based material.

In some embodiments, one or more silk microfibers can be additionally or alternatively distributed in a ceramic material, e.g., but not limited to, calcium phosphate, calcium sulfate, hydroxyapatite, bioactive glass, or any combinations thereof.

The silk microfiber(s) can be present in a matrix material (e.g., polymeric material and/or ceramic material) in any amount. In some embodiments, the matrix material (e.g., a polymeric material and/or ceramic material) and silk microfibers can be present in a weight ratio of about 100:1 to about 1:100, or about 1:1 to about 1:20.

In some embodiments, the silk microfibers can be used as reinforcing fillers in a matrix material (e.g., a polymeric material and/or ceramic material), e.g., to enhance the mechanical property (e.g., compressive or load-bearing property) of the bulk matrix material. In some embodiments, the amounts and/or lengths of the silk microfibers can be optimized for generating a composite material with desired mechanical properties. For example, in some embodiments, the composite material can have a compressive modulus of at least about 3 MPa or higher in its hydrated state (including, e.g., at least about 5 MPa, at least about 10 MPa, at least about 15 MPa, at least about 20 MPa, or higher in its hydrated state).

The matrix material (e.g., a polymeric material and/or ceramic material) can be non-porous or porous. In some embodiments where the matrix material is porous, at least a portion of the pores within the matrix material do not have a smooth surface wall.

The composite material comprising silk microfibers distributed in a matrix material can be in any form selected from the group consisting of a film, a sheet, a gel, a mesh, a mat, a non-woven mat, a fabric, a scaffold, a tube, a slab or block, a particle, a fiber, a 3-dimensional construct, an implant, a high-density material, a porous material, a reinforced material, a non-porous material, a machinable material, a magnetic responsive material, a microneedle, and any combinations thereof.

In some embodiments, the matrix material (e.g., a polymeric and/or ceramic material) can comprise an additive. Examples of the additive include, without limitations, cells; biopolymers; plasticizers; nanoparticles (e.g., gold nanoparticles); therapeutic agents; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; enzymes; an extract made from biological materials such as bacteria, plants, fungi, or animal cells; animal tissues; naturally occurring or synthetic compositions; and any combinations thereof.

The composite material can be adapted to a variety of applications ranging from heavy-duty or high-strength construction applications to consumer products or medical applications such as cosmetic or tissue reconstruction applications. For example, the composite material can be adapted to form a construction material, a cosmetic formulation, a consumer product, a medical device or component, a coating, a filler, or a tissue engineering or reconstruction scaffold. In some embodiments, the composite material can be adapted to form a surgical tool for orthopedic applications. In some embodiments, the composite material can be adapted to form a bone scaffold material. In these embodiments, the bone scaffold material can comprise an osteoconductive agent, an osteoinductive agent, an osteogenic agent, or any combination thereof.

The composite material described herein can be adapted to be degradable or non-degradable, e.g., in order to suite the need of an application. By way of example only, in some embodiments, it is desirable to have a non-degradable composite material for use as a building construction material or a permanent implant. In other embodiments, a biodegradable composite material can be desirable in tissue engineering applications, e.g., for tissue repair and/or regeneration.

Not only have the inventors shown that a composite material comprising silk microfibers distributed in a matrix material, e.g., a silk-based material, can provide significant improvement in compressive properties, as compared to other silk-silk composite materials previously described in Rajkhowa et al., 2010 and Gil et al., 2011; or other art-recognized biomaterials intended for bone tissue engineering, e.g., but not limited to, collagen, PCL, PLGA, chitosan, and/or gelatin, but the inventors have also shown that the silk microfiber-silk composite material can promote differentiation of human mesenchymal stem cells toward bone-like cells and further induce tissue ingrowth with vascularization upon implantation in vivo. Accordingly, yet another aspect provided herein relates to a method of repairing or replacing a diseased or damaged bone tissue in a subject, which comprises placing at a target site of the diseased or damaged bone tissue a bone scaffold material comprising silk microfibers distributed in a matrix material (e.g., a polymeric material and/or ceramic material). In some embodiments, the bone scaffold material can comprise silk microfibers distributed in a silk-based material.

In some embodiments, the bone scaffold material can further comprise an osteoconductive agent, an osteoinductive agent, an osteogenic agent, or any combinations thereof.

In some embodiments, the bone scaffold material can further comprise a cell (e.g., a stem cell). In these embodiments, the bone scaffold material described herein can be used as a temporary, biodegradable support conduit for cell(s) to grow (e.g., native cells or exogenously-added cells) and replace with extracellular matrix, thus further improving biochemical properties over time.

BRIEF DESCRIPTION OF THE DRAWINGS

FIG. 1A shows a schematic representation of silk microfiber fabrication process. FIG. 1B is an SEM image showing degummed silk fiber morphology and possible arrangements of crystalline and less crystalline domains. FIG. 1C is a set of SEM images showing hydrolyzed silk microfibers of varied lengths used as fillers for fabricating reinforced scaffolds. Scale bar represents 400 microns.

FIG. 2A is a bar graph with SEM images showing various lengths of silk microfibers obtained after alkali hydrolysis for a different length of time. FIG. 2B is a bar graph showing compressive modulus of silk microfiber reinforced scaffolds of ratios 1:1 and 1:3, before and after cell culture (28 days). Scale bar represents 200 microns. Data represents mean±standard deviation (n=5), where **$p \leq 0.01$ and *$p \leq 0.05$.

FIG. 3A is a bar graph showing alkaline phosphatase (ALP) activity of seeded hMSCs under differentiating conditions on silk microfiber reinforced scaffolds. FIG. 3B is a line graph of cell proliferation showing normalized values of cell growth within silk scaffolds over a period of 4 weeks. Scale bar represents 200 microns. Data represents mean±standard deviation (n=4), where **$p \leq 0.01$ and *$p \leq 0.05$.

FIG. 5A corresponds to expression data of alkaline phosphatase (ALP). FIG. 5B corresponds to expression data of collagen 1a1. FIG. 5C corresponds to expression data of osteopontin (OP). FIG. 5D corresponds to expression data of bone sialoprotein (BSP). Scale bar represents 200 microns. Data represents mean±standard deviation (n=4), where **$p \leq 0.01$ and *$p \leq 0.05$.

DETAILED DESCRIPTION OF THE INVENTION

Figure 1A:
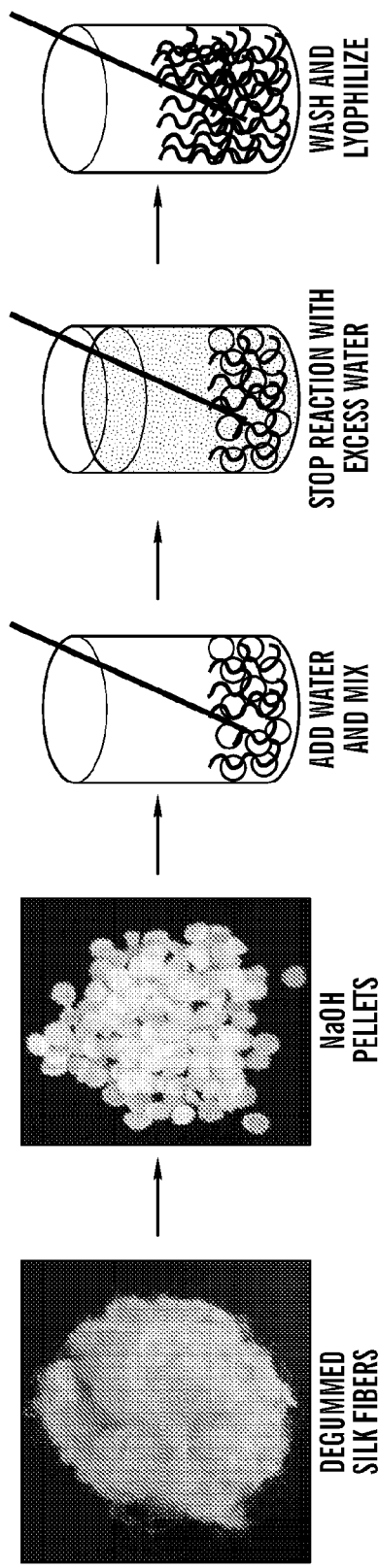
FIGS. 1A-1C show an exemplary method to make micro range silk fibers (or silk microfibers).

Only a handful of existing polymeric biomaterials are utilized for bone tissue regeneration due to their failure to address critical issues, e.g., compressive strength for load bearing bone grafts. Many challenges remain to satisfy an optimally functional bone regeneration scaffold system. In particular, a need for polymer materials to meet the high compressive properties of load-bearing bone is an important prerequisite to function in vivo. Thus, there is still a need for development of engineered grafts with a compressive strength comparable to a load-bearing bone, which can be used for bone repair.

The inventors have demonstrated, in some embodiments, high compressive strength (~13 MPa hydrated state) polymeric bone composite materials based on silk protein-protein interfacial bonding. In some embodiments, micron sized silk fibers (10-600 μm) obtained utilizing alkali hydrolysis were used as reinforcement in a compact fiber composite with tunable compressive strength, surface roughness and porosity based on the fiber length included. A combination of surface roughness, porosity and scaffold stiffness favored cell differentiation, e.g., human bone marrow derived mesenchymal stem cell (hMSC) differentiation towards bone-like tissue in vitro as determined by biochemical and gene expression for bone markers. Further, minimal in vivo immunomodulatory responses indicated compatibility of the fabricated silk-fiber reinforced composite matrices for bone engineering applications. In addition, the inventors have surprisingly discovered, in some embodiments, that silk microfiber-reinforced scaffolds are much stronger than silk particle-reinforced scaffolds that were previously reported in Rajkhowa et al., 2010 Macromol Biosci., 10: 599-611; and Gil et al., 2011 J Biomed Mater Res A, 99: 16-28), indicating that shapes (e.g., particle vs. fiber) and/or size of the reinforcing fillers have unexpectedly different effects on the mechanical property of the bulk matrix. Accordingly, embodiments of various aspects described herein relates to novel methods of making silk microfibers and applications of these silk microfibers, e.g., as reinforcing fillers in materials where high mechanical strength such as compressive properties is desirable, e.g., reinforced scaffolds.

Silk Microfibers and Methods of Producing the Same

One aspect provided herein relates to methods of producing a silk microfiber of a desired length. The method comprises contacting a native silk fiber with an alkaline solution. The native silk fiber can be contacted with an alkaline solution by any means known in the art, e.g., dipping the native silk fiber into an alkaline solution, immersing the native silk fiber into an alkaline solution, spraying an alkaline solution onto the native silk fiber, flowing an alkaline solution over the native silk fiber, soaking or bathing the native silk fiber into an alkaline solution, or any combinations thereof. In some embodiments, the contact of a native silk fiber with an alkaline solution comprises immersing the native silk fiber into an alkaline solution.

As used herein, the phrase "native silk fiber" generally refers to a silk fiber obtained from a silk cocoon. In some embodiments, a native silk fiber encompasses a silk fiber regenerated from silk or silk fibroin, e.g., but not limited to an electrospun silk fiber (e.g., a silk fiber produced by electrospinning a silk fibroin solution). In some embodiments, a native silk fiber encompasses a genetically engineered silk fiber, or a silk fiber regenerated from genetically engineered silk such as from bacteria, yeast, mammalian cells, transgenic animals or transgenic plants. In some embodiments, immunogenic components in the silk (such as sericin) can be removed from a native silk fiber prior to contacting the silk fiber with an alkaline solution. Accordingly, in some embodiments, a native silk fiber, e.g., from a cocoon, can be degummed prior to contacting the native silk fiber with an alkaline solution. Thus, in some embodiments, the method comprises contacting a degummed silk fiber with an alkaline solution.

Native fibers can be degummed to remove or reduce the amount of sericin. For example, silk cocoons (e.g., *Bombyx mori* silkworm silk cocoons) can be degummed by boiling in a solution of about 0.02M $Na_2CO_3$ for at least about 10 minutes, at least about 20 minutes, at least about 30 minutes, at least 60 minutes or longer. The degummed silk fibers are then rinsed (e.g., with water) and dried at ambient conditions (e.g., air dry). Without wishing to be bound by theory, by controlling the degumming time, the solubility and/or degradation property of the silk microfibers produced from the methods described herein can be adjusted accordingly. For example, longer boiling time generally yields silk fibroin of lower molecular weight (MW)/chain length, which can in turn produce a silk fibroin material more susceptible to degradation or soluble (e.g., in an aqueous solution) than the one produced from higher MW silk fibroin.

In accordance with embodiments of various aspects described herein, the alkaline solution is contacted with a native silk fiber (e.g., a degummed silk fiber), which is either in its dried state or in a hydrated state, but the alkaline solution is not contacted with a silk solution formed by pre-dissolving a native silk fiber in a solution.

In some embodiments, the native silk fiber can be contacted with an alkaline solution under a condition such that the native silk fiber becomes hydrolyzed into a plurality of silk microfibers, thereby producing a silk microfiber. As used interchangeably herein, the term "silk microfiber" and "micron range silk fiber" means a silk-based material having an aspect ratio (e.g., a ratio of length to width across its cross-sectional perpendicular to its length) greater than 1:1 or higher, including, e.g., an aspect ratio of at least about 3:2; at least about 2:1, at least about 5:2, at least about 3:1, at least about 4:1, at least about 5:1, at least about 6:1, at least about 7:1, at least about 8:1, at least about 9:1, at least about 10:1 or higher. The length of the silk microfibers can range from about 1 μm to about 4 mm, from about 1 μm to about 3 mm, from about 1 μm to about 2 mm, from about 1 μm to about 1 mm, or from about 1 μm to about 700 μm, or from about 1 μm to about 500 μm. In some embodiments, the length of the silk microfibers can range from about 5 μm to about 2 mm, or from about 5 μm to about 1 mm, or from about 5 μm to about 700 μm. In some embodiments, the length of the silk microfibers can range from about 10 μm to about 1000 μm, or from about 10 μm to about 700 μm, or from about 10 μm to about 500 μm. In some embodiments, a silk microfiber can have a length ranging from about 1 μm to about 50 μm, from about 5 μm to about 30 μm, or from about 10 μm to about 20 μm. In some embodiments, a silk microfiber can have a length ranging from about 50 μm to about 300 μm, from about 100 μm to about 300 μm, or from about 150 μm to about 200 μm. In some embodiments, a silk microfiber can have a length ranging from about 300 μm to about 900 μm, from about 300 μm to about 600 μm, or from about 400 μm to about 500 μm.

In some embodiments, the silk microfiber can have a width (e.g., diameter) of about 1 μm to about 20 μm. In some embodiments, the silk microfiber can have a width (e.g., diameter) substantially same as the width (e.g., diameter) of a native silk fiber from which the silk microfiber is hydrolyzed.

In some embodiments, a native silk fiber can be hydrolyzed into a plurality of silk microfibers of different lengths. For examples, in some embodiments, a native silk fiber can be hydrolyzed into a plurality of silk microfibers ranging from about 1 μm to about 50 μm, from about 5 μm to about 30 μm, or from about 10 μm to about 20 μm. In some embodiments, a native silk fiber can be hydrolyzed into a plurality of silk microfibers ranging from about 50 μm to about 300 μm, from about 100 μm to about 300 μm, or from about 150 μm to about 200 μm. In some embodiments, a native silk fiber can be hydrolyzed into a plurality of silk microfibers ranging from about 300 μm to about 900 μm, from about 300 μm to about 600 μm, or from about 400 μm to about 500 μm.

Figure 2A:
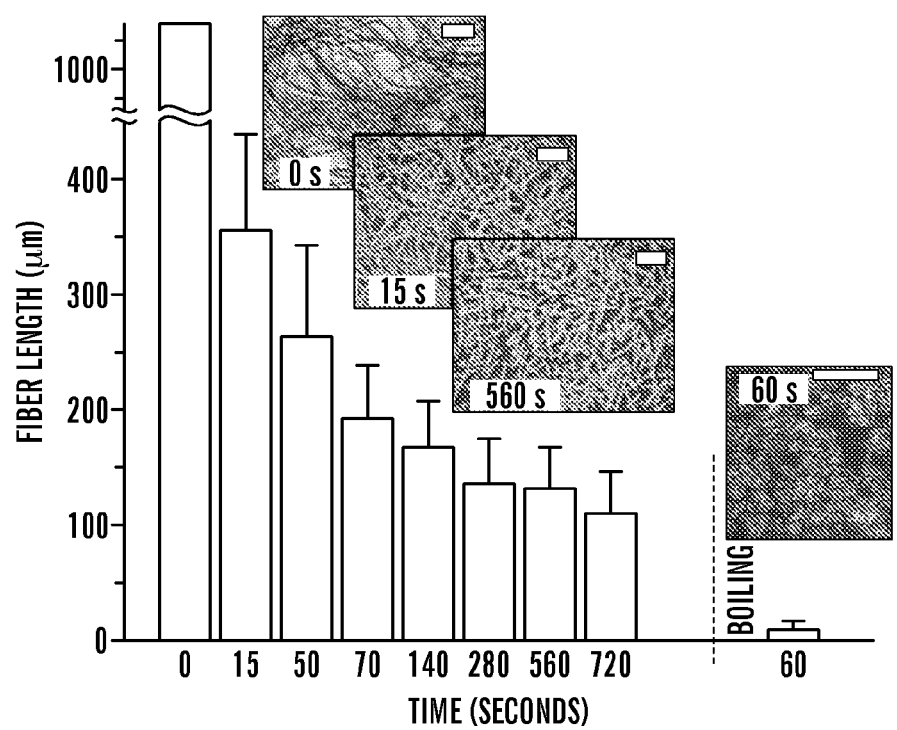
FIGS. 2A-2B show characterization data for various lengths of silk microfibers obtained after alkali hydrolysis and the silk microfiber reinforced scaffolds.

Use of alkaline hydrolysis to generate microfibers from native silk fibers is novel in that the size/length of the microfibers can be modulated and controlled using a faster and cost-effective method as compared to expensive and time-consuming conventional ball-and-jet milling methods. The length of silk microfibers obtained in the alkaline hydrolysis is inversely proportional to time of hydrolysis. Without wishing to be bound by theory, during an alkaline hydrolysis, an alkaline solution (e.g., sodium hydroxide) generally initiates hydrolysis of amide bonds by conversion to a carboxylic acid and an amine and/or ammonia. The inventors have surprisingly discovered a stepwise decrease in silk microfiber length as the hydrolysis time increases, and that smaller microfibers can be produced at elevated temperatures for a shorter period of time, e.g., as shown in FIG. 2A.

The desired microfiber size/length can be adjusted, in part, by controlling the concentration and/or strength of the alkaline solution, the duration of hydrolysis, hydrolysis temperature, or any combinations thereof. For example, in some embodiments, the alkaline solution selected to hydrolyze the native silk fiber can comprise a strong basic solution. As used herein, the term "a strong basic solution" refers to a basic solution with a pKa value of at least about 13 or above. Examples of strong basic solutions include, but are not limited to bases of alkali metals, e.g., sodium hydroxide, potassium hydroxide, lithium hydroxide, rubidium hydroxide, cesium hydroxide, calcium hydroxide, strontium hydroxide, barium hydroxide, or any combinations thereof. Additional examples of strong basic solutions include, without limitations, lithiumbis(trimethylsilyl)amide, lithium diisopropylamide, choline, Claisen's alkali, lithium amide, lithium diethylamide, lithium ethoxide, lithium hydride, lithium nitride, naphthalene sodium, phenyl lithium, phenyl potassium, phenyl sodium, potassium amide, potassium t-butoxide, potassium ethoxide, potassium hydride, potassium hydroxide, potassium-2-methyl-2-butoxide, sodium amide, sodium ethoxide, sodium hydride, sodium t-butoxide, sodium methoxide, sodium-2-methyl-2-butoxide, sodium methylsulfinyl methide (dimsyl sodium), tetraethylammonium hydroxide, triton b, trityl lithium, trityl potassium, and trityl sodium. These bases and information thereof may be found in Ford, Gordon, "The Chemist's Companion", pp. 67-80, John Wiley and Sons, New York, N.Y. (1972). In one embodiment, a strong basic solution comprising sodium hydroxide is used to contact a native silk fiber for formation of silk microfibers. In some embodiments, a strong basic solution can have a pH value of at least about 10, at least about 11, at least about 12, at least about 13, or at least about 14.

Figure 8A:
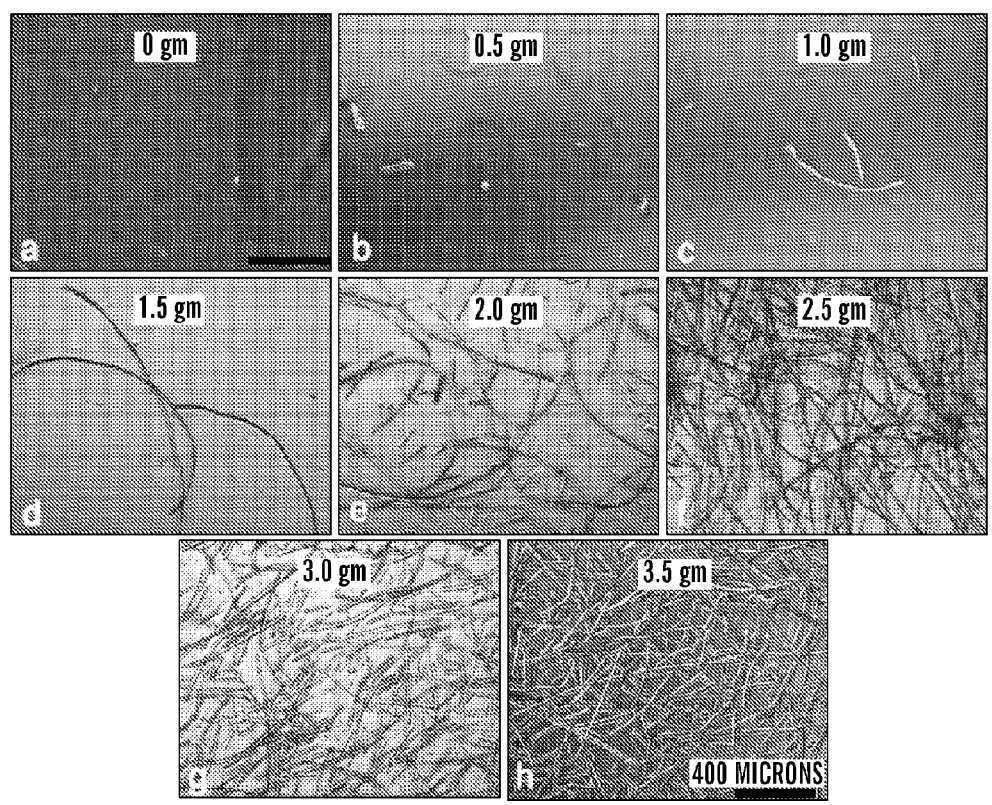
FIG. 8A is a set of microscopic images of hydrolyzed silk microfibers of various lengths depending on amount/concentration of NaOH used keeping incubation time constant. Experimental condition: 0.35 gm dried degummed silk fibers, 0-3.5 gm NaOH, 5 ml water and processed for 60 seconds (incubation time) as described herein.
Figure 8B:
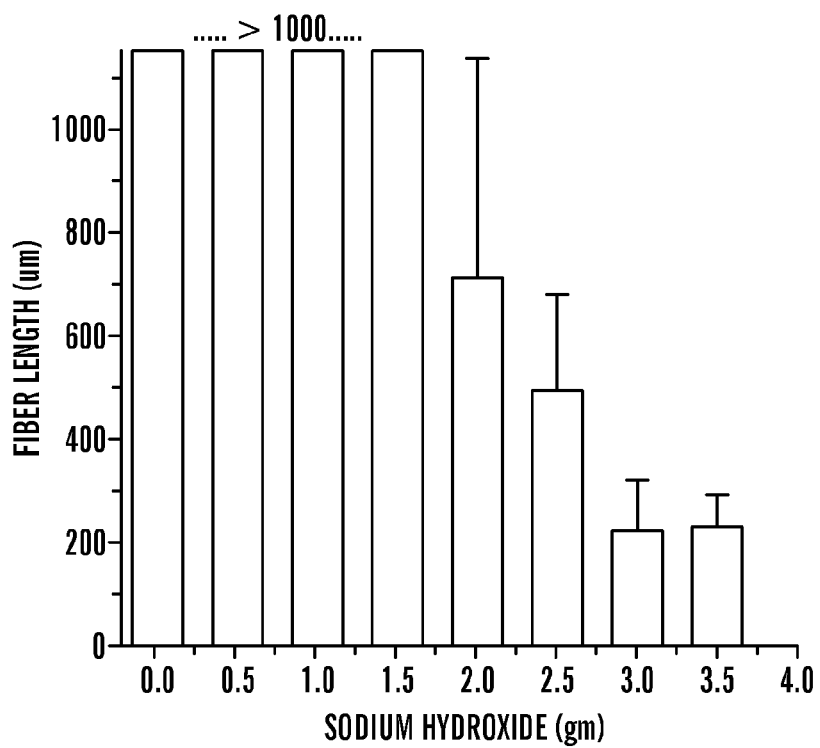
FIG. 8B is a bar graph showing silk microfiber size obtained for different amounts of NaOH used keeping incubation time constant.
Figure 9A:
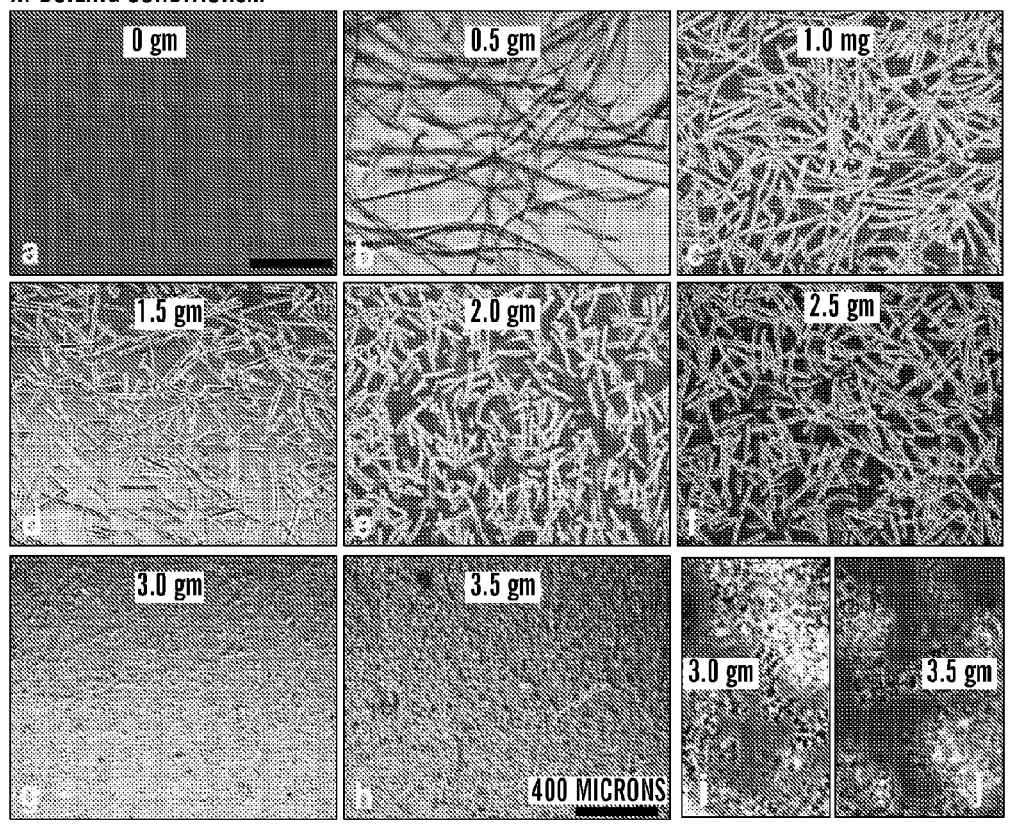
FIG. 9A is a set of microscopic images of hydrolyzed silk microfibers of various lengths obtained at boiling condition and varying NaOH amount. Experimental condition: 0.35 gm dried degummed silk fibers, 0-3.5 gm NaOH, 5 ml water and time=60 sec.
Figure 9B:
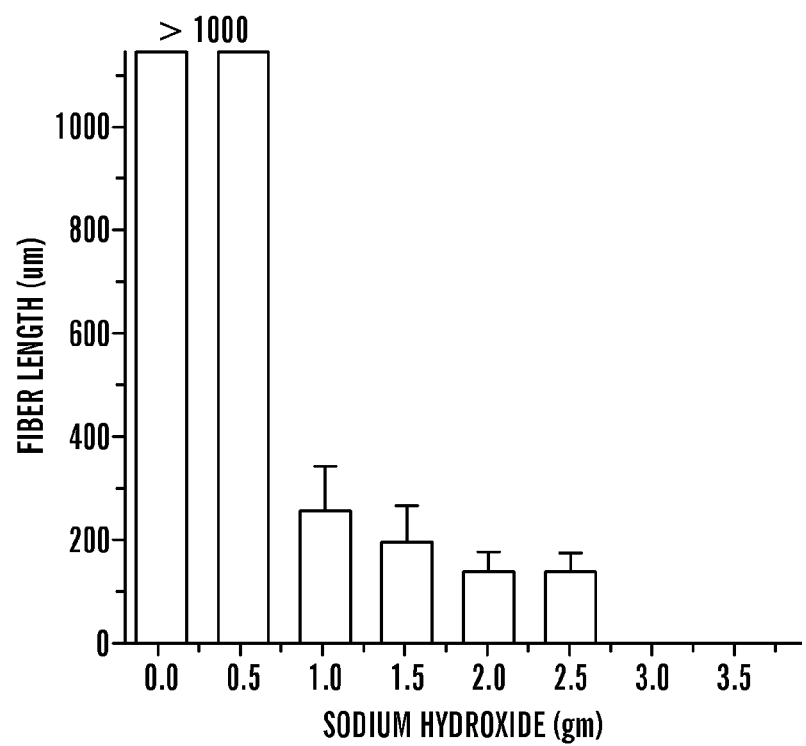
FIG. 9B is a bar graph showing silk microfiber size obtained at boiling condition and by varying NaOH amount keeping incubation time constant for 60 sec.

For each selected alkaline solution, the concentration of the alkaline solution, the duration and/or temperature of the hydrolysis can be adjusted accordingly to produce silk microfiber(s) of a desired length. The alkaline solution for use in hydrolysis of a native silk fiber (e.g., a degummed silk fiber) can be present in any concentration. In some embodiments, the alkaline solution can have a concentration of about 0.1 M to about 30 M, or about 0.5 M to about 25 M, or about 1 M to about 20 M. In some embodiments, the alkaline solution can be a concentrated alkaline solution, e.g., at a concentration of at least about 1 M or higher, for example, at least about 2 M, at least about 3 M, at least about 4 M, at least about 5 M, at least about 6 M, at least about 7 M, at least about 8 M, at least about 9 M, at least about 10 M, at least about 15 M, at least about 20 M, at least about 25 M, at least about 30 M or higher. Generally, higher concentrations of an alkaline solution (e.g., sodium hydroxide) can yield shorter silk microfibers, e.g., as shown in FIG. 8B and FIG. 9B, when keeping other hydrolysis condition parameters (e.g., temperature, and time) constant.

The hydrolysis of a native silk fiber (e.g., a degummed silk fiber) into a plurality of silk microfibers can be performed at any temperature. In some embodiments, the hydrolysis temperature can range from about 4° C. to about 100° C. In some embodiments, the hydrolysis temperature can range from about room temperature to about 100° C. In some embodiments, the hydrolysis temperature can be at least about 10° C. or higher, e.g., at least about 20° C., at least about 30° C., at least about 40° C., at least about 50° C., at least about 60° C., at least about 70° C., at least about 80° C., at least about 90° C., at least about 95° C., or higher. In some embodiments, the hydrolysis temperature can be about 100° C. Generally, higher temperatures increase the hydrolysis rate, while lower temperatures decrease the hydrolysis rate.

Depending on the hydrolysis condition (e.g., hydrolysis temperature, and/or concentration and/or pH of the alkaline solution) and/or desired microfiber length, the contact of the native silk fiber (e.g., a degummed silk fiber) with the alkaline solution can be maintained for any period of time ranging from seconds to minutes to hours. In some embodiments, the duration of hydrolysis can range from about 5 seconds to about 5 hours, or from about 10 seconds to about 3 hours, or from about 20 seconds to about 2 hour, or from about 30 seconds to about 1 hour. In some embodiments, the duration of hydrolysis can range from about 5 seconds to about 500 seconds. For example, the hydrolysis time can be shortened when a native silk fiber (e.g., a degummed silk fiber) is hydrolyzed in a higher concentration and/or higher pH of the alkaline solution, and/or at an elevated hydrolysis temperature. By way of example only, as shown in FIG. 2A, in approximately 60 seconds, silk microfibers ranging from about 10-20 μm were obtained at elevated temperatures (e.g., upon supply of external heat) as compared to 100-μm plus-sized microfibers obtained after about 720 seconds of hydrolysis in the absence of external heating (e.g., at room temperature).

After contact with an alkaline solution, in some embodiments, the method can further comprise neutralizing the alkaline mixture comprising one or more silk microfibers hydrolyzed from a native silk fiber (e.g., a degummed silk fiber). As used herein, the term "neutralizing" refers to alteration of the pH of an alkaline mixture such that the pH is no longer basic (e.g., the pH ranges from about 8.0 or lower). In some embodiments, the alkaline mixture can be neutralized to a physiological pH, e.g., pH~7. In some embodiments, the alkaline mixture can be neutralized to a pH value of less than 7. Methods for neutralizing an alkaline solution is known in the art, e.g., by addition of an acid solution (e.g., a strong acid solution such as hydrochloric acid or any acid solution that can reduce the pH to a desired value). In some embodiments, the alkaline mixture comprising one or more silk microfibers can be neutralized after the hydrolysis is complete. In some embodiments, the hydrolysis reaction of a native silk fiber (e.g., a degummed silk fiber)

in an alkaline solution can be inhibited or interrupted by neutralizing the mixture, or slowed down by reducing the pH of the mixture.

In some embodiments, the method can further comprise drying the silk microfibers, e.g., by air-drying or freeze-drying.

In some embodiments, while not necessary, the method can further comprise subjecting the silk microfibers to an annealing process. As used herein, the process of annealing involves inducing formation of beta-sheet secondary structure in the silk fibroin. This can be due to increased non-covalent interactions of silk fibroin. Such non-covalent interactions can include intra-molecular interactions, inter-molecular interactions, or both. Typically, non-covalent interactions are mediated by hydrogen bonds, which lead to increased beta sheet formation. Upon reaching a certain critical level of beta sheet secondary structure, silk fibroin is rendered insoluble, e.g., in an aqueous environment. This phenomenon is generally referred to as crystallinity and the status of such silk fibroin is referred to as Silk II. Thus, "annealing" involves a conformation change of silk fibroin to beta-sheet dominated (silk II) conformation, such that silk fibroin is crystallized and thus insoluble. Without wishing to be bound by a theory, it is believed that this conformational change is due to hydrogen-bonding and/or hydrophobic interactions mediated structural shift of silk fibroin to a higher beta sheet content.

There are a number of different methods for annealing silk fibroins in a silk microfiber. Without wishing to be bound by a theory, annealing can alter the crystallinity of the silk fibroin in the silk-based material, e.g., Silk II beta-sheet crystallinity. This can alter the rate of release of a molecule encapsulated in the silk-based material and/or alter the rate of degradation/dissolution of the silk-based material. Annealing can be done by any method known in the art, including, but not limited to, lyophilization or freeze-drying, gas-drying, alcohol immersion (e.g., ethanol, methanol), water annealing, water vapor annealing heat annealing, shear stress, ultrasound (e.g., by sonication), pH reduction (e.g., pH titration and/or exposing a silk-based material, e.g., a silk microfiber, to an electric field), and any combinations thereof.

For example, annealing can be done by one or more methods, including but not limited to, controlled slow drying (Lu et al., 10 Biomacromolecules 1032 (2009)); water annealing (Jin et al., Water-Stable Silk Films with Reduced β-Sheet Content, 15 Adv. Funct. Mats. 1241 (2005); Hu et al. Regulation of Silk Material Structure by Temperature-Controlled Water Vapor Annealing, 12 Biomacromolecules 1686 (2011)); stretching (Demura & Asakura, Immobilization of glucose oxidase with *Bombyx mori* silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposing a silk-based material to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, annealing is water annealing. There are a number of different methods for water annealing and are described in the U.S. Provisional Application No. 61/791,501 filed Mar. 15, 2013.

Another useful method for annealing the silk fibroin is to subject the silk-based material (e.g., a silk microfiber) to dehydration by the use of organic solvent, such as alcohols, e.g., methanol, ethanol, isopropyl, acetone, etc. Such solvent has an effect of dehydrating silk fibroin, which promotes "packing" of silk fibroin molecules to form beta sheet structures. In some embodiments, a silk-based material can be treated with an alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is about 90%.

Upon hydrolysis, a plurality of silk microfibers with various lengths can be produced. In some embodiments, the method can further comprise separating a subset of the silk microfibers of the desired length from the plurality of silk microfibers (and optionally a partially-hydrolyzed native silk fiber). By way of example only, a subset of the silk microfibers of the desired length can be separated from the plurality of silk microfibers (and optionally a partially-hydrolyzed native silk fiber) by sieving, filtering, dielectrophoresis, centrifugation, any art-recognized fiber sorting methods, or any combinations thereof.

Another aspect provided herein relates to a silk microfiber produced by one or more embodiments of the silk microfiber production method described herein. Thus, a silk microfiber produced by hydrolysis of a native silk fiber (e.g., a degummed silk fiber) (also termed herein as a "hydrolyzed silk microfiber") is provided herein. The length of the silk microfibers produced by the method described herein can range from about 1 µm to about 4 mm, about 1 µm to about 3 mm, about 1 µm to about 2 mm, about 1 µm to about 1 mm, about 1 µm to about 700 µm, or about 1 µm to about 500 µm. In some embodiments, the length of the silk microfibers ranges from about 10 µm to about 1000 µm, or about 10 µm to about 700 µm, or about 10 µm to about 500 µm.

Depending on natures and/or requirements of applications, the silk microfiber can be adapted to be degradable or non-degradable. For example, by controlling crystallinity or amounts of beta sheet structures present in silk fibroin, the degradation rate of the silk microfiber can be tuned for specific applications. In general, higher crystallinity or amounts of beta sheet structures present in silk fibroin can yield a silk-based material (e.g., a silk microfiber) less prone to degradation. Additionally or alternatively, without wishing to be bound by theory, the degumming time of a native silk fiber can be used to control degradability of silk microfibers (produced by hydrolysis of a degummed silk fiber).

In some embodiments, the silk microfiber can be coated or conjugated with at least one or more additives described herein. In some embodiments, the silk microfiber can be coated or conjugated with a biological macromolecule, e.g., but not limited to, a protein, a peptide, an aptamers, a nucleic acid, or any combinations thereof. In some embodiments, the silk microfiber can be coated or conjugated to a therapeutic agent. In some embodiments, the silk microfiber can be coated or conjugated to a polymeric material (e.g., but not limited to, hyaluronic acid, chitosan, collagen, PLGA, PCL, PMMA), and/or ceramic material (e.g., but not limited to, tricalcium phosphates, hydroxyapatite (HAP), and/or bioactive glass).

An Exemplary Method of Making Micron Range Silk Fibers (or Silk Microfibers)

In one embodiment, a silk microfiber (or a micron range silk fiber) can be produced by hydrolysis of a degummed silk fiber. In some embodiments, the silk microfiber preparation process (FIG. 1A) can be divided into three stages: (a) preparation of degummed silk fibers from cocoons, (b) hydrolysis of degummed silk fibers into micron sized fibers or silk microfibers; and (c) washing/neutralization of the microfibers followed by lyophilization.

The following protocol is merely an illustrative example of one embodiment of a silk microfiber process, and by no means is it construed to be limiting. It will be apparent to those skilled in the art that various modifications (e.g., but not limited to, degumming time, alkaline solution concentration and strength, hydrolysis temperature, hydrolysis time, mass ratio of alkalis to native silk fibers), additions, substitutions, and the like can be performed without altering the scope of the inventions, and such modifications and variations are also encompassed within the scope of the inventions.

(a) Degumming of Native Silk Fibers:
1. Cut dried cocoons, e.g., with scissors, into 4 pieces (final weight of cut cocoons used can be 20 μm, for example).
2. Prepare 2 separate glass beakers filled with 3 L water each and heat it up until boiling.
3. Weigh sodium carbonate to be added to the beaker with 3 L water (each) to make 0.02 (M) 3 L solution.
4. Add sodium carbonate to the beakers when water starts to boil and let it dissolve.
5. Put the cocoon pieces in the boiling water with 0.02 (M) sodium carbonate, and stir.
6. Boil for 10 minutes with occasional stirring.
7. After 10 min of boiling, carefully transfer the silk fibers from the first beaker to the second beaker with 0.02 (M) sodium carbonate.
8. Boil for another for 10 min with occasional stirring.
9. Take the degummed fibers out of the beaker and rinse with cold water (~5-7 washes) until all sodium carbonate is removed.
10. Squeeze the silk with hands to remove excess water.
11. Put in fume/chemical hood to air dry for at least 12 hours or longer.

Hydrolysis of Degummed Silk Fibers:

Sodium hydroxide pellets (NaOH) weighing ~3.5 μm (to obtain ~17.5 M solution) can be added to ~5 ml of distilled water. When approximately 70% of the NaOH pellets are dissolved with an exothermic reaction, the dried degummed silk fibers weighing ~0.35 μm were added and stirred, e.g., with a spatula.

Figure 7A:
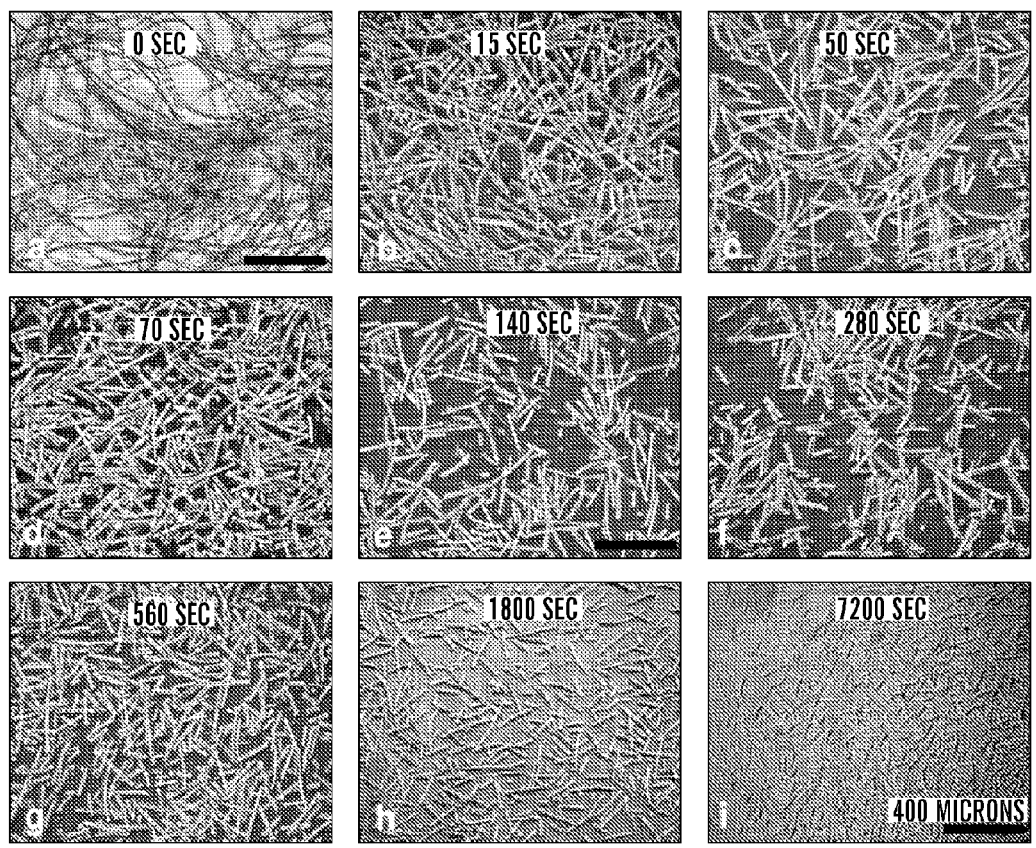
FIG. 7A is a set of microscopic images of hydrolyzed silk microfibers of various lengths depending on incubation time. Experimental condition: 0.35 gm dried degummed silk fibers, 3.5 gm NaOH, 5 ml water and processed as described herein.
Figure 7B:
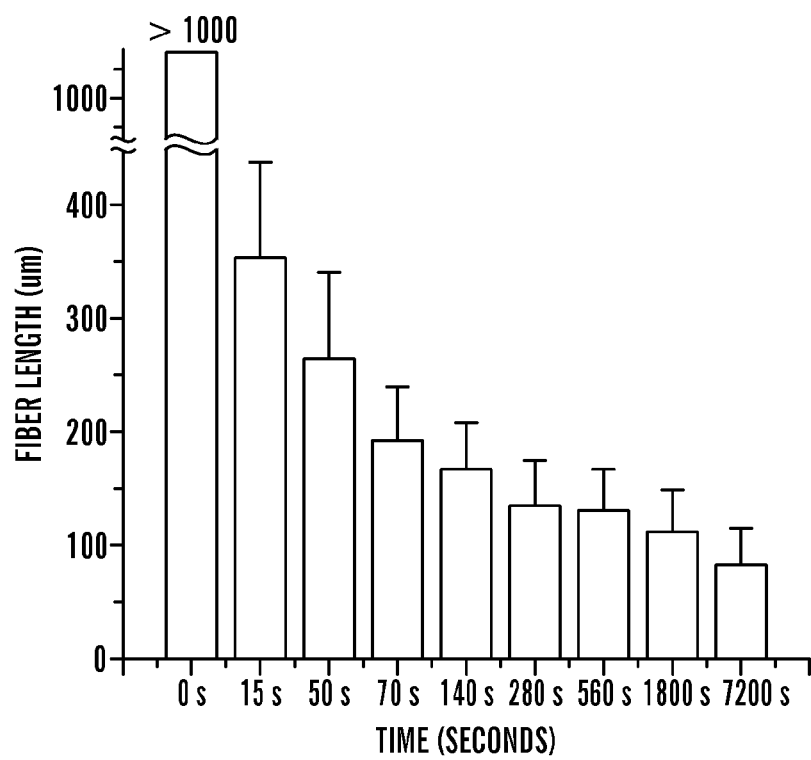
FIG. 7B is a bar graph showing silk microfiber size obtained for different incubation time.
Figure 7C:
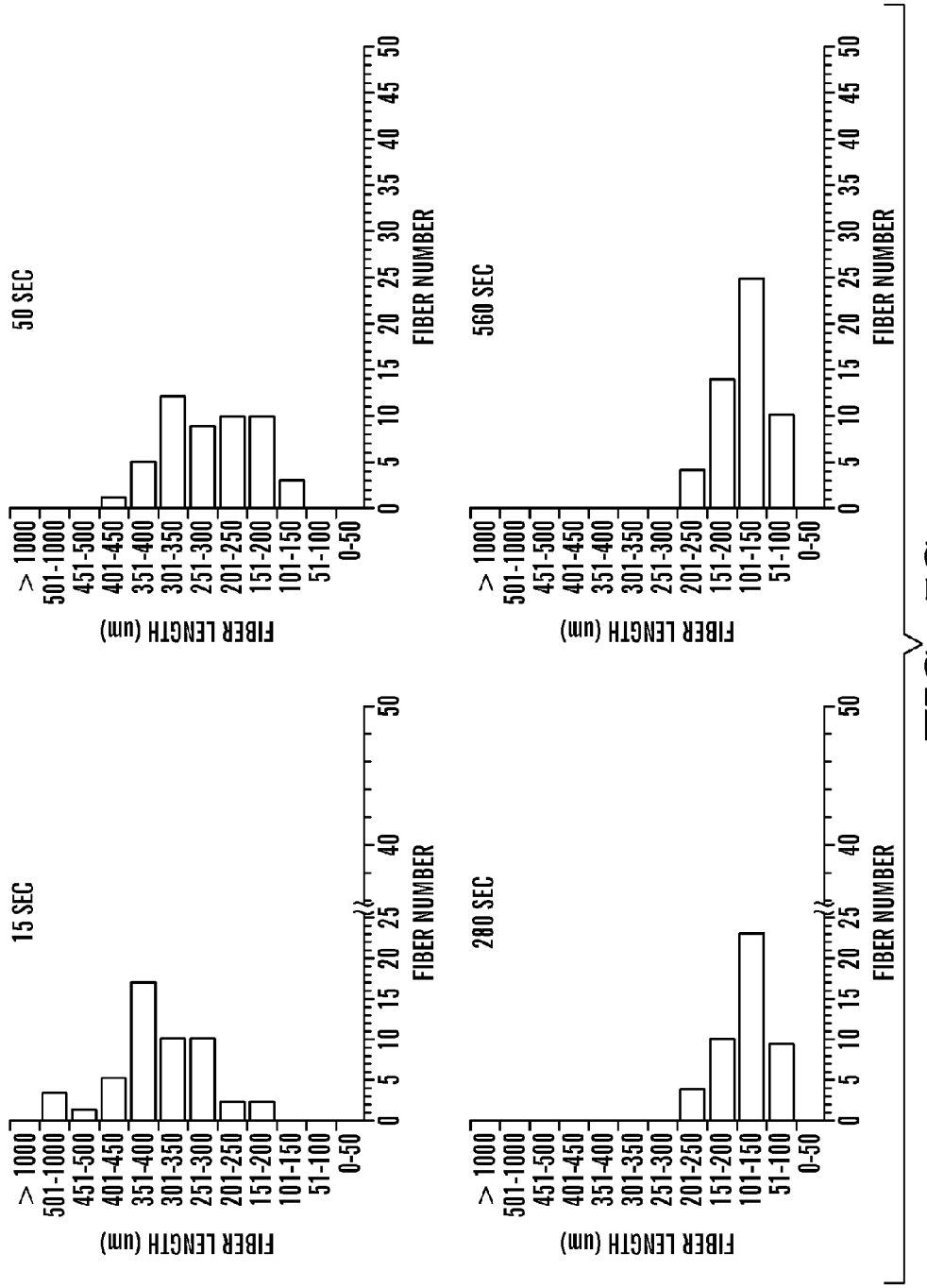
FIG. 7C is a set of bar graphs showing silk microfiber size distribution for different incubation time periods.
Figure 7C:
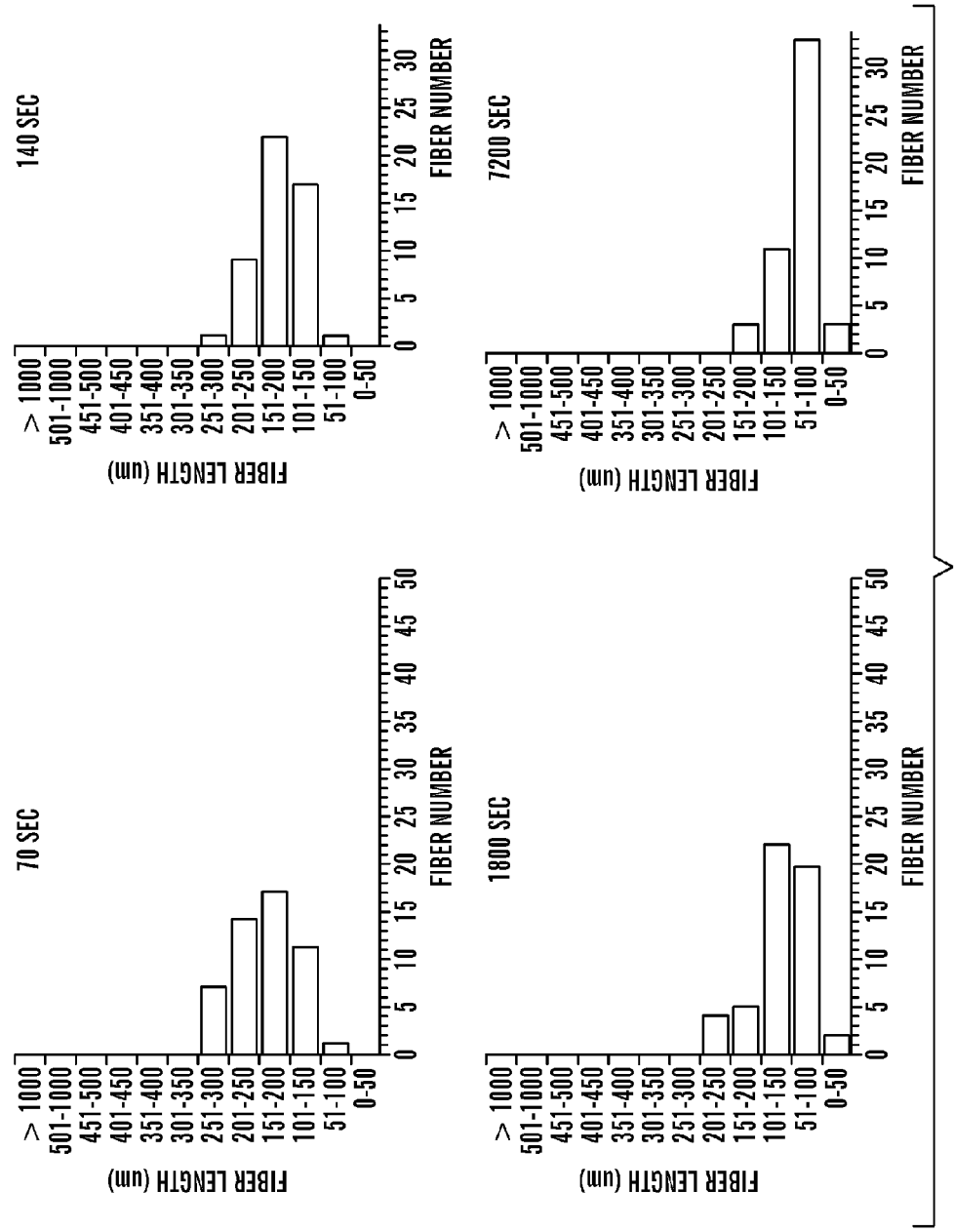

The hydrolysis reaction starts immediately leading to chopping of fibers into smaller pieces. Depending on incubation time (hydrolysis time), i.e. how long the hydrolysis reaction is left to go, different sized microfibers, i.e. shorter incubation time generally yields longer microfibers while longer incubation yields shorter microfibers (FIGS. 7A-7C).

Washing/Neutralization of Silk Microfibers:

To stop hydrolysis, ~45 ml of water is added to the reaction mixture and centrifuged at 3,500 rpm for 5 minutes. The supernatant is discarded and the microfibers are resuspended in 50 ml of water, stirred and centrifuged. This step can be repeated between 5 and 8 times or more, to remove any remaining alkali. The pH of the solution is measured and the pH is adjusted to ~7.0 using an acid, e.g., hydrochloric acid. The neutralized microfiber solution is again centrifuged at 3,500 rpm for ~5 minutes and resuspended in water (repeated about 3-5 times). Finally the microfibers are suspended in PBS and lyophilized to generate a silk microfiber powder. To obtain large (about 400-about 500 μm long) and medium (about 150-about 200 μm long) silk microfibers, the hydrolysis reaction was carried for 30 and 180 seconds, respectively. To obtain very fine/smaller (about 10-about 20 μm long) silk microfibers, the reaction mixture was set up in a boiling water bath for ~60 sec to aid rapid hydrolysis.

Times for hydrolysis is not absolute and may vary depending on various factors including, e.g., but not limited to, strength, purity of NaOH, brand purchased from, how old are the NaOH pellets, quality of degumming, individual handling. Thus, in some embodiments, the method can further comprise monitoring the processed microfibers in a microscope from time to time during the hydrolysis (e.g., taking a small amount in a glass slide). The hydrolysis reaction can then be stopped when the microfiber sizes reach optimal. Further on scaling up the hydrolysis reaction can result in different time points for obtaining different microfiber sizes than specific time frames indicated herein. One of skill in the art can scale up and optimize the hydrolysis condition to produce silk microfibers of desired lengths, e.g., by measuring microfiber lengths obtained as one hydrolysis parameter is varied with others being maintained constant as described below.

Effect of an Alkaline Solution (e.g., Sodium Hydroxide) Concentration/Amount on Size of Silk Microfibers.

Figure 8C:
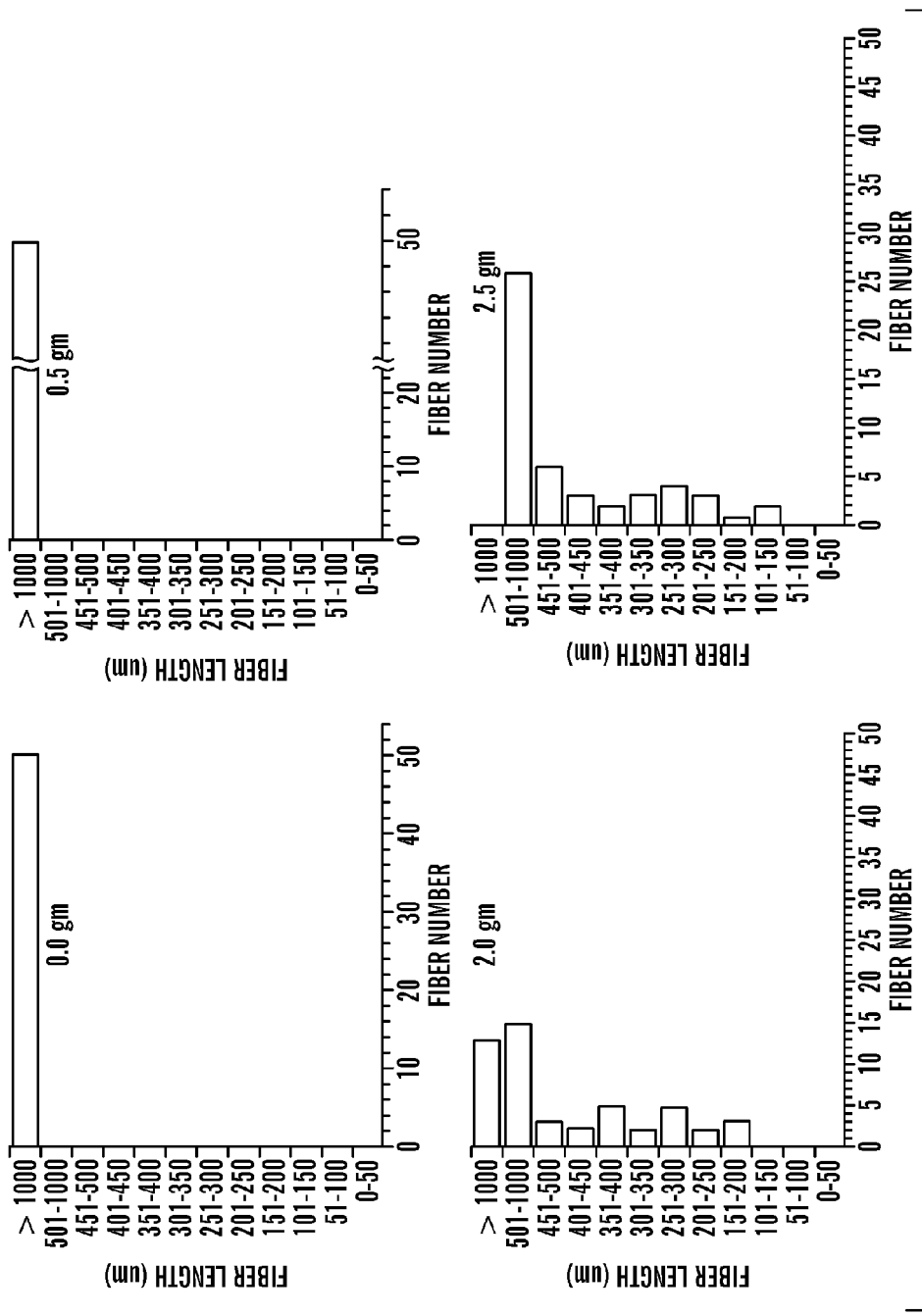
FIG. 8C is a set of bar graphs showing silk microfiber size distribution for different amounts of NaOH used keeping incubation time constant.
Figure 8C:
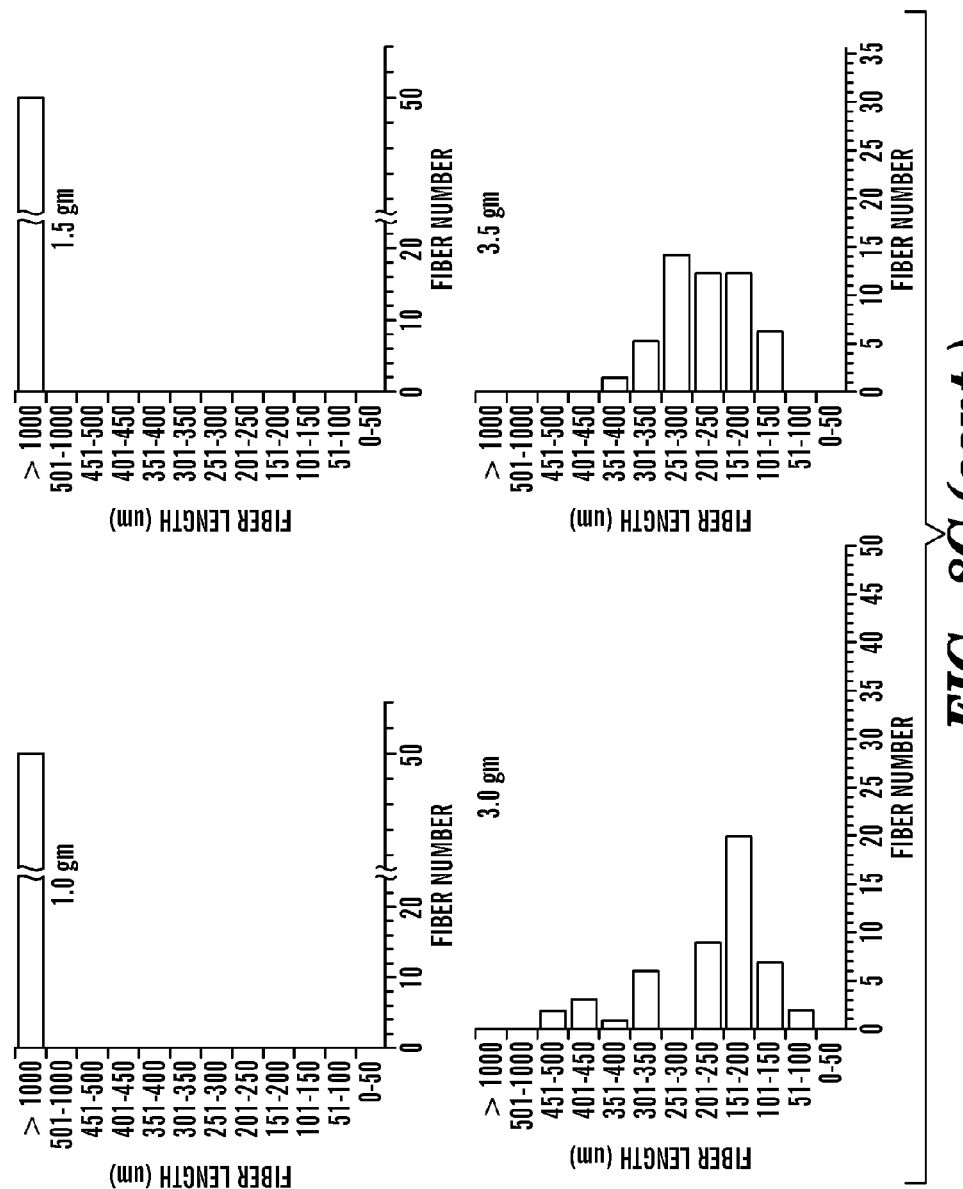

Varying an alkaline solution (e.g., NaOH) concentration/amount can vary microfiber length, and the hydrolysis reaction of degummed silk fibers. For example, the effect of NaOH concentration/amount on microfiber length, and hydrolysis of degummed silk fibers can be assessed by varying amounts of NaOH pellets (0-~3.5 μm) used while keeping the hydrolysis time constant (e.g., for ~60 seconds). The general method remains the same as described above using 5 ml of water and 0.35 μm of degummed silk fibers to start the reaction. Smaller length microfibers were obtained using higher amounts (3.5 μm) of NaOH pellets for the same periods of hydrolysis time (FIGS. 8A-8C)

Effect of Hydrolysis Temperature and Amount of an Alkaline Solution (e.g., NaOH) on Rate of Hydrolysis and on Size of Silk Microfiber.

Figure 9C:
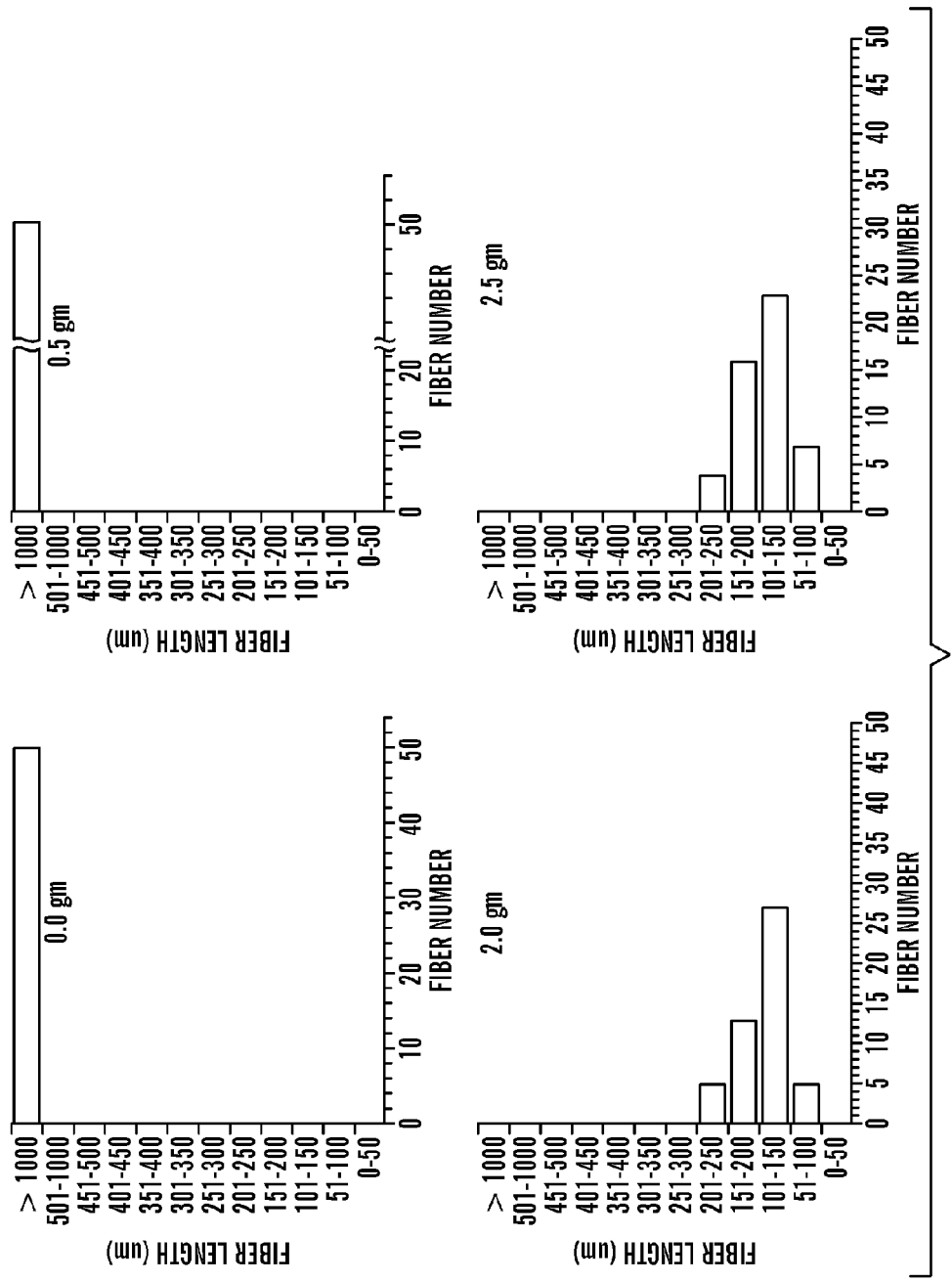
FIG. 9C is a bar graph showing silk microfiber size distribution using boiling condition and varying amounts of NaOH. Incubation time was kept constant at 60 sec.
Figure 9C:
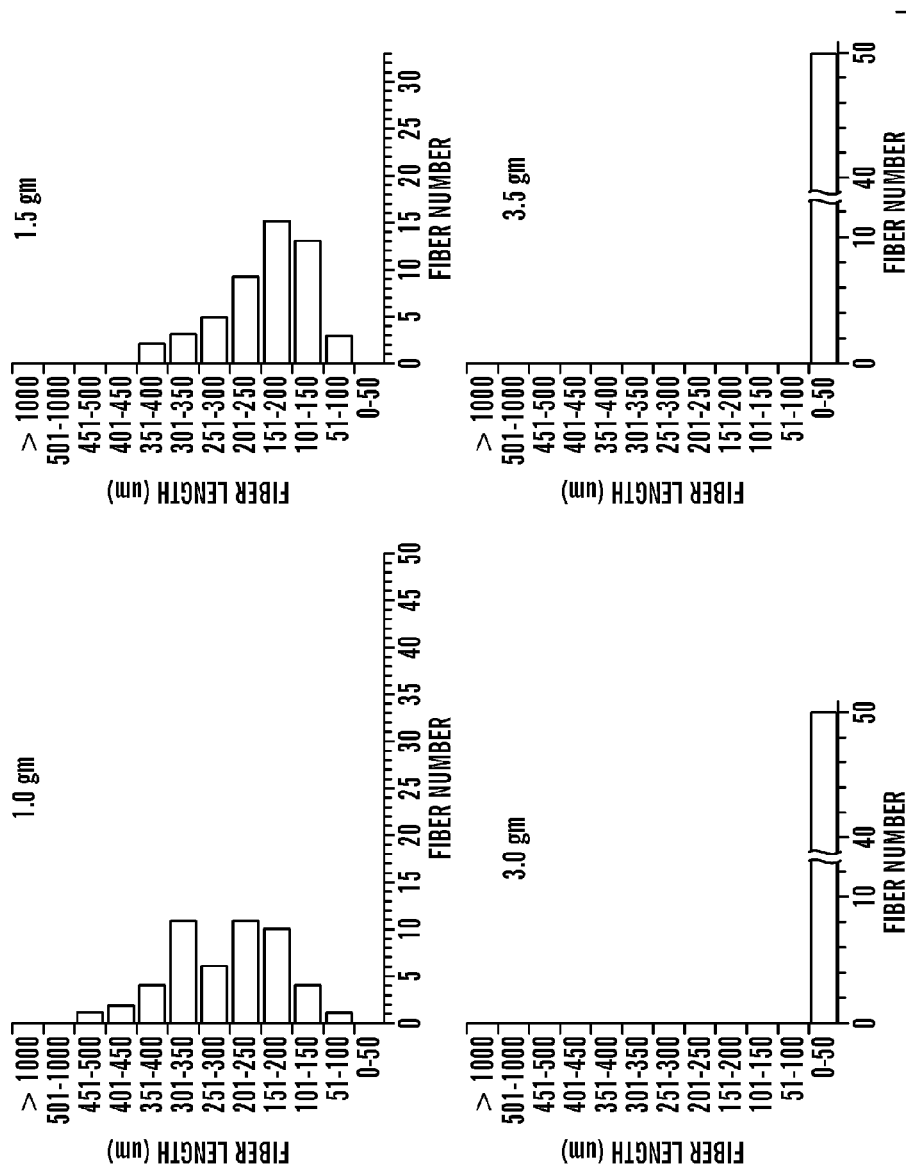
Figure 10:
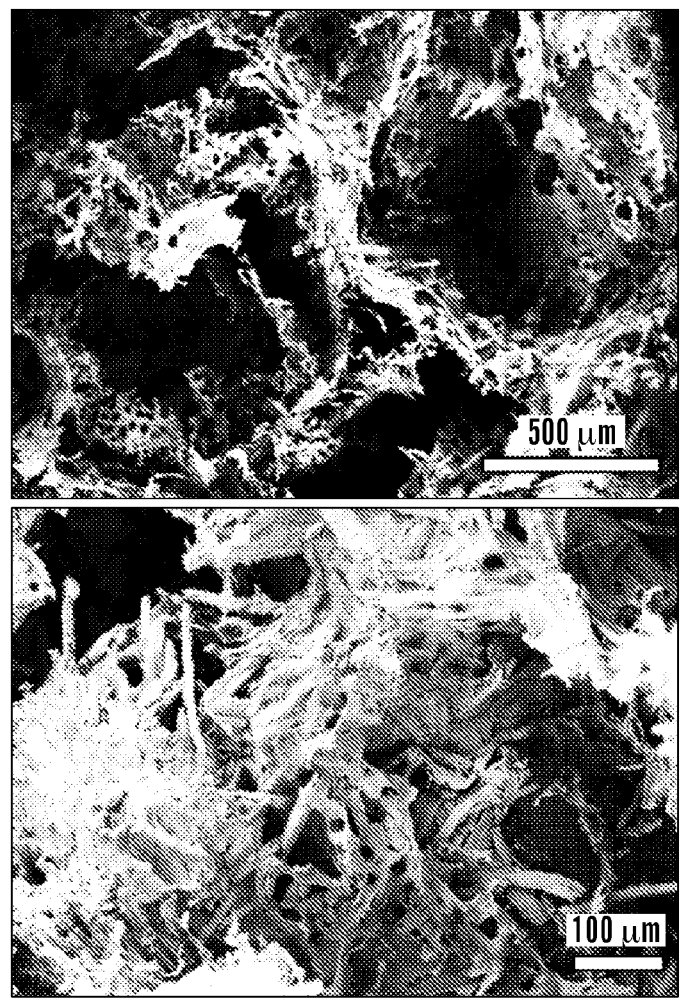
FIG. 10 is a set of SEM images showing porous scaffolds architecture and microfibers embedded within a silk composite.

Varying the hydrolysis reaction temperature can vary microfiber length, and hydrolysis of degummed silk fibers. For example, the effect of hydrolysis reaction temperature on microfiber length and hydrolysis of degummed silk fibers can be assessed at boiling condition (95-100° C.) and by varying amounts of NaOH pellets (0-~3.5 μm). The hydrolysis time was kept constant, e.g., for 60 seconds. The general method of producing a silk microfiber remains the same as described above using 5 ml of water and ~0.35 μm of silk fibers to start a hydrolysis reaction. Smaller length fibers were obtained using smaller amounts of NaOH pellets at elevated temperatures, e.g., boiling conditions (FIGS. 9A-9C) as compared to experiments performed at lower temperatures (e.g., at room temperature) with varying NaOH (FIGS. 8A-8C) for the same periods of hydrolysis time.

In some embodiments, the methods described herein can generate silk microfiber lengths ranging from about 10 microns to about 700 microns, and it can be extended further in both ways following the method described herein. In some embodiments, the silk microfiber lengths can be longer than 700 microns. In some embodiments, the silk microfiber lengths can be shorter than 10 microns. Bulk quantities of the microfibers can be produced using one or more embodiments of the production method described herein with minimal resources, e.g., as compared to milling method which requires expensive equipment like high temperature and high pressure grinders.

Uses of Silk Microfibers Described Herein

The micron range silk fibers or silk microfibers can be used in various applications, e.g., ranging from cosmetics, tissue regeneration, chemical processing, to material processing. In some embodiments, the wide range of silk microfibers can be used in cosmetics as fillers and/or in preparation of materials to design high strength composites. Accordingly, in yet another aspect, a composition comprising at least one embodiment of a silk microfiber described herein is also provided. In some embodiments, a composition can comprise a plurality of (e.g., at least 2 or more) silk microfibers described herein. In some embodiments where a composition comprises more than 2 silk microfibers, the silk microfibers can have substantially the same or varying lengths.

The composition can be formulated in any form to suit the need of an application. By way of example only, the composition can be used to form a construction material, a cosmetic formulation, a consumer product, a medical device or component, a coating, a filler, or a tissue engineering or reconstruction scaffold.

In some embodiments, the composition can further comprise at least one or more (e.g., at least 1, at least 2, at least 3, at least 4, at least 5 or more) additives as described herein. A skilled artisan can determine appropriate additive(s) to be included in the composition for various applications. By way of example only, a composition used for bone repair can comprise at least one osteogenic, osteoinductive, and/or ostenconductive agent as described later.

In some embodiments, the composition for in vivo applications can further comprise a pharmaceutically acceptable carrier. As used herein, the term "pharmaceutically acceptable carrier" refers to a pharmaceutically-acceptable material, composition or vehicle for administration of the silk microfibers, and optionally an active agent. Pharmaceutically acceptable carriers include any and all solvents, dispersion media, coatings, antibacterial and antifungal agents, and isotonic and absorption delaying agents, which are compatible with the silk microfibers and the activity of the active agent, if any, and are physiologically acceptable to the subject. The pharmaceutical formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

Additionally, various additives which enhance the stability, sterility, and isotonicity of the injectable compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like. The injectable compositions can also contain auxiliary substances such as wetting or emulsifying agents, pH buffering agents, gelling or viscosity enhancing additives, preservatives, colors, and the like, depending upon the preparation desired. Standard texts, such as "REMINGTON'S PHARMACEUTICAL SCIENCE", 17th edition, 1985, incorporated herein by reference, may be consulted to prepare suitable preparations, without undue experimentation.

Viscosity of the injectable compositions can be maintained at the selected level using a pharmaceutically acceptable thickening agent. In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected, and the desired viscosity for injection. The important point is to use an amount which will achieve the selected viscosity, e.g., addition of such thickening agents into some embodiments of the injectable compositions.

Typically, any additives (in addition to the silk microfibers described herein) can be present in an amount of 0.001 to 50 wt % dry weight or in a buffered solution. In some embodiments, the additive can be present in the order of micrograms to milligrams to grams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any pharmaceutical composition to be administered to a subject in need thereof, it is preferred to determine toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan.

In some embodiments, the composition can further comprise a matrix material. The matrix material can comprise a polymeric and/or a ceramic material. In these embodiments, the silk microfiber(s) can be dispersed in the matrix material. Thus, in some embodiments, the composition can further comprise a composite material comprising silk microfibers distributed in a matrix material as described below.

Composite Materials:

Accordingly, a further aspect provided herein relates to a composite material comprising one or more silk fibers described herein distributed in a matrix material, e.g., a polymeric material and/or a ceramic material. In some embodiments, the silk microfibers can have a length ranging from about 1 μm to about 4 mm, or about 1 μm to about 3 mm, or about 1 μm to about 2 mm, or about 1 μm to about 1 mm, or about 1 μm to about 700 μm. In some embodiments, the silk microfibers can have a length ranging from about 5 μm to about 1000 μm, or about 10 μm to about 700 μm.

Any natural or synthetic polymeric material can be used as a matrix material in the composite material described herein. The polymeric material can be degradable or non-degradable, e.g., based on the need of a selected application. In some embodiments, the polymeric material can be biocompatible and/or biodegradable. As used herein, the term "biodegradable" refers to the ability of a polymeric material to erode or degrade in vivo to form smaller chemical fragments. Degradation may occur, for example, by enzymatic, chemical or physical processes. As used herein, the term "non-biodegradable" refers to the ability of a polymeric material to resist erosion or degradation in vivo. Thus, a non-biodegradable material can stay in vivo for a significantly long amount of time, or even permanently.

Examples of polymeric materials that can be used in the composite material include, but are not limited to, silk or silk fibroin, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, poly(lactide-co-glycolide) (PLA-PLA-PGA), polymethylmethacrylate, polyanhydride, polyorthoester, polycaprolactone, polyfumarate, polyester, polyamide, polycarbonates, polyanhydrides, polyorthoesters, polycaprolactone, polyesteramides, polycyanoacrylate, polyetherester, poly(phosphates), poly(phosphonates), poly(phosphites), polyhydric alcohol esters, polyethylene, polypropylene, polytetrafluoroethylene, polyurethanes, silicon, polyacrylates, ethylene-vinyl acetates (and other acyl-substituted cellulose acetates), polystyrenes, polyvinyl oxides, polyvinyl fluorides, poly(vinyl imidazoles), chlorosulphonated polyolefins, polyethylene oxides, polyvinyl alcohols (PVA), blends and copolymers thereof.

In some embodiments, the polymeric material can comprise a silk-based material or a silk fibroin-based material to form a silk microfiber-silk composite as described below.

In some embodiments, one or more silk microfibers can be additionally or alternatively distributed in a ceramic material, e.g., but not limited to, calcium phosphate, calcium sulfate, hydroxyapatite, bioactive glass, or any combinations thereof.

The silk microfiber(s) can be present in a matrix material (e.g., polymeric material such as silk and/or ceramic material) in any amount. In some embodiments, the matrix material (e.g., a polymeric material and/or ceramic material) and silk microfibers can be present in a weight ratio of about 100:1 to about 1:100, about 75:1 to about 1:75, about 50:1 to about 1:50; or about 25:1 to about 1:25. In some embodiments, the matrix material (e.g., a polymer material and/or ceramic material) and silk microfibers can be present in a weight ratio of about 1:1 to about 1:100; about 1:1 to about 1:75; about 1:1 to about 1:50, about 1:1 to about 1:25; about 1:1 to about 1:10, or about 1:1: to about 1:5.

In some embodiments, the silk microfibers can be used as reinforcing fillers in a matrix material (e.g., a polymeric material such as silk and/or ceramic material), e.g., to enhance the mechanical property (e.g., compressive or load-bearing property) of the bulk matrix material. In some embodiments, the amounts and/or lengths of the silk microfibers can be optimized for generating a composite material with desired mechanical properties. For example, in some embodiments, the composite material can have a compressive modulus of at least about 1 MPa, at least about 2 MPa, at least about 3 MPa or higher in its hydrated state (including, e.g., at least about 5 MPa, at least about 10 MPa, at least about 15 MPa, at least about 20 MPa, at least about 30 MPa, at least about 40 MPa, at least about 50 MPa, at least about 60 MPa, at least about 70 MPa, at least about 80 MPa, at least about 90 MPa, at least about 100 MPa, at least about 150 MPa, at least about 200 MPa, at least about 250 MPa, at least about 300 MPa or higher in its hydrated state). In some embodiments, the composite material can have a compressive modulus of at least about 10 MPa or higher in its hydrated state. Methods to determine mechanical properties (e.g., compressive (elastic) modulus) are known in the art. For example, the compressive modulus (or compressive elastic modulus) of a composite material can be determined by a compression test as described in Example 1. Other art-recognized methods to determine compressive modulus (or compressive elastic modulus) of a composite material can also be used herein.

Figure 4:
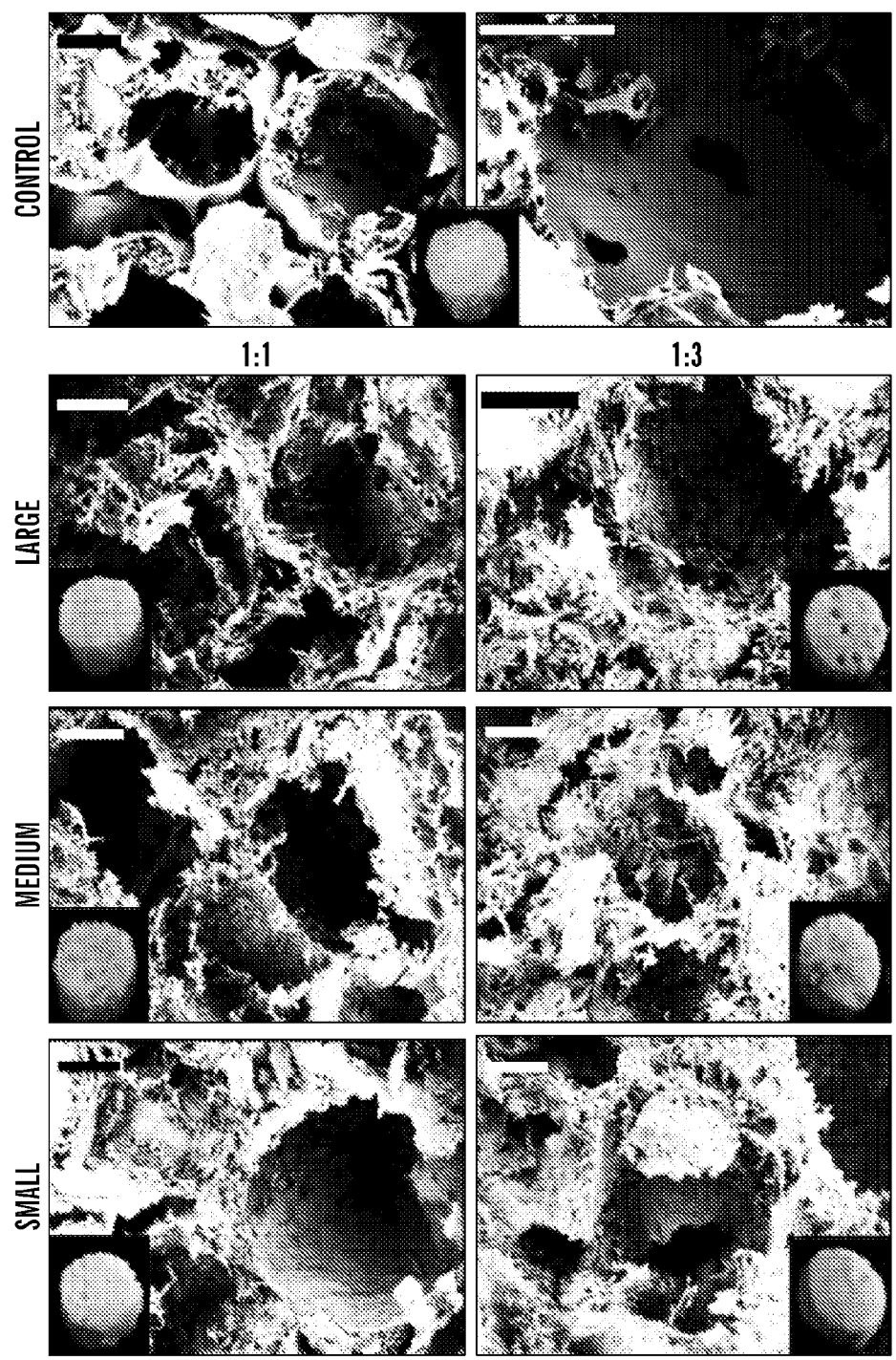
FIG. 4 is a set of SEM images showing exemplary silk scaffold characteristics including pore size, microfiber bonding, porosity, and surface roughness. Inset image shows fabricated scaffold used for cell culture. Scale bar represents 200 microns.
Figure 5A:
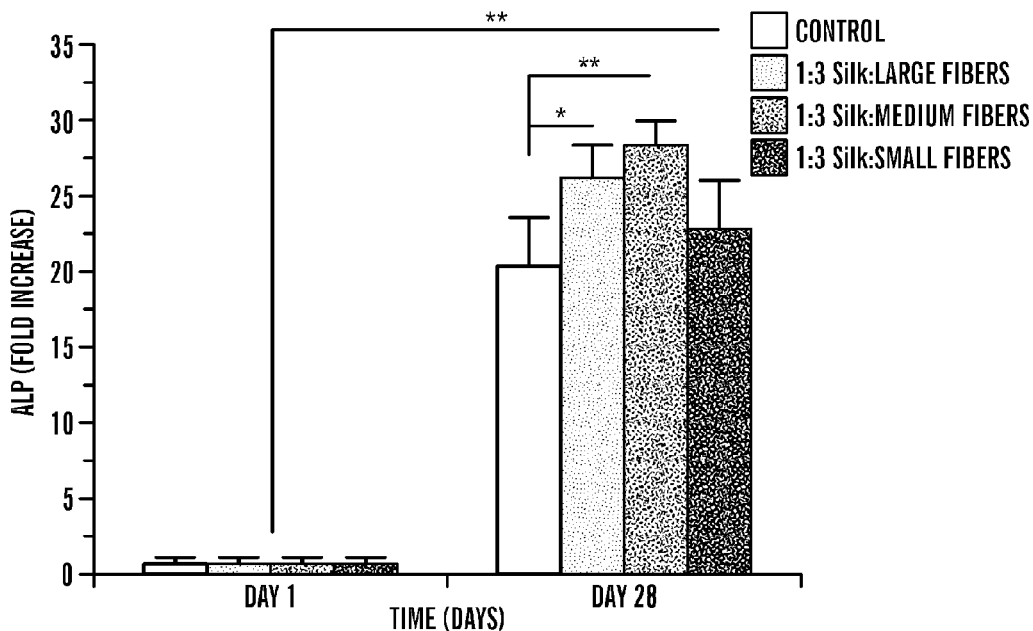
FIGS. 5A-5D are bar graphs showing fold increase in osteogenic gene expression of hMSCs seeded in silk microfiber reinforced scaffolds during differentiating conditions.
Figure 5B:
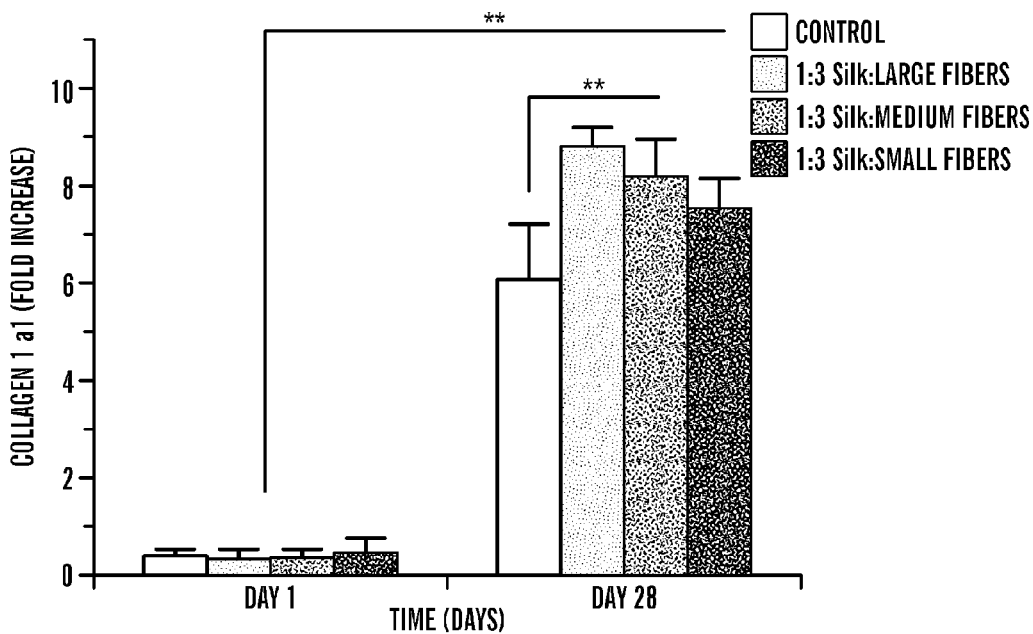
Figure 5C:
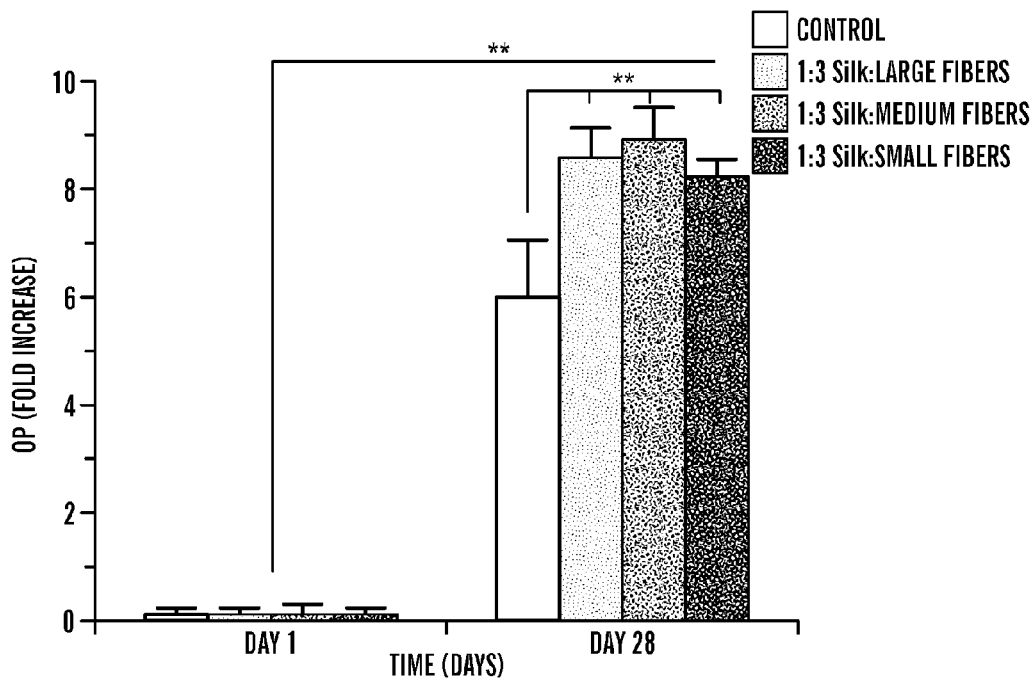
Figure 5D:
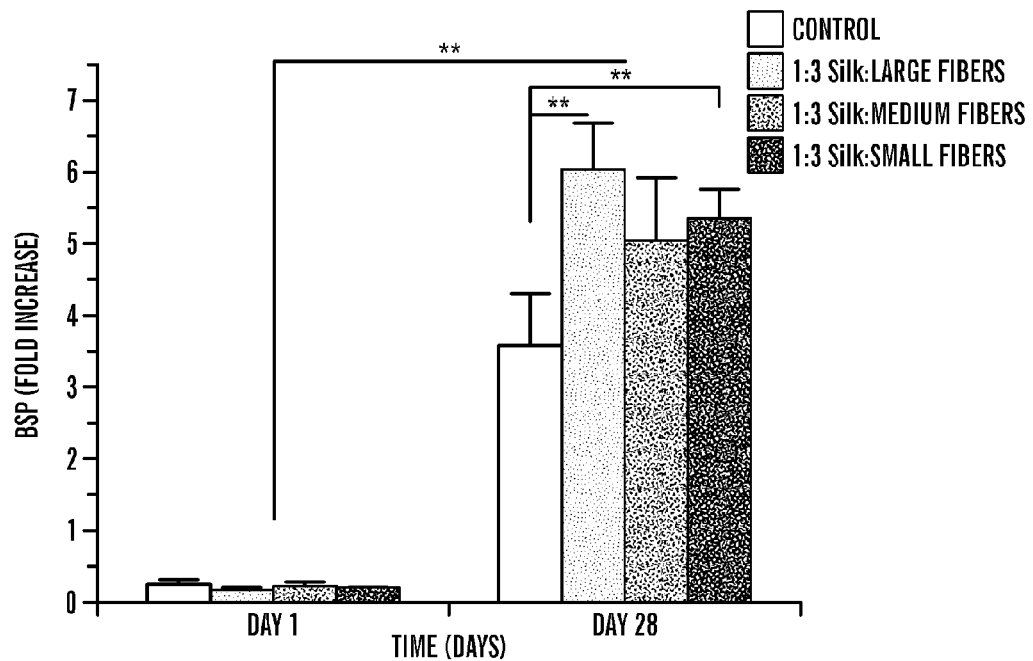

The matrix material (e.g., a polymeric material such as silk and/or ceramic material) can be non-porous or porous. In some embodiments where the matrix material is porous, at least a portion of the pores within the matrix material do not have a smooth surface wall. In this embodiment, the inventors have discovered that the overall surface roughness, including the roughness of pore walls and interconnectivity, increased, e.g., for both weight ratios (silk fibroin: silk microfibers) of 1:1 and 1:3 upon the addition of longer silk microfibers (e.g., ~400-500 μm) when compared to smaller fibers (e.g., ~10-20 μm) (FIG. 4). Medium-length fibers (e.g., ~150-200 μm) showed an intermediate roughness, and smaller fibers had a more compact structure with less fibrous solid walls (FIG. 4). As shown in FIG. 4, bonded silk microfibers can be seen intertwined throughout the silk-based material making the surface rough and porous with good miscibility. This enhancement of roughness is an added advantage for some embodiments of composite materials described herein as interconnected porous structures are important for new bone tissue regeneration, permitting integration via adequate neovascularization and nutrient/metabolic waste diffusion. Further, using, e.g., salt leaching, control over the range of pore sizes and geometry can be attained by choosing the appropriate salt grain size (e.g., 800 μm grains were used in the study as shown in FIG. 4) to mimic bone features related to distinct anatomical bone sites.

The composite material comprising one or more silk microfibers distributed in a matrix material can be in any form selected from the group consisting of a film, a sheet, a gel, a mesh, a mat, a non-woven mat or fabric, a scaffold, a tube, a slab or block, a particle, a fiber, a 3-dimensional construct, an implant (including, e.g., but not limited to, a screw, and a plate), a high-density material, a porous material, a non-porous material, a reinforced material, a machinable material, a magnetic responsive material, a microneedle, and any combinations thereof.

In some embodiments, higher silk microfibers distributed in a matrix material can lead to a greater packing density and thus provide a high-density composite material. For example, in some embodiments, silk microfibers can be distributed in a matrix material in a weight ratio (silk microfiber:matrix material) of greater than 1:1, e.g., about 2:1, about 3:1, about 4:1, about 5:1, about 6:1, about 7:1, about 8:1, about 9:1, about 10:1 or higher, to generate a high-density composite material.

In some embodiments, one or more silk microfibers distributed in a matrix material can yield stronger composites with higher mechanical properties. Thus, in some embodiments, the composite material can be a reinforced material. In one embodiment, a reinforced material is a composite material comprising a plurality of silk microfibers distributed in a matrix material (e.g., a silk fibroin-based material), wherein the plurality of silk microfibers are present in the matrix material (e.g., a silk fibroin-based material) at a density or an amount sufficient to increase at least one mechanical property (e.g., but not limited to, compressive modulus, compressive strength, compressive toughness, ultimate compressive strength) by at least about 10%, at least about 20%, at least about 30%, at least about 40%, at least about 50%, at least about 60%, at least about 70%, at least about 80%, at least about 90%, at least about 95% or higher, as compared to the mechanical property of the matrix material (e.g., silk fibroin-based material) without silk microfibers. In some embodiments, the amount or density of silk microfibers present in a matrix material (e.g., a silk fibroin-based material) is sufficient to increase at least one mechanical property (e.g., but not limited to, compressive modulus, compressive strength, compressive toughness, ultimate compressive strength) by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, or higher, as compared to the mechanical property of the matrix material (e.g., silk fibroin-based material) without silk microfibers.

In some embodiments, the amount or density of silk microfibers present in a matrix material (e.g., a silk fibroin-based material) is sufficient to increase at least compressive modulus by at least about 10%, at least about 20%, at least about 30%, at least about 40%, at least about 50%, at least about 60%, at least about 70%, at least about 80%, at least about 90%, at least about 95% or higher, as compared to the compressive modulus of the matrix material (e.g., silk fibroin-based material) without silk microfibers. In some embodiments, the amount or density of silk microfibers present in a matrix material (e.g., a silk fibroin-based material) is sufficient to increase at least compressive modulus by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, or higher, as compared to the compressive modulus of the matrix material (e.g., silk fibroin-based material) without silk microfibers.

In some embodiments, the composite material is machinable. As used herein, the term "machinable" means a material which can be readily subjected to machining by any methods or operations known in the art, including, e.g., but not limited to, computer numerical control (CNC) machining, cutting, milling, turning, drilling, shaping, planing, broaching, sawing, burnishing, grinding, and the like. In some embodiments, silk microfibers distributed in a matrix material yield a stronger material and thus permit the composite material to be machinable.

In some embodiments, the matrix material (e.g., a polymeric material such as silk and/or ceramic material) can comprise an additive as described herein. Examples of the additive include, without limitations, cells; biopolymers; plasticizers; nanoparticles (e.g., gold nanoparticles); therapeutic agents; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; enzymes; an extract made from biological materials such as bacteria, plants, fungi, or animal cells; animal tissues; naturally occurring or synthetic compositions; and any combinations thereof.

The composite material can be adapted to a variety of applications ranging from heavy-duty or high-strength construction applications to consumer products or medical applications such as cosmetic or tissue reconstruction applications. For example, the composite material can be adapted to form a construction material, a cosmetic formulation, a consumer product, a medical device or component, a coating, a filler, or a tissue engineering or reconstruction scaffold. In some embodiments, the composite material can be adapted to form a surgical tool for orthopedic applications. In some embodiments, the composite material can be adapted to form a bone scaffold material. In these embodiments, the bone scaffold material can comprise an osteoconductive agent, an osteoinductive agent, an osteogenic agent, or any combination thereof.

The composite material described herein can be adapted to be degradable or non-degradable, e.g., in order to suite the need of an application. By way of example only, in some embodiments, it is desirable to have a non-degradable composite material for use as a building construction material or a permanent implant. In other embodiments, a biodegradable composite material can be desirable in tissue engineering applications, e.g., for tissue repair and/or regeneration.

Silk Microfiber-Silk Composites:

In some embodiments, a composite material described comprises one or more silk microfibers distributed in a silk-based material or a silk fibroin-based material. At least one or a plurality of silk microfibers can be incorporated into a silk-based material in any form to form a silk microfiber-silk composite material for various applications, e.g., where high mechanical strength of the silk-based material is desirable. In some embodiments, at least one or a plurality of silk microfibers can be added into a silk solution for generation of a silk composite material in any form. See, e.g., U.S. Pat. Nos. 7,674,882; 7,842,780; 8,071,722 and 8,361,617 for examples of silk-based materials that can incorporate silk microfibers therein.

Additional examples of silk-based materials that can incorporate one or a plurality of silk microfibers (e.g., at least two or more silk microfibers) therein include, but are not limited to, a film (See, e.g., U.S. Pat. Nos. 7,674,882; and 8,071,722); a sheet (see, e.g., PCT/US13/24744 filed Feb. 5, 2013); a gel (see, e.g., U.S. Pat. No. 8,187,616; and U.S. Pat. App. Nos. US 2012/0070427; and US 2011/0171239); a mesh or a mat (see, e.g., International Pat. App. No. WO 2011/008842); a non-woven mat or fabric (see, e.g., International Pat. App. Nos. WO 2003/043486 and WO 2004/080346); a scaffold (see, e.g., U.S. Pat. Nos. 7,842,780; and 8,361,617); a tube (see, e.g., U.S. Pat. App. No. US 2012/0123519; International Pat. App. No. WO 2009/126689; and International Pat. App. Serial No. PCT/US13/30206 filed Mar. 11, 2013); a slab or block; a particle (see, e.g., U.S. Patent Application Nos. US 2010/0028451; and US 2012/0187591 for nanospheres and/or microspheres); a fiber (see, e.g., U.S. Pat. App. No. US 2012/0244143; a 3 dimensional construct (see, e.g., International Pat. App. No. WO 2012/145594, including, but not limited to, an implant, a screw, a plate); a high-density material; a porous material (see, e.g., U.S. Pat. Nos. 7,842,780; and 8,361,617); a coating (see, e.g., International Patent Application Nos. WO 2007/016524; WO 2012/145652); a magnetic-responsive material; a microneedle (see, e.g., International Patent Application No. WO 2012/054582); a machinable material (see, e.g., a U.S. Provisional Application entitled "Solvent-based process for the production of machinable silk medical device," naming Gabriel S. Perrone, Tim J. Lo, Berendien Jacoba Papenburg, Gary G. Leisk and David L. Kaplan as inventors, and filed on Apr. 5, 2013; U.S. applicaiton Ser. No. 61/808,768; or any combinations thereof. The contents of all the aforementioned patent applications are incorporated herein by reference.

In some embodiments, a plurality of silk microfibers can be incorporated into a silk-based material homogeneously or heterogeneously (e.g., in a gradient or as a coating on the surface of a silk-based material). See, e.g., US 2007/0212730 for methods that can be used to form a gradient of silk microfibers within a silk-based material.

In some embodiments, a plurality of silk microfibers distributed in a silk-based material can be oriented or aligned in a desirable or preferred direction. For example, in some embodiments, the silk microfibers present in a silk-based material can be oriented or aligned in a direction in order to increase the tensile strength of the composite material.

In some embodiments, the silk microfibers can be incorporated into a silk-based material (e.g., by adding silk microfibers to a silk solution) to generate a silk composite material for tissue engineering and/or wound healing applications. See, e.g., International Patent Application Nos. WO/2008/106485 entitled "Tissue engineered silk organs;" WO/2009/100280 entitled "3-dimensional silk hydroxyapatite compositions;" WO/2011/008842 entitled "Electrospun silk material systems for wound healing;" and International Application Serial Nos. PCT/US12/64471 filed Nov. 9, 2012, entitled "Injectable silk fibroin foams and uses thereof"; PCT/US12/64139 filed Nov. 8, 2012, entitled "A silk-based scaffold platform for engineering tissue constructs;" PCT/US13/24744 filed Feb. 5, 2013 entitled "Multi-layer biomaterial for tissue regeneration and wound healing;" and U.S. Ser. No. 13/702,606 entitled "Multilayered silk scaffolds for meniscus tissue engineering;" and U.S. Ser. No. 13/760,826 entitled "Implantable intervertebral disc devices and uses thereof;" and U.S. Provisional Patent Application No. 61/696,405 filed Sep. 4, 2012 entitled "Novel silk-calcium phosphate processing methods to fabricate porous calcium phosphate ceramics for bone tissue engineering." The contents of all the aforementioned patent applications are incorporated herein by reference.

In some embodiments, one or more silk microfibers can be incorporated into a silk solution for generation of a tubular structure, e.g., a stent (see, e.g., U.S. Pat. App. No. US 2012/0123519; International Pat. App. No. WO 2009/126689, the content of which is incorporated herein by reference).

In some embodiments, one or more silk microfibers can be incorporated into a silk solution for making a composite gel for treatment of cervical insufficiency. See, e.g., International Pat. App. No. WO 2013/044067, the content of which is incorporated herein by reference, for using a silk-based material for treatment of cervical insufficiency.

In some embodiments, one or more silk microfibers can be incorporated into a silk-based material for use in endovascular embolization of blood vessels as described in the International Pat. App. No. PCT/US13/28543 filed Mar. 1, 2013, the content of which is incorporated herein by reference.

Injectable Compositions:

In some embodiments, the composition described herein can be formulated as an injectable composition. In some embodiments, the injectable composition can be used for in vivo applications, e.g., soft tissue repair or augmentation. The term "injectable composition," when used in reference to in vivo application, generally refers to a composition that can be delivered or administered into a tissue with a minimally invasive procedure. The term "minimally invasive procedure" refers to a procedure that is carried out by entering a subject's body through the skin or through a body cavity or an anatomical opening, but with the smallest damage possible (e.g., a small incision, injection). In some embodiments, the injectable composition can be administered or delivered into a tissue by injection. In some embodiments, the injectable composition can be delivered into a tissue through a small incision on the skin followed by insertion of a needle, a cannula, and/or tubing, e.g., a catheter. Without wishing to be limited, the injectable composition can be administered or placed into a tissue by surgery, e.g., implantation.

The injectable compositions described herein can be used in a variety of medical uses, including, without limitation, fillers for tissue space, templates for tissue reconstruction or regeneration, scaffolds for cells in tissue engineering applications, or as a vehicle/carrier for drug delivery. A plurality of silk microfibers injected into a tissue to be repaired or augmented can act as a scaffold to mimic the extracellular matrices (ECM) of the body, and/or promote tissue regeneration. The silk microfiber scaffold can serve as both a physical support and/or an adhesive template for cells to proliferate therein. In some embodiments, the silk microfibers can be coated with cell attachment agents, e.g., collagen, and/or chemoattractants, e.g., growth factors, that can attract host cells to the silk microfibers and support the cell proliferation. In some embodiments, the silk microfibers can be seeded with cells prior to administration to a target tissue to be repaired or augmented.

In some embodiments, provided herein are injectable compositions that can be used to fill, volumize, and/or regenerate a tissue in need thereof. The injectable compositions can generally be used for tissue filling or volumizing, soft tissue augmentation, replacement, cosmetic enhancement and/or tissue repair in a subject. Additionally, the injectable compositions can be used for filling of any tissue void or indentation that are either naturally formed (e.g., aging) or created by surgical procedure for removal of tissue (e.g., a dermal cyst or a solid tumor), corticosteroid treatment, immunologic reaction resulting in lipoatrophy, tissue damage resulting from impact injuries or therapeutic treatment (e.g., radiotherapy or chemotherapy). The injectable compositions can also be used to raise scar depressions.

In certain embodiments, the injectable compositions can be used for soft tissue augmentation. As used herein, by the term "augmenting" or "augmentation" is meant increasing, filling in, restoring, enhancing or replacing a tissue. In some embodiments, the tissue can lose its elasticity, firmness, shape and/or volume. In some embodiments, the tissue can be partially or completely lost (e.g., removal of a tissue) or damaged. In those embodiments, the term "augmenting" or "augmentation" can also refer to decreasing, reducing or alleviating at least one symptom or defect in a tissue (for example, but not limited to, loss of elasticity, firmness, shape and/or volume in a tissue; presence of a void or an indentation in a tissue; loss of function in a tissue) by injecting into the tissue with at least one injectable composition described herein. In such embodiments, at least one symptom or defect in a tissue can be decreased, reduced or alleviated by at least about 30%, at least about 40%, at least about 50%, at least about 60%, at least about 70%, at least about 80% or higher, as compared to no treatment. In some embodiments, at least one symptom or defect in a tissue can be decreased, reduced or alleviated by at least about 90%, at least about 95%, at least about 97%, or higher, as compared to no treatment. In some embodiments, at least one symptom or defect in a tissue can be decreased, reduced or alleviated by 100% (defect-free or the defect is undetectable by one of skill in the art), as compared to no treatment. In other embodiments, the tissue can be augmented to prevent or delay the onset of defect manifestation in a tissue, e.g., loss of elasticity, firmness, shape and/or volume in a tissue, or signs of wrinkles. As used herein, the phrase "soft tissue augmentation" is generally used in reference to altering a soft tissue structure, including but not limited to, increasing, filling in, restoring, enhancing or replacing a tissue, e.g., to improve the cosmetic or aesthetic appearance of the soft tissue. For example, breast augmentation (also known as breast enlargement, mammoplasty enlargement, augmentation mammoplasty) alters the size and shape of a woman's breasts to improve the cosmetic or aesthetic appearance of the woman. Examples of soft tissue augmentation includes, but is not limited to, dermal tissue augmentation; filling of lines, folds, wrinkles, minor facial depressions, and cleft lips, especially in the face and neck; correction of minor deformities due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars; filling of nasolabial lines, nasoglabellar lines and intraoral lines. In some embodiments, the injectable compositions and/or silk microfibers described herein can be used to treat facial lipodystrophies. In some embodiments, the injectable compositions can be used for breast augmentation and/or reconstruction.

In some embodiments, the injectable compositions can be used for soft tissue repair. The term "repair" or "repairing" as used herein, with respect to a tissue, refers to any correction, reinforcement, reconditioning, remedy, regenerating, filling of a tissue that restores volume, shape and/or function of the tissue. In some embodiments "repair" includes full repair and partial repair. For example, the volume, shape and/or function of a tissue to be repaired can be restored by at least about 30%, at least about 40%, at least about 50%, at least about 60%, at least about 70%, at least about 80% or higher, as compared to no treatment. In some embodiments, the volume, shape and/or function of a tissue to be repaired can be restored by at least about 90%, at least about 95%, at least about 97%, or higher, as compared to no treatment. In some embodiments, the volume, shape and/or function of a tissue to be repaired can be restored by 100% (defect-free or the defect is undetectable by one of skill in the art), as compared to no treatment. In various embodiments, the injectable compositions can be used to repair any soft tissues discussed earlier, e.g., breast, skin, and any soft tissues amenable for soft tissue augmentation. In some embodiments, the term "repair" or "repairing" are used herein interchangeably with the term "regeneration" or "regenerate" when used in reference to tissue treatment.

In some embodiments, the injectable compositions can be used for soft tissue reconstruction. As used herein, the phrase "soft tissue reconstruction" refers to rebuilding a soft tissue structure that was severely damaged or lost, e.g., by a dramatic accident or surgical removal. For example, breast reconstruction is the rebuilding of a breast, usually in women. Conventional methods of construct a natural-looking breast generally involve using autologous tissue or prosthetic material. In some embodiments, such breast reconstruction can include reformation of a natural-looking areola and nipple, wherein such procedure can involve the use of implants or relocated flaps of the patient's own tissue. In some embodiments, administration of injectable compositions and/or silk microfibers into a soft tissue region to be reconstructed can maintain the shape and/or size of the reconstructed soft tissue structure for a period of time, e.g., at least 6 weeks, at least about 2 months, at least about 3 months or longer.

Without wishing to be bound, some embodiments of the injectable compositions can be used for hard tissue (musculoskeletal) augmentation or repair, such as augmentation or repair of bone, cartilage and ligament.

The injectable compositions and silk microfibers described herein can also be used for filling a tissue located at or near a prosthetic implant, for example, but not limited to, a conventional breast implant or knee replacement implant. In some embodiments, the injectable compositions and silk microfibers can be used to interface between a prosthetic implant and a tissue, e.g., to fill a void between the prosthetic implant and the tissue, and/or to prevent the tissue in direct contact with the prosthetic implant. By way of example only, after placing a prosthetic implant (e.g., a breast implant) in a subject, an injectable composition described herein can be introduced at or adjacent to the implant to fill any void between the implant and the tissue (e.g., breast tissue) and/or "sculpt" the tissue for a more natural look.

In some embodiments, the silk microfibers can be used alone, or in combination with silk fibroin particles described in the International Patent Application Serial No. PCT/US12/64450 filed Nov. 9, 2012 entitled "Injectable silk fibroin particles and uses thereof" for any of the purposes described therein, e.g., for soft tissue repair, augmentation and/or reconstruction.

Not only have the inventors shown that a composite material comprising silk microfibers distributed in a matrix material, e.g., a silk-based material, can provide significant improvement in compressive properties, as compared to other silk-silk composite materials previously described in Rajkhowa et al., 2010 and Gil et al., 2011; or other art-recognized biomaterials intended for bone tissue engineering, e.g., but not limited to, collagen, PCL, PLGA, chitosan, and/or gelatin, but the inventors have also shown that the silk microfiber-silk composite material can promote differentiation of human mesenchymal stem cells toward bone-like cells and further induce tissue ingrowth with vascularization upon implantation in vivo.

Methods for Repairing or Replacing a Diseased or Damaged Bone Tissue:

Accordingly, yet another aspect provided herein relates to a method of repairing or replacing a diseased or damaged bone tissue in a subject, which comprises placing at a target site of the diseased or damaged bone tissue a bone scaffold material comprising a composite material described herein, which comprises a plurality of silk microfibers distributed in a matrix material (e.g., a polymeric material and/or ceramic material). In some embodiments, the bone scaffold material can comprise silk microfiber-silk composite material, the silk microfiber-silk composite material comprising a plurality of silk microfibers distributed in a silk-based material.

In some embodiments, the bone scaffold material can further comprise an osteoconductive agent, an osteoinductive agent, an osteogenic agent, or any combinations thereof.

As used herein, the term "osteoconductive" generally refers to the ability of a material or agent to facilitate the migration of osteogenic cells to the surfaces of a scaffold through the fibrin clot established immediately after implantation the material. In some embodiments, the porosity of a bone scaffold material described herein can affect the osteoconductivity of the material.

As used herein, the term "osteoinductive" generally refers to the ability to induce non-differentiated stem cells or osteoprogenitor cells (osteoblasts), which is a component of osseous (bone) tissue, to differentiate into osteoblasts. The simplest test of osteoinductivity is the ability to induce the formation of bone in tissue locations such as muscle, which do not normally form bone (ectopic bone growth). It is generally understood that a bone scaffold material described herein can be made osteoinductive by adding growth factors such as rhBMP-2 (recombinant human bone morphogenic protein-2) to it. The mineralization and the addition of growth factors can affect the osteoinductivity of a bone scaffold material described herein.

As used herein, the term "osteogenic" generally refers to the ability of forming new bone after implantation or placement at a target site in vivo to be treated. Osteogenesis is the process of laying down new bone material using osteoblasts. Osteoblasts build bone by producing osteoid to form an osteoid matrix, which is composed mainly of Type I collagen. Osseous tissue comprises the osteoid matrix and minerals (mostly with calcium phosphate) that form the chemical arrangement termed calcium hydroxyapatite. Osteoblasts are typically responsible for mineralization of the osteoid matrix to form osseous tissue. Without wishing to be bound by a theory, the osteoconductivity and osteoinductivity of the bone scaffold material can have an impact on osteogenesis.

In some embodiments, the bone scaffold material can further comprise a cell (e.g., a bone cell or stem cell). As used herein, a bone cell is any cell that is found in bone. Bone cells include osteoblasts, osteocytes, osteoclasts, osteoprogenitors and bone lining cells. Osteoblasts are commonly called bone-forming cells. They secrete osteoid, which forms the bone matrix. They also begin mineralization. Osteocytes are mature osteoblasts which no longer secrete matrix, yet are surrounded by it. Osteocytes maintain metabolism, and participate in nutrient/waste exchange via blood. Osteoclasts function in resorption and degradation of existing bone, the opposite of osteoblasts. Osteoprogenitors are immature cells which differentiate to make osteoblasts. Bone lining cells are quiescent osteoblasts covering the bone. The cell can be added to the bone scaffold material described herein after formation by immersing the bone scaffold material in a solution comprising the biological cell or a cell culture. The bone cell can be autologous or allogenic.

In these embodiments, the bone scaffold material described herein can be used as a temporary, biodegradable support conduit for cell(s) to grow (e.g., native cells or exogenously-added cells) and replace with extracellular matrix, thus further improving biochemical properties over time.

Methods of Making Various Forms of Silk-Based Materials Comprising One or More Silk Microfibers To form a silk-based material comprising one or a plurality of silk microfibers from a silk fibroin solution, the silk fibroin solution can be prepared by any conventional method known to one skilled in the art. Generally, B. mori cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt is consequently removed using, for example, dialysis or chromatography.

In some embodiments, the resultant silk-based material can be soluble in an aqueous solution (e.g., water, a buffered solution, or a combination thereof). The inventors have previously discovered that properties (e.g., solubility) of the silk-based material can be altered using different time periods for degumming cocoons to provide degummed fibroin. Accordingly, in some embodiments, cocoons are boiled (e.g., in a salt solution such as $Na_2CO_3$) for a period of about 1 minute to 2 hours, about 5 minutes to about 2 hours, or about 10 minutes to about 60 minutes. In some embodiments, the cocoons can be boiled (e.g., in a salt solution such as $Na_2CO_3$) for about 10 minutes, about 20 minutes, about 30 minutes, about 45 minutes, or about 60 minutes. By controlling the degumming time, the solubility/degradation of the resultant silk-based material (e.g., in an aqueous solution) can be optimized. Without wishing to be bound by theory, longer boiling time generally yields silk fibroin of lower molecular weight (MW)/chain length, and thus a silk-based material produced from lower MW silk fibroin can is generally more soluble (e.g., in an aqueous solution) than the one produced from higher MW silk fibroin.

After degumming cocoons and solubilizing dried silk fibroin, if necessary, the solution can then be concentrated using, for example, dialysis against a hygroscopic polymer, for example, PEG, a polyethylene oxide, amylose or sericin. Preferably, the PEG is of a molecular weight of 8,000-10,000 g/mol and has a concentration of 10-50%. A slide-a-lyzer dialysis cassette (e.g., Pierce, MW CO 3500) is used. However, any dialysis system may be used. The dialysis is for a time period sufficient to result in a final concentration of a desirable aqueous silk solution (e.g., between 10-50%, or 10-30%). In most cases dialysis for 2-12 hours is sufficient. See, for example, PCT application PCT/US/04/11199, content of which is incorporated herein by reference.

Alternatively, the silk fibroin solution can be produced using organic solvents. Such methods have been described, for example, in Li, M., et al., J. Appl. Poly Sci. 2001, 79, 2192-2199; Min, S., et al. Sen'I Gakkaishi 1997, 54, 85-92; Nazarov, R. et al., Biomacromolecules 2004 May-June; 5(3):718-26. Exemplary organic solvents that can be used to produce the silk solution include, but are not limited to, hexafluoroisopropanol (HFIP). See, for example, International Application No. WO2004/000915, content of which is incorporated herein by reference.

Silk fibroin solution for forming the silk-based materials of the disclosure can have any desired silk fibroin concentration, e.g., a silk fibroin concentration of from about 0.25% to about 50% (w/v) or from about 0.5% to about 15% (w/v), or from about 0.5% to about 10% (w/v). In some embodiments, the silk fibroin solution has a silk fibroin concentration of from about 10% to about 40% or from 15% to about 35% (w/v). In one embodiment, the silk fibroin solution has a silk fibroin concentration of from about 20% to about 30% (w/v). In one embodiment, the silk fibroin solution has a silk fibroin concentration of about 30% (w/v). In some embodiments, the silk fibroin solution has a silk fibroin concentration of about 0.1% to about 30% (w/v), about 0.5% to about 15% (w/v), about 1% to about 8% (w/v), or about 1.5% to about 5% (w/v). In some embodiments, the silk fibroin solution has a silk fibroin concentration of about 5% to about 30% (w/v), about 10% to about 25% (w/v), or about 15 to about 20% (w/v).

The silk microfibers described herein can be added into a silk fibroin solution prior to forming a silk-based material. In some embodiments, silk microfibers can be added to a silk solution at a weight ratio (silk microfibers:silk fibroin in a solution) of about 100:1 to about 1:100, about 75:1 to about 1:75, about 50:1 to about 1:50; or about 25:1 to about 1:25. In some embodiments, silk microfibers can be added to a silk solution at a weight ratio (silk microfibers:silk fibroin in a solution) of about 1:1 to about 1:100; about 1:1 to about 1:75; about 1:1 to about 1:50, about 1:1 to about 1:25; about 1:1 to about 1:10, or about 1:1: to about 1:5.

Methods for producing different formats of the silk-based materials are known in the art, including, e.g., but not limited to drying, solution casting, salt leaching, freeze-drying, gas forming, electrospinning, gelling, fiber drawing, coating, spraying, micronizing, or any combination thereof. In some embodiments, the drying can comprise lyophilization and/or air-drying.

The silk-based material can be in any form, shape or size. For example, the silk-based material can be a solution, a paste, a fiber, a film, a sheet, a fiber, a mat, a non-woven mat, a mesh, a fabric, a sponge, a foam, a gel, a hydrogel, a tube, a particle (e.g., a nano- or micro-particle, a gel-like particle), a powder, a scaffold, a 3D construct, a coating layer on a substrate, a microneedle, or any combinations thereof.

In some embodiments, the silk-based material in any form, shape or size described herein can be reduced to particles or powders, if desired. In these embodiments, silk microfibers can be blended with silk particles or powders, e.g., in a composition described herein.

In some embodiments, the silk-based material comprising one or more silk microfibers is in the form of a fiber. As used herein, the term "fiber" means a relatively flexible, unit of matter having a high ratio of length to width across its cross-sectional perpendicular to its length. Methods for preparing silk fibroin fibers are well known in the art. A fiber can be prepared by electrospinning a silk solution, drawing a silk solution, and the like. Electrospun silk materials, such as fibers, and methods for preparing the same are described, for example in WO2011/008842, content of which is incorporated herein by reference in its entirety. Without limitations, the silk microfibers can be distributed in the silk fibroin matrix of the fiber, present on a surface of the fiber, or any combination thereof.

In some embodiments, the silk-based material comprising one or more silk microfibers can be in the form of a film, e.g., a silk film. As used herein, the term "film" refers to a flat or tubular flexible structure. It is to be noted that the term "film" is used in a generic sense to include a web, film, sheet, laminate, or the like. In some embodiments, the film is a patterned film, e.g., nanopatterned film. Exemplary methods for preparing silk fibroin films are described in, for example, WO 2004/000915 and WO 2005/012606, content of both of which is incorporated herein by reference in its entirety. Without limitations, the silk microfibers can be distributed in the film, present on a surface of the film, coated by the film, or any combination thereof.

The film can have any desired thickness. For example, the film thickness can range from about 1 nm to about 10 mm. In some embodiments, the film has a thickness in the range of from about 1 nm to about 1000 nm or from about 1 μm to about 1000 μm.

In some embodiments, the silk-based material comprising one or more silk microfibers can be in the form of a silk particle, e.g., a silk nanosphere or a silk microsphere. As used herein, the term "particle" includes spheres; rods; shells; and prisms; and these particles can be part of a network or an aggregate. Without limitations, the particle can have any size from nm to millimeters. As used herein, the term "microparticle" refers to a particle having a particle size of about 1 μm to about 1000 μm. As used herein, the term "nanoparticle" refers to particle having a particle size of about 0.1 nm to about 1000 nm. In some embodiments, the silk particle does not encompass a silk fiber.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In some embodiments, the silk-based material comprising one or more silk microfibers can be in the form of a foam or a sponge. Methods for preparing silk foams or sponges are well known in the art. In some embodiments, the foam or sponge is a patterned foam or sponge, e.g., nanopatterned foam or sponge. Exemplary methods for preparing silk foams and sponges are described in, for example, WO 2004/000915, WO 2004/000255, and WO 2005/012606, content of all of which is incorporated herein by reference in its entirety. Without limitations, the silk microfibers can be distributed in the silk fibroin matrix of the foam or sponge, absorbed on a surface of the foam or sponge, present in a pore of the foam or sponge, or any combination thereof.

In some embodiments, the silk-based material can be in the form of a gel or hydrogel. The term "hydrogel" is used herein to mean a silk-based material which exhibits the ability to swell in water and to retain a significant portion of water within its structure without dissolution. Methods for preparing silk gels and hydrogels are well known in the art. Exemplary methods for preparing silk gels and hydrogels are described in, for example, WO 2005/012606, content of which is incorporated herein by reference in its entirety. Without limitations, the silk microfibers can be distributed in the silk fibroin matrix of gel or hydrogel, absorbed on a surface of the gel or hydrogel or sponge, present in a pore of the gel or hydrogel, or any combination thereof.

In some embodiments, the silk-based material comprising one or more silk microfibers can be in the form of a cylindrical matrix, e.g., a silk tube. The silk microfibers can be present in the lumen of the cylindrical matrix and/or dispersed in a wall of the cylindrical matrix. The silk tubes can be made using any method known in the art. For example, tubes can be made using molding, dipping, electrospinning, gel spinning, and the like. Gel spinning is described in Lovett et al. (Biomaterials, 29(35):4650-4657 (2008)) and the construction of gel-spun silk tubes is described in PCT application no. PCT/US2009/039870, filed Apr. 8, 2009, content of both of which is incorporated herein by reference in their entirety. Construction of silk tubes using the dip-coating method is described in PCT application no. PCT/US2008/072742, filed Aug. 11, 2008, content of which is incorporated herein by reference in its entirety. Construction of silk tubes using the film-spinning method is described in PCT application No. PCT/US2013/030206, filed Mar. 11, 2013 and U.S. Provisional application No. 61/613,185, filed Mar. 20, 2012. Without wishing to be bound by a theory, it is believed that the inner and outer diameter of the silk tube can be controlled more readily using film-spinning or gel-spinning than dip-coating technique.

In some embodiments, the silk-based material can be porous. For example, the silk-based material can have a porosity of at least about 10%, at least about 20%, at least about 30%, at least about 40%, at least about 50%, at least about 60%, at least about 70%, at least about 80%, at least about 90%, or higher. Without wishing to be bound by theory, in some embodiments, porosity of the silk-based material can be controlled for desired dissolution rate. For example, higher porosity of the silk-based material can generally allow an aqueous solution to permeate into the silk-based material faster and thus accelerate the process of dissolution. One of skill in the art can adjust the porosity accordingly, based on a number of factors such as, but not limited to, desired dissolution rates; molecular size and/or diffusion coefficient of the component present in the silk-based material, and/or concentrations, amounts of silk fibroin in the silk-based material, and/or desired physical or mechanical properties of the silk-based material. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous silk-based material can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the pores of the silk-based material can have a size distribution ranging from about 50 nm to about 1000 µm, from about 250 nm to about 500 µm, from about 500 nm to about 250 µm, from about 1 µm to about 200 µm, from about 10 µm to about 150 µm, or from about 50 µm to about 100 µm. In some embodiments, the silk-based material can be swellable when hydrated. The sizes of the pores can then change depending on the water content in the silk-based material. In some embodiment, the pores can be filled with a fluid such as water or air.

Methods for forming pores in a silk-based material are known in the art and include, but are not limited, porogen-leaching methods (e.g., salt leaching), freeze-drying methods, and/or gas-forming method. Exemplary methods for forming pores in a silk-based material are described, for example, in U.S. Pat. App. Pub. Nos.: US 2010/0279112 and US 2010/0279112; U.S. Pat. No. 7,842,780; and WO2004062697, content of all of which is incorporated herein by reference in its entirety.

Though not meant to be bound by a theory, silk-based material porosity, structure and mechanical properties can be controlled via different post-treatment processes such as vapor annealing, heat treatment, alcohol treatment, air-drying, lyophilization and the like. Additionally, any desirable degradation rates of a silk-based material can be controlled by varying processing parameters, such as silk-based material thickness, silk molecular weight, concentration of silk in the silk-based material, beta-sheet conformation structures, silk II beta-sheet crystallinity, or porosity and pore sizes.

For incorporating at least one additive in a silk-based material, the additive can be included in a silk fibroin solution used for producing the silk-based material. Alternatively, or in addition, a preformed silk-based material can be added to a solution comprising the additive(s) and letting the additive(s) absorb in/on the silk-based material.

In some embodiments, the additive(s) can be distributed, homogenously or non-homogenously (e.g., in a gradient) in the silk-based material. In some embodiments, the additive(s) can be encapsulated or entrapped by silk fibroin in the silk-based material. In some embodiments, the additive(s) can be mixed or blended with silk fibroin in the silk-based material.

The silk fibroin for making the silk-based materials can be modified for different applications or desired mechanical or chemical properties of the matrix. One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein.

After forming the silk-based material, the material can be treated, e.g., to provide a desired properties. In some embodiments, the silk-based material can be treated by annealing as described earlier. Methods of annealing a silk-based material include, but are not limited to, lyophilization or freeze-drying, gas-drying, alcohol immersion (e.g., ethanol, methanol), water annealing, water vapor annealing heat annealing, shear stress, ultrasound (e.g., by sonication), pH reduction (e.g., pH titration and/or exposing a silk-based material, e.g., a silk microfiber, to an electric field), and any combinations thereof.

Regardless of the annealing method employed, the end result of the annealing process is that annealed silk fibroin has high degree of crystallinity such that it becomes more insoluble. In some embodiments, "high degrees of crystallinity" refers to beta sheet contents of between about 20% and about 70%, e.g., about 20%, about 25%, about 30%, about 35%, about 40%, about 45%, about 50%, about 55%, about 60%, about 65% and about 75%.

In some embodiments, the annealing process can provide a silk-based material can comprising a silk II beta-sheet crystallinity content of at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk-based material can have a silk II beta-sheet crystallinity of 100%.

An Exemplary Method of Making Silk Microfiber-Silk Composite Materials

In some embodiments, methods of making silk microfiber-silk composite materials are provided herein. In general, a silk microfiber-silk composite material can be produced by mixing a desired amount of silk microfibers into a silk solution prior to inducing beta sheet formation to form a solid-state composite material.

In one embodiment, silk microfiber-silk scaffolds can be prepared by modifying the methods for preparing HFIP-based silk scaffolds described in Gil E S. et al. (24). A desired ratio (e.g., 1:1 or 1:3 (w/w %)) of HFIP-silk:silk-fiber composite scaffolds can be fabricated to comprise 25% w/v HFIP-silk solution and silk fibers of larger (about 400-about 500 μm), medium (about 150-about 200 μm) and smaller (about 10-about 20 μm) diameters obtained by the hydrolysis method described herein. Briefly, ~4 g of NaCl (particle size 800 um) can be sieved for each scaffold. Based on the microfiber ratio used for reinforcement, each silk microfiber type can be weighed (e.g. for 1:1 ratio, weigh 0.25 g silk fibers for 1 ml of 25% w/v HFIP silk). For scaffold fabrication, silk microfibers can be hydrated in water and then excess water can be removed followed by the addition of ~4 g of NaCl with gentle mixing. The fiber-salt mixture can then poured into a glass tube of 10 mm diameter and the mixture can be allowed to settle to the bottom with gentle tapping. Water can be removed from the fiber-salt mixture by lyophilization. The height of the dry fiber-salt composite can be measured and 1 ml of silk/HFIP solution (25 wt %) per cm height is added and then covered. The system can be centrifuged at 4,000 rpm for 5 min. Repeated centrifugation can be used if required to completely distribute the HFIP-silk solution to all parts of the dry fiber-salt mixture.

The materials can be allowed to settle for 1 hr and the cover is then removed to leave the tubes for 3-4 days in a fume hood to allow the HFIP to evaporate. Finally, 70% methanol can be added to the tubes and then covered for 2 days.

To perform salt leaching, the covers can be removed and the scaffolds can be placed in a beaker of water (2-3 L) with gentle stirring for 3-4 days until all of the salt can be removed. To remove the salt, the scaffolds can be removed from the glass tubes, e.g., with a spatula, and placed in a beaker with water (2-3 L) with slow stirring until all remaining salt is dissolved. Once the salt is removed, the scaffolds can be transferred to 70% ethanol and stored.

An exemplary method of preparing HFIP-silk (hexafluoroisopropanol) is described below, which encompasses preparation of degummed silk fibers, and silk solution from degummed silk fibers, followed by dissolving silk in HFIP.

Preparation of Degummed Silk Fibers from Cocoons:
1. Cut dried cocoons with scissors into 4 pieces.
2. Prepare 2 separate glass beakers filled with 3 L water each and heat it up until boiling.
3. Weigh sodium carbonate to be added to the beaker with 3 L water (each) to make 0.02 (M) 3 L solution.
4. Add sodium carbonate to the beakers when water starts to boil and let it dissolve.
5. Put the cocoon pieces in the boiling water with 0.02 (M) sodium carbonate, and stir.
6. Boil for 10 minutes with occasional stirring.
7. After 10 min of boiling, carefully transfer the silk fibers from the first beaker to the second beaker with 0.02 (M) sodium carbonate.
8. Boil for another for 10 min with occasional stirring.
9. Take the degummed fibers out of the beaker and rinse with cold water (5-7 washes) until all sodium carbonate is removed.
10. Squeeze the silk with hands to remove excess water.
11. Put in fume/chemical hood to air dry for at least 12 hours.

Preparation of Silk Solution from Degummed Silk Fibers:
1. Prepare 50 ml of 9.3 (M) solution of Lithium Bromide (LiBr) in a glass beaker.
2. Cover the LiBr solution with aluminum foil and keep beaker in the oven at 60 C for 10 min.
3. Weigh 10 μm of degummed silk fibers and add to LiBr solution. Mix gently to cover the fibers with solution to help faster dissolution.
4. Keep fiber with LiBr solution in oven for 1 hr and allow it to completely dissolve. It becomes a clear solution when completely dissolved.
5. After silk fibers dissolves, perform dialysis to remove LiBr.
6. Take one 4 L beaker and fill with distilled water till 3 L mark.

7. Pour silk solution using syringe into cassettes (12 kDa) and put them back into beaker for dialysis.
8. Changes water with fresh distilled water every 1 hr for the next 4 hrs. Then changes water every 6-8 hrs for another 3-4 times.
9. After dialysis take out silk solution from cassette into a clean glass beaker.
10. Centrifuge at 5000 rpm for 5 mins.
11. Pour silk into fresh 50 m falcons and freeze at −80° C. for overnight.
12. Lyophilize the frozen silk to get dry silk sponge.

Preparation HFIP Dissolved Silk:

1. To prepare 10 ml of 25 wt % silk solutions weigh 2.5 μm of lyophilized silk sponge.
2. Add the 2.5 μm silk sponge to 10 ml of HFIP solution in a small glass container. Make sure the sponge is wet with HFIP solution.
3. Close the lid and keep the container in chemical hood for overnight to dissolve silk.

Fabrication of Reinforced Fiber Scaffolds:

Any ratios of HFIP-silk: silk-fiber can be used in the reinforced composite. In some embodiments, a ratio of 1:1 or 1:3 HFIP-silk:silk-fiber can be used in the reinforced composite 1. Weight 4 μm of salt of 800 μm size grain size (use a sieve to collect similar sized grains).
2. Based on the fiber ratio to be used for reinforcement, weigh amount of silk fibers i.e. large, medium and small (e.g. for 1:1 ratio, weigh 0.25 μm silk powder for 1 ml of 25% HFIP silk).
3. Make the fibers wet by adding water to it. Remove excess water.
4. Add 4 μm of salts to the wet fibers and mix gently with a spatula to disperse the fibers homogeneously.
5. Pour the silk/salt mix into small glass tubes. The diameter of the tubes can be selected based on required scaffold diameter.
6. Allow the fiber-salt mixture to settle to the bottom. Tap the tube gently if required.
7. Dry the fiber-salt mixture in a lyophilizer until water evaporates and completely dry.
8. Measure the height of the dry fiber-salt composite. Add 1 ml of silk/HFIP solution per cm of the composite scaffold (i.e. height of dry fiber-salt within the glass tubes) and put the lid on.
9. Centrifuge at 4000 rpm for 5 min.
10. Repeat steps 9 if required to completely spread and distribute silk solution to all parts of the dry fiber-salt mixture.
11. Remove the lids and leave the tubes in the chemical hood for HFIP to evaporate for 3-4 days.
12. Add 70% methanol to the tubes and close the lid. The scaffolds should be submerged in methanol for 2 days.
13. To perform salt leaching, remove the lids and place the scaffolds with tubes in beaker full of water (2-3 L) for 3-4 days until salt is removed.
14. To further remove any remaining salt, gently take the scaffold out of the glass tubes and put them in a big beaker with water (2-3 L) and slowly stirring condition until salt is dissolved.
15. Once salt is removed, transfer scaffolds to 70% ethanol and store until required.

Silk Fibroin

As used herein, the term "fibroin" includes silkworm fibroin and insect or spider silk protein (Lucas et al., Adv. Protein Chem 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use according to the present disclosure can be obtained from a solution containing a genetically engineered silk, such as from bacteria, yeast, mammalian cells, transgenic animals or transgenic plants. See, for example, WO 97/08315 and U.S. Pat. No. 5,245,012, content of both of which is incorporated herein by reference.

In some embodiments, silk fibroin from *Bombyx mori* can be used herein due to its desirable properties including biocompatibility with low inflammatory and immunogenic responses (27, 28, 33-37). The unique β-sheet (crystalline)-rich structure imparts high stiffness and toughness to silk biomaterials, making it a useful biopolymer for bone engineering applications (35). Previous reports show ultimate tensile strength (UTS) values between 610-690 MPa for silk filaments, compared to 0.9-7.4 MPa for rat tail type I collagen and 28-50 MPa for polylactic acid (PLA), respectively (35). Similarly, a modulus between 15 and 17 GPa for silk was reported and compared to 0.0018-0.046 GPa, for collagen, and 1.2-3.0 GPa for PLA (35). Silk has achieved FDA approval for some medical devices. Additionally, due to the amphiphilic features, post processing of silk into various material formats including films, scaffolds, fibers, hydrogels and sponges is feasible with tunable degradation properties for biomaterial and tissue engineering applications (33, 34, 38).

Additives

In some embodiments, the composition or composite material described herein can further comprise one or more additives. In some embodiments, the composite material can comprise a plurality of silk microfibers distributed in a silk-based material, which can be prepared from a fibroin solution comprising one or more (e.g., one, two, three, four, five or more) additives. Without wishing to be bound by theory, additive(s) can be selected to provide a silk-based material with desired properties, e.g., provide flexibility, solubility, ease of processing, enhanced stability of at least one property of the component, and the like.

Without limitations, an additive can be selected from cells; biopolymers; ceramic materials; plasticizers; nanoparticles (e.g., gold nanoparticles); therapeutic agents; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; enzymes; an extract made from biological materials such as bacteria, plants, fungi, or animal cells; animal tissues; naturally occurring or synthetic compositions; and any combinations thereof. Total amount of additives in the silk-based material or in the composition described herein can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the silk-based material or the composition. One of skill in the art can determine appropriate ratio of the silk fibroin to the additive, e.g., by measuring the property of the component or the silk-based material that is affected by the addition of the additive at various ratios described herein.

In some embodiments, an additive is a biocompatible polymer (or biopolymer). Exemplary biocompatible polymers or biopolymers include, but are not limited to, a polylactic acid (PLA), poly-glycolic acid (PGA), polylactide-co-glycolide (PLGA), polyesters, poly(ortho ester), poly(phosphazine), polyphosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described, for example, in U.S. Pat. No. 6,302,848; No. 6,395,734; No. 6,127,143; No. 5,263,992; No. 6,379,690; No. 5,015,476; No. 4,806,355; No. 6,372,244; No. 6,310,188; No. 5,093,489; U.S. Pat. No. 387,413; No. 6,325,810; No. 6,337,198; U.S. Pat. No. 6,267,776; No. 5,576,881; No. 6,245,537; No. 5,902,800; and No. 5,270,419, content of all of which is incorporated herein by reference.

In one embodiment, the additive is glycerol, which can affect the flexibility and/or solubility of the silk-based. Silk-based materials, e.g., silk films comprising glycerol are described in WO 2010/042798, content of which is incorporated herein by reference in its entirety.

In some embodiments, an additive is a cell or a biological cell. Mammalian cells include, without limitation; primate, human and a cell from any animal of interest, including without limitation; mouse, hamster, rabbit, dog, cat, avian, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, cancer cells, progenitor cells, immune cells, blood cells, fetal cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, bone tissue, musculoskeletal, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy. In some embodiments, the cell can be a diseased cell.

Examples of other additives include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-1, and the like.

Embodiments of Various Aspects Described Herein can be Defined in any of the Following Numbered Paragraphs:

1. A method of producing a silk microfiber of a desired length comprising contacting a degummed silk fiber with an alkaline solution.
2. The method of paragraph 1, wherein said contacting is maintained for a duration sufficient for hydrolysis of the degummed silk fiber into a plurality of silk microfibers.
3. The method of paragraph 1 or 2, wherein the length of the silk microfibers is controlled by concentration of the alkaline solution, the duration of hydrolysis, hydrolysis temperature, or any combinations thereof.
4. The method of any of paragraphs 1-3, wherein the length of the silk microfibers ranges from about 1 μm to about 2 mm.
5. The method of any of paragraphs 1-4, wherein the length of the silk microfibers ranges from about 10 μm to about 1000 μm.
6. The method of any of paragraphs 1-5, wherein the alkaline solution comprises a strong basic solution.
7. The method of paragraph 6, wherein the strong basic solution comprises sodium hydroxide, potassium hydroxide, lithium hydroxide, rubidium hydroxide, cesium hydroxide, calcium hydroxide, strontium hydroxide, barium hydroxide, or any combinations thereof
8. The method of any of paragraphs 1-7, wherein the alkaline solution comprises sodium hydroxide.
9. The method of any of paragraphs 1-8, wherein the alkaline solution is a concentrated alkaline solution.
10. The method of any of paragraphs 1-9, wherein the alkaline solution has a concentration of about 0.1 M to about 30 M.
11. The method of any of paragraphs 2-10, wherein the duration of hydrolysis ranges from about 5 seconds to about 5 hours.
12. The method of any of paragraphs 2-11, wherein the duration of hydrolysis ranges from about 5 seconds to about 500 seconds.
13. The method of any of paragraphs 2-12, wherein the hydrolysis is performed at about 4° C. to about 100° C.
14. The method of any of paragraphs 2-13, wherein the hydrolysis is performed at about room temperature to about 100° C.
15. The method of any of paragraphs 1-14, further comprising neutralizing the mixture comprising one or more silk microfibers and the alkaline solution.
16. The method of any of paragraphs 1-15, further comprising annealing the silk microfibers.
17. The method of paragraph 16, wherein said annealing the silk microfibers comprises lyophilization, gas-drying, solvent immersion, water annealing, water vapor annealing, heat annealing, shear stress, ultrasound (e.g., by sonication), pH reduction (e.g., pH titration and/or exposing a silk microfiber to an electric field), or any combination thereof.
18. The method of any of paragraphs 1-17, further comprising separating a subset of the silk microfibers of the desired length from the plurality of silk microfibers.
19. A silk microfiber produced by the method of any of paragraphs 1-18.
20. The silk microfiber of paragraph 19, wherein the silk microfiber is degradable.
21. The silk microfiber of paragraph 19, wherein the silk microfiber is non-degradable.
22. A composition comprising a silk microfiber of any of paragraphs 19-21.

23. The composition of paragraph 22, wherein the composition is an injectable composition.
24. The composition of paragraph 22 or 23, wherein the composition is a construction material, a cosmetic formulation, a consumer product, a medical device or component, a coating, a filler, or a tissue engineering or reconstruction scaffold.
25. The composition of any of paragraphs 22-24, further comprising an additive.
26. The composition of paragraph 25, wherein the additive is selected from the group consisting of cells; biopolymers; ceramic materials; plasticizers; nanoparticles (e.g., gold nanoparticles); therapeutic agents; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; enzymes; an extract made from biological materials such as bacteria, plants, fungi, or animal cells; animal tissues; naturally occurring or synthetic compositions; and any combinations thereof.
27. The composition of any of paragraphs 22-26, wherein the composition is in a form selected from a group consisting of a film, a sheet, a gel, a mesh, a mat, a non-woven mat, a fabric, a scaffold, a tube, a slab or block, a particle, a fiber, a 3-dimensional construct, an implant, a high-density material, a porous material, a reinforced material, a non-porous material, a machinable material, a magnetic responsive material, a microneedle, and any combinations thereof.
28. A composite material comprising silk microfibers distributed in a polymeric material.
29. The composite material of paragraph 28, wherein the polymeric material is a silk-based material.
30. The composite material of paragraph 28 or 29, wherein the silk microfibers have a length ranging from about 1 µm to about 4 mm.
31. The composite material of any of paragraphs 28-30, wherein the silk microfibers have a length ranging from about 5 µm to about 1000 µm, or about 10 µm to about 700 µm.
32. The composite material of any of paragraphs 28-31, wherein the composite material has a compressive modulus of at least about 3 MPa or higher in its hydrated state.
33. The composite material of any of paragraphs 28-32, wherein the polymeric material and silk microfibers are present in a weight ratio of about 100:1 to about 1:100.
34. The composite material of any of paragraphs 28-33, wherein the polymeric material and silk microfibers are present in a weight ratio of about 1:1 to about 1:20.
35. The composite material of any of paragraphs 28-34, wherein the polymeric material is non-porous.
36. The composite material of any of paragraphs 28-35, wherein the polymeric material is porous.
37. The composite material of paragraph 36, wherein pores of the polymeric material do not have a smooth surface wall.
38. The composite material of any of paragraphs 28-37, wherein the composite material is in a form selected from the group consisting of a film, a sheet, a gel, a mesh, a mat, a non-woven mat, a fabric, a scaffold, a tube, a slab or block, a particle, a fiber, a 3-dimensional construct, an implant, a high-density material, a porous material, a reinforced material, a non-porous material, a machinable material, a magnetic responsive material, a microneedle, and any combinations thereof.
39. The composite material of any of paragraphs 28-38, wherein the polymeric material comprises an additive.
40. The composite material of paragraph 39, wherein the additive is selected from the group consisting of cells; biopolymers; ceramic materials; plasticizers; nanoparticles (e.g., gold nanoparticles); therapeutic agents; small organic or inorganic molecules; saccharides; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; enzymes; an extract made from biological materials such as bacteria, plants, fungi, or animal cells; animal tissues; naturally occurring or synthetic compositions; and any combinations thereof.
41. The composite material of any of paragraphs 28-40, wherein at least a portion of the composite material is degradable.
42. The composite material of any of paragraphs 28-41, wherein at least a portion of the composite material is non-degradable.
43. The composite material of any of paragraphs 28-42, wherein the composite material is adapted to form a construction material, a cosmetic formulation, a consumer product, a medical device or component, a coating, a filler, or a tissue engineering or reconstruction scaffold.
44. The composite material of any of paragraphs 28-43, wherein the composite material is adapted to form a surgical tool for orthopedic applications.
45. The composite material of any of paragraphs 28-43, wherein the composite material is adapted to form a bone scaffold material.
46. The composite material of paragraph 45, wherein the bone scaffold material comprises an osteoconductive agent, an osteoinductive agent, an osteogenic agent, or any combination thereof.
47. A method of repairing or replacing a diseased or damaged bone tissue in a subject comprising placing at a target site of the diseased or damaged bone tissue a bone scaffold material of paragraph 45.
48. The method of paragraph 47, wherein the bone scaffold material further comprises an osteoconductive agent, an osteoinductive agent, an osteogenic agent, or any combinations thereof
49. The method of any of paragraphs 47-48, wherein the bone scaffold material further comprises a cell.
50. The method of paragraph 49, wherein the cell is a bone cell or a stem cell.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "enhanced" is used herein to generally mean an increase by a statically significant amount; for the avoidance of any doubt, the term "enhanced" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. With respect to enhanced mechanical property of a composite material comprising silk microfibers, a reference level refers to a material without silk microfibers.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. Exemplary Materials and Methods Used for Fabrication and Characterization of Silk Microfiber-Reinforced Silk Protein Scaffolds, e.g., for Bone Repair Previous reports on reinforcing silk particles (fabricated by milling) into a silk matrix have indicated improved scaffolds for bone applications with compressive properties in hydrated state of ~3 MPa, improving the ingrowth of hMSC's in vitro towards forming bone-like tissues (24-26). However, the compressive strength of those scaffolds with reinforcing silk particles is much lower (e.g., at least 25% lower) than that of the reinforced scaffolds with silk fibers, e.g., obtained from alkaline hydrolysis described herein.

Currently, bone graft/scaffold engineering using silk biomaterials has received increasing interest as an alternative option (24, 25, 27, 28). However, towards this goal several biological parameters need to be met including biocompatibility, biodegradability, surface roughness, porosity, osteoconductivity and above all high mechanical integrity (4, 24, 25). A tissue engineered bone scaffold from a biomaterial that is biocompatible as well as functional in load bearing applications offers important options in this regard. However, many challenges remain to satisfy an optimally functional bone regeneration scaffold system (29). Perhaps the largest challenge is the need for polymer biomaterials to meet the high compressive properties of bone, a prerequisite to function in vivo (24, 25, 30-32). In some embodiments, provided herein are methods to improve the compressive properties of silk scaffolds to match the requirements for bone. An exemplary approach is to use silk microfiber as reinforcements, as a step towards orthopedic biomaterials for repairs. To produce silk microfiber, a new silk hydrolysis method has been developed to fabricate micron sized silk fibers as fillers with a silk matrix for reinforcement.

Silk Fiber and Solution Preparation.

Silk solution was prepared using *Bombyx mori* silkworm cocoons supplied by Tajima Shoji Co (Yokohama, Japan) according to protocols described in our previous studies (39). Briefly, cut pieces of cocoons were degummed in boiling 0.02M sodium carbonate solution for 20 min followed by thorough washing in deionized water and air drying. After air drying, the silk fibers were divided into two batches where one batch was used for alkali hydrolysis using sodium hydroxide (St. Louis, Mo., USA). The second batch of degummed silk fibers was dissolved in 9.3 M LiBr solution (St. Louis, Mo., USA) at 60° C. yielding a 20% w/v solution. This solution was subsequently dialyzed against water using Slide a-Lyzer dialysis cassettes (Pierce, MWCO 3,500) for three days with frequent change of water. The final concentration of the aqueous silk fibroin solution was about 8% w/v. Part of the silk solution was frozen at −80° C. and then lyophilized. The lyophilized silk sponge was added to hexafluoroisopropanol (HFIP) (St. Louis, Mo., USA) to prepare 25% w/v solvent-based silk solution.

Hydrolysis of Degummed Silk into Micron Range Fibers.

The microfiber preparation process (FIG. 1A) can be divided into three stages: (a) preparation of degummed silk fibers from cocoons, (b) hydrolysis of degummed silk fibers into micron sized fibers (termed as microfibers herein); and (c) washing/neutralization of the microfibers and lyophilization.

Degumming of Silk Fibers from Coccons:

The method is similar to the above description for silk fiber/solution preparation.

Hydrolysis of Degummed Silk Fibers:

Sodium hydroxide pellets (NaOH) weighing ~3.5 µm (to obtain ~17.5 M solution) were added to 5 ml of distilled water. When approximately 70% of the NaOH pellets are dissolved with an exothermic reaction, the dried degummed silk fibers weighing 0.35 µm were added and stirred, e.g., with a spatula.

Washing/Neutralization of Microfibers:

To stop hydrolysis, ~45 ml of water is added to the reaction mixture and centrifuged at 3,500 rpm for 5 minutes. The supernatant is discarded and the microfibers are resuspended in 50 ml of water, stirred and centrifuged. This step can be repeated between 5 and 8 times or more, to remove any remaining alkali. The pH of the solution is measured and the pH is adjusted to ~7.0 using hydrochloric acid. The neutralized microfiber solution is again centrifuged at 3,500 rpm for ~5 minutes and resuspended in water (repeated about 3-5 times). Finally the microfibers are suspended in PBS and lyophilized to generate a silk microfiber powder. To obtain large (about 400-about 500 µm long) and medium (about 150-about 200 µm long) silk microfibers, the hydrolysis reaction was carried for 30 and 180 seconds, respectively. To obtain very fine/smaller (about 10-about 20 µm long) silk microfibers, the reaction mixture was set up in a boiling water bath for 60 sec to aid rapid hydrolysis.

Fabrication of Reinforced Microfiber-HFIP Scaffolds.

Silk microfiber reinforced-HFIP scaffolds were prepared by modifying the methods for preparing HFIP-based silk scaffolds described in Gil E S. et al. (24). Two different ratios of 1:1 and 1:3 (w/w %) of HFIP-silk:silk-microfiber composite scaffolds were fabricated comprised of 25% w/v HFIP-silk solution and silk microfibers of larger (about 400-about 500 µm), medium (about 150-about 200 µm) and smaller (about 10-about 20 µm) diameters obtained by the hydrolysis method described. About 4 g of NaCl (particle size 800 µm) was sieved for each scaffold. Based on the microfiber ratio used for reinforcement, each silk microfiber type was weighed (e.g., for 1:1 ratio, weigh 0.25 g silk fibers for 1 ml of 25% w/v HFIP silk). For scaffold fabrication, silk microfibers are hydrated in water and then excess water was removed followed by the addition of ~4 g of NaCl with gentle mixing. The microfiber-salt mixture was then poured into a glass tube of ~10 mm diameter and the mixture was allowed to settle to the bottom with gentle tapping. Water was removed from the microfiber-salt mixture by lyophilization. The height of the dry microfiber-salt composite was measured and ~1 ml of silk/HFIP solution (25 wt %) per cm height was added and then covered. The system was centrifuged at 4,000 rpm for 5 min. Repeated centrifugation was used if required to completely distribute the HFIP-silk solution to all parts of the dry microfiber-salt mixture. The materials were allowed to settle for 1 hr and the cover was then removed to leave the tubes for 3-4 days in a fume hood to allow the HFIP to evaporate. Finally, 70% methanol was added to the tubes and then covered for 2 days. To perform salt leaching, the covers were removed and the scaffolds were placed in a beaker of water (2-3 L) with gentle stirring for 3-4 days until all of the salt was removed. To remove the salt, the scaffolds were removed from the glass tubes, e.g., with a spatula, and placed in a beaker with water (2-3 L) with slow stirring until all remaining salt was dissolved. Once the salt was removed, the scaffolds were transferred to 70% ethanol and stored. For control scaffolds, 25% w/v HFIP-silk solution was poured into 4 g of salt in a glass tube without silk microfibers.

Scanning Electron Microscopy (SEM).

Fractured sections of the silk scaffolds were obtained in liquid nitrogen using a razor blade. The fracture surfaces were sputter coated with Pt/Pd and morphology was examined with a Field Emission Scanning Electron Microscope (FESEM) Zeiss Ultra55 or Supra55VP (Carl Zeiss AG, Germany). Pore size and wall thickness of silk scaffolds were analyzed with ImageJ 1.40 (Wayne Rasband).

Porosity Measurement by Liquid Displacement.

Porosity of the microfiber reinforced-HFIP scaffolds was determined via liquid displacement with hexane, as previously reported in Mandal et al. (40). After fabrication, the scaffolds were lyophilized and then immersed in a graduated cylinder of known volume of hexane ($V_1$). A series of quick evacuation-depressurization cycles were performed to completely evacuate entrapped air and to impregnate the scaffold with hexane; thereafter, the volume in the cylinder was recorded ($V_2$). The hexane impregnated scaffold was removed and the volume was recorded again ($V_3$). Any change of volume due to evaporation during the evacuation cycles was checked using another cylinder without the scaffold. The porosity of the scaffold is expressed as:

$$\text{Porosity} = [(V_1 - V_3)/(V_2 - V_3)] \times 100\%$$

Mechanical properties. Unconfined compressive mechanical testing of hydrated silk microfiber reinforced-HFIP scaffolds was performed on an Instron 3366 (Norwood, Mass., USA) testing frame equipped with a 0.1 kN load cell. Tests for all scaffold types both unseeded and cell-seeded were carried out in 0.1 (M) PBS bath (Biopuls, Instron Corp.) at 37° C. under hydrated conditions. Separate silk scaffold discs were punched out for compressive tests, with dimensions of 4 mm diameter and 3 mm height. For cell-seeded silk scaffolds, each type was individually seeded with $10^6$ hMSCs at day 1 and cultured for 28 days in osteogenic medium. All tests were accessed with a conventional open-sided (nonconfined) configuration and were performed using a displacement control mode at a rate of 5 mm/min following ASTM standard D1621-04a (Standard Test Method for Compressive Properties of Rigid Cellular Plastics). After the compression tests, the compressive stress and strain were graphed based on the measured cross-sectional area and sample height (nominal ~4-5 mm, measured automatically at 0.02N tare load), respectively. The elastic modulus was calculated based on a linear regression fitting of the small strain section that preceded an identifiable plateau region.

Isolation of Human MSCs (hMSCs).

Human bone marrow-derived mesenchymal stem cell (hMSC) isolation and expansion was carried out using the protocols described in Park et al. (41). A 25 ml bone marrow aspirate (Lonza, Walkersville, Md.) was obtained from a 27 year old male donor and was diluted in 75 ml of PBS. Cells were separated by density gradient centrifugation and 20 ml aliquots of the bone marrow suspension were overlaid onto a poly-sucrose gradient (1077 g/cm$^3$, Histopaque, Sigma) and centrifuged at 800 g for 30 min at room temperature. The cell pellet was resuspended in Eagle's Minimum Essential Medium (α-MEM: Gibco BRL, Grand Island, N.Y.) supplemented with 10% fetal bovine serum (FBS, Gibco BRL), 100 U/mL penicillin G (Gibco BRL), and 100 µg/mL streptomycin (Gibco BRL). Cell number and viability were determined using a trypan blue exclusion test. The resuspended cells were plated at a density of $1.5 \times 10^5$ cells/cm$^2$ and placed in a 5% $CO_2$ incubator at 37° C. The culture medium was changed every other day and cells were passaged three times (P3) before use.

Cell Proliferation and Osteogenic Differentiation on Silk Scaffolds.

Osteogenic potential of silk microfiber reinforced-HFIP scaffolds were evaluated by differentiation of hMSCs in osteogenic media. Approximately, $10^6$ cells were seeded onto each reinforced silk microfiber scaffold of dimension 3×2 mm per group of 4 (n=4) followed by addition of growth medium (DMEM+10% FBS+antibiotics) after initial cell attachment. Seeded hMSCs were cultured for 3 days at 37° C. and 5% $CO_2$ before transferring into osteogenic media comprising DMEM supplemented with 10% FBS, 0.1 mM nonessential amino acids, 50 µg/mL ascorbic acid-2-phosphate (St. Louis, Mo., USA), 100 nM dexamethasone (St. Louis, Mo., USA), 10 mM β-glycerolphosphate (St. Louis, Mo., USA) in the presence of 100 U/mL penicillin, 100 µg/mL streptomycin, and 0.25 µg/mL Fungizone. Cultures were maintained at 37° C. in a humidified incubator supplemented with 5% $CO_2$. Half of the medium was changed every two days. Scaffold discs were removed for analysis after four weeks. hMSC proliferation on 3D silk-scaffold constructs were monitored by Alamar blue dye reduction assay (Invitrogen, USA) after 1, 7, 14, 21 and 28 days following the manufacturers' protocol.

Real-Time PCR.

Reinforced silk microfiber scaffolds with cells (n=4 per group) were transferred into 2-mL plastic tubes, then 1.0 mL of Trizol was added. Scaffolds were chopped into pieces with microscissors on ice. The tubes were centrifuged at 12,000 g for 10 min, after which the supernatant was transferred to a new tube. Chloroform (200 mL) was added to the solution and incubated for 5 min at room temperature. Tubes were then centrifuged at 12,000 g for 15 min, and the upper aqueous phase was transferred to a new tube. One volume of 70% ethanol (v/v) was added and applied to an RNeasy mini spin column (Qiagen, Hilden, Germany). The RNA was washed and eluted according to the manufacturer's protocol. The RNA samples were reverse transcribed into cDNA using oligo (dT)-selection according to the manufacturer's protocol (High Capacity cDNA Archive Kit, Applied Biosystems, Foster City, Calif.). Collagen type Ia1 (ColIa1), ALP, bone sialoprotein (BSP), and osteopontin (OP) were quantified using the M 3000 Real Time PCR system (Stratagene, La Jolla, Calif.) for osteogenesis. PCR reaction conditions were 2 min at 50° C., 10 min at 95° C., and then 50 cycles at 95° C. for 15 s/60° C. for 1 min. All data were normalized to the expression of the housekeeping gene, glyceraldehyde-3-phosphate-dehydrogenase (GAPDH). The GAPDH probe was labeled at the 50 end with fluorescent dye VIC and with the quencher dye TAMRA at the 30 end. Probes for human glyceraldehyde-3-phosphate-dehydrogenase (GAPDH, # Hs99999905_m1), collagen type Iα (Col Iα1, # Hs00164004_m1), alkaline phosphatase (ALP, # Hs00758162_m1), bone sialoprotein (BSP, # Hs00173720_m1) and osteopontin (OP, # Hs00167093_m1) were purchased as Assay-on-Demand Products (Applied Biosciences, Foster City, Calif.).

Biochemical Analysis.

For each study group, DNA content and alkaline phosphatase (ALP) activity were analyzed using scaffolds chopped with microscissors on ice. Crushed samples (n=4) were extracted twice with 0.2% (v/v) Triton X-100/5 mM $MgCl_2$ solution. DNA content was measured using the PicoGreen assay (Molecular Probes, Eugene, Oreg.), according to the manufacturer's protocol. Samples were measured fluorometrically at an excitation wavelength of 480 nm and an emission wavelength of 528 nm. Alkaline phosphatase (ALP) activity was assessed on the same samples using a biochemical assay from Stanbio Laboratory (Boerne, Tex.) based on conversion of p-nitrophenyl phosphate to p-nitrophenol, measured spectrophotometrically at 405 nm. ALP activity was normalized by DNA content of the sample.

In Vivo Subcutaneous Implantation in Mice.

All procedures were conducted under animal care protocols approved by Tufts Institutional Animal Care and Use Committee. All animals used in this study were five to seven weeks old balb/c female mice (Charles River breeding labs). The mice were distributed by three experimental groups each with two time points: 7 days and 4 weeks. The mice were randomly assigned to the experimental groups and silk microfiber reinforced-HFIP scaffold samples were subcutaneously implanted in lateral subcutaneous pockets of each mouse under general anesthesia using a mixture of oxygen (0.6 l/min) and 1.5-3 vol % of Isofluran. The healing process at the incision region was coarsely monitored during all study period and no deaths were registered during the experiment. To assess inflammatory responses, mice were euthanized by CO exposure after 7 day and 4 weeks post-implantation and samples collected along with the overlying tissue for histological examination.

Histology.

Histological sections of individual scaffold types were examined to assess the extent of degradation and for local inflammatory responses at the implant-host interface, such as for neovascularisation, fibrosis and the presence of inflammatory cells. After collection, samples were immediately immersed in 10% neutral buffered formalin for 24 h before histological analysis. Samples were processed through a series of graded ethanol, embedded in paraffin, and sectioned at 5-7 µm thickness. For histological evaluation, sections were deparaffinized, rehydrated and stained with hematoxylin and eosin (H&E).

Statistical Analysis.

All quantitative experiments were performed at least in triplicate (unless specified), and results are expressed as mean±standard deviation. Statistical analysis of data was performed by one-way analysis of variance (ANOVA). Differences between groups of *$p \le 0.05$ were considered statistically significant and **$p \le 0.01$ as highly significant.

Example 2. Evaluation of Silk Fiber and Reinforced Scaffolds

Figure 1B:
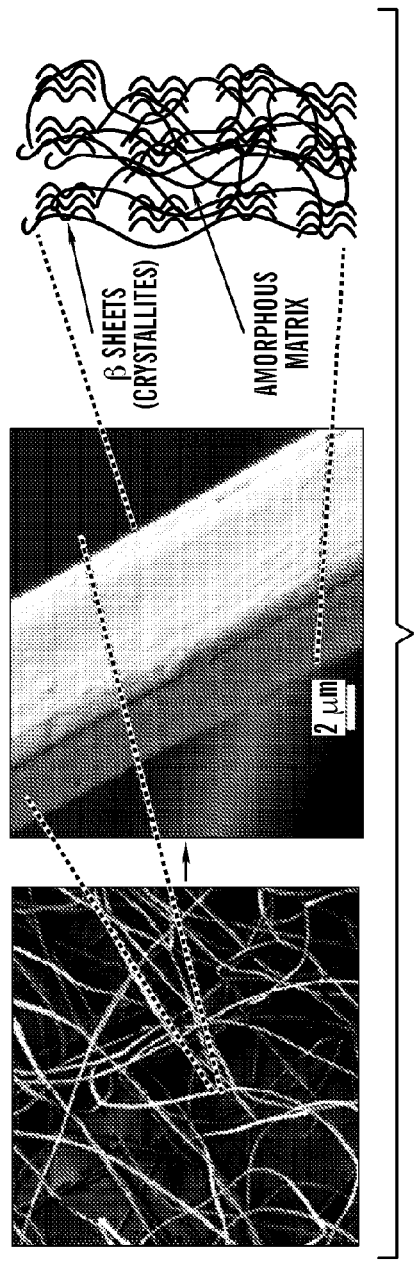
Figure 1C:
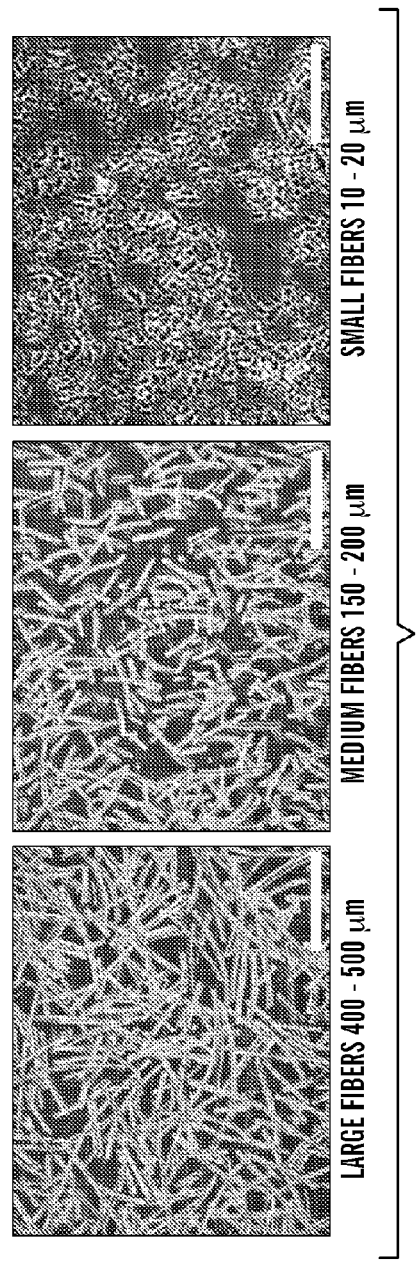

The inventors have discovered that subjecting silk (as a protein) to alkali hydrolysis results in generation of the cleaved silk microfibers (FIG. 1C). The length of silk microfibers was inversely proportional to time of hydrolysis (FIG. 2A). Further, hydrolysis was faster with random chopping during the initial 0-15 s but later the rate of hydrolysis was steady over time. After the initial 15 s, the average microfiber length obtained was 354±84 µm, which dropped to 263±67 µm and 191±46 µm after 50 and 70 s, respectively (FIG. 2A). Upon external addition of heat, e.g., setting the reaction in a boiling water bath, faster hydrolysis resulted (within 60 s) and yielding much smaller microfibers of 10±5 µm size. During the course of hydrolysis microfiber diameter was determined to remain within a range of 10±2 µm except for hydrolysis with external heating where the microfibers were fragmented to various smaller sizes (FIG. 1C).

To fabricate the microfiber reinforced silk scaffolds, 25 wt % HFIP silk solution was blended with equal amounts (1:1, HFIP:silk microfiber) or three times more microfibers by wt % (1:3, HFIP:silk fiber). Similarly, HFIP-silk alone (25 wt %) was used to fabricate control scaffolds (without microfibers). In each ratio, three different types of reinforced scaffolds were fabricated using microfibers of larger (400-500 µm), medium (150-200 µm) and smaller (10-20 µm) lengths (FIG. 1C). By external appearance, the 1:1 scaffolds were more porous than the 1:3 ratio (FIG. 4). The 1:3 ratio scaffolds were rougher in appearance compared to the 1:1 scaffolds. Porosity as calculated by the liquid (hexane) displacement method was approximately 88±9%, 82±11% and 77±8% for the reinforced scaffolds with larger, medium and smaller microfibers, respectively, and the 1:1 ratio. For the 1:3 ratio, the scaffold porosities decreased to 81±8%, 73±10%, and 69±7% for the larger, medium and smaller microfibers, respectively. In comparison, control HFIP-silk scaffolds showed the highest porosity of 90±13%. SEM images indicated strong bonding between the reinforced silk microfibers with HFIP-silk based on the absence of any phase separation (FIG. 4). All microfiber scaffolds, as well as the controls, had interconnected pores averaging 500-600 µm. In comparison to control scaffolds with smoother pores, all microfiber reinforced scaffolds showed rougher surfaces with bonded microfibers forming a dense composite (FIG. 4). The control scaffolds had thicker walls between pores in comparison to the microfiber scaffolds, which had open-ended highly porous walls as from SEM. The 1:3 ratio systems appeared more compact when compared to the 1:1 ratio, possibly due to the higher amounts (wt %) of added microfibers. The wall thickness and porosity can be tuned by varying silk microfiber content, where wall thickness increased with higher silk microfiber content, demonstrating the role of total silk in impacting thickness either in solution or microfiber form (FIG. 4).

Example 3. Evaluation of Biomechanics of Silk Microfiber Reinforced Scaffolds

Figure 2B:
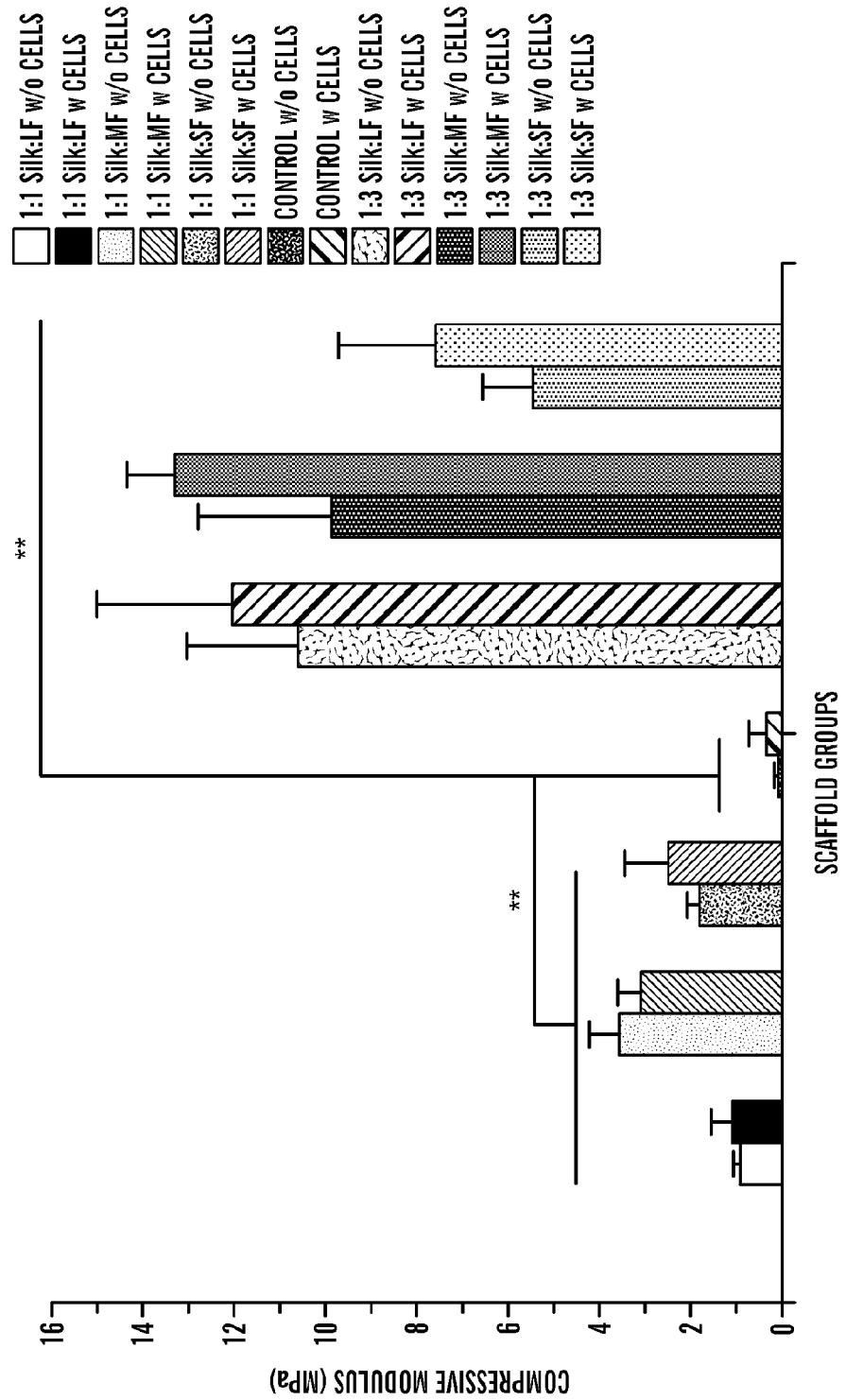

Silk microfiber reinforced HFIP scaffolds showed high compressive modulus compared to the control HFIP silk scaffolds in fully hydrated conditions for both ratios (1:1 and 1:3) of blending. For acellular scaffolds, 1:3 ratios were 4-5 times the modulus when compared to the 1:1 scaffolds (FIG. 2B). Due to higher microfiber density in the 1:3 ratio, the modulus of the scaffolds with larger microfibers increased from 0.90±0.11 to 10.64±2.46 MPa ($p \leq 0.01$). Similarly for scaffolds containing the medium and small microfibers, the values were enhanced from 3.62±0.65 and 1.86±0.21 to 9.79±3.05 and 5.42±1.18 MPa, respectively ($p \leq 0.01$). An approximate increase of 9.70, 6.10 and 3.50 MPa, respectively, for scaffolds reinforced with large, medium and small microfibers (FIG. 2B). In comparison, control HFIP-silk scaffolds showed a low modulus of 85.06±32.62 KPa (**$p \leq 0.01$). A value 100 times lower than the lowest value observed for the 1:1 large microfiber-reinforced scaffolds. Surprisingly, the modulus for the scaffolds with the large microfibers was increased upon addition of a higher microfiber density and was comparable to that of the scaffolds with medium sized fibers at a ratio of 1:3 in comparison to 1:1 (FIG. 2B). Following one month of hMSC growth under osteogenic conditions, an enhancement in compressive modulus was observed (FIG. 2B). Although a moderate enhancement of modulus was observed for the 1:1 ratios, in contrast the 1:3 scaffolds showed significantly higher values. A maximum of 13.30±1.03 MPa (increase of ~26%) compressive modulus was observed for the scaffolds with medium sized microfibers, followed by 12.06±3.81 (~12% increase) and 7.62±2.15 MPa (~29% increase) for the scaffolds with large and smaller microfibers, respectively.

Example 4. Human Bone Marrow Stem Cell Proliferation and Osteogenesis in Silk Microfiber Reinforced Scaffolds hMSCs when seeded onto silk scaffolds (both control and silk microfiber reinforced systems) responded well with enhanced cell survival rate. As compared to day 0 (seeding day), cells proliferated with time (FIG. 3B). From plotted normalized values, proliferation rate was steady after week one and two, possibly due to induction of osteogenesis within the scaffolds. Cell proliferation (normalized) was highest within the scaffolds in the control HFIP-silk scaffolds followed by the reinforced scaffolds with larger and medium microfibers, then lowest in case of smaller microfibers (FIG. 3B). In comparison to the controls, at the end of week four, the scaffolds with smaller microfibers showed ~15% fewer cells followed by ~4% and ~8% in the case of the larger and medium sized microfiber scaffolds, respectively.

Figure 3A:
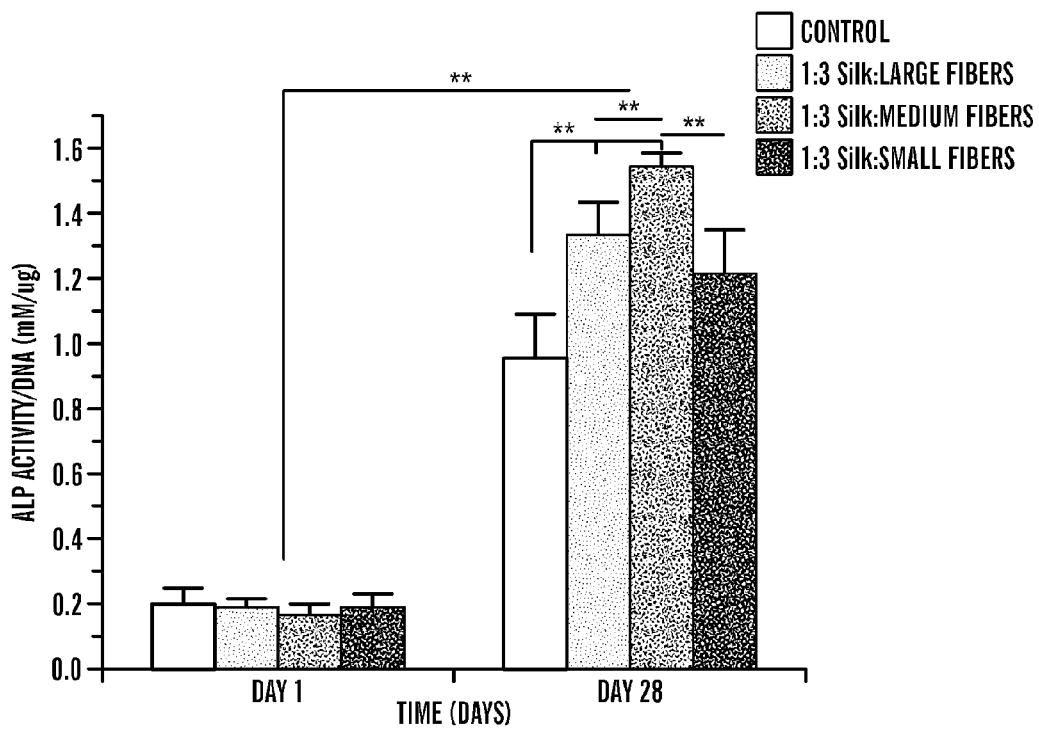
FIGS. 3A-3B show in vitro data for culturing hMSCs cells in silk microfiber reinforced scaffolds.
Figure 3B:
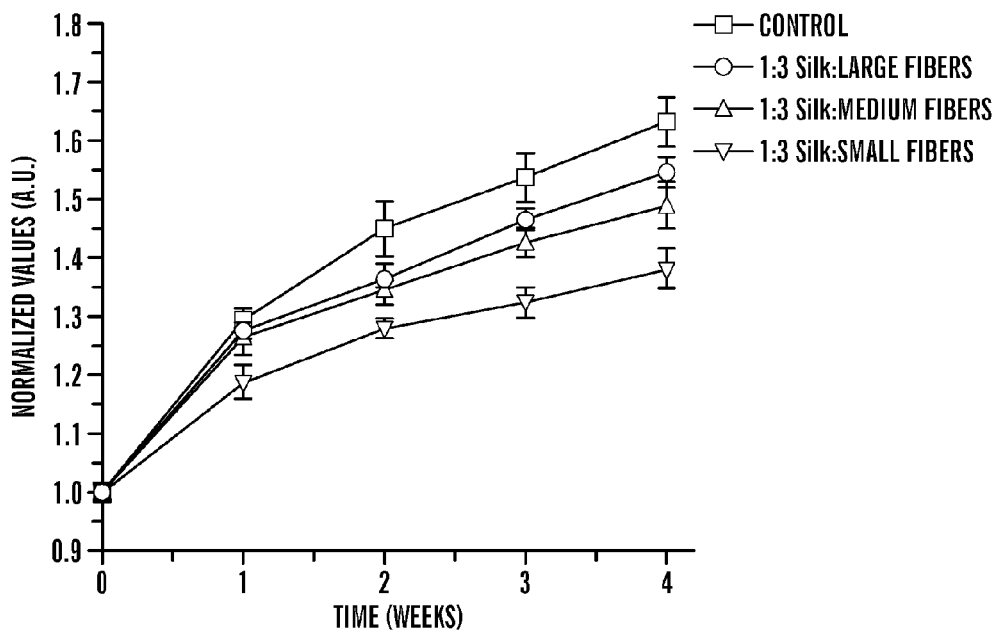

Osteogenic differentiation of hMSCs seeded onto silk-microfiber scaffolds was evaluated by biochemical assay and gene expression (FIG. 3A, and FIGS. 5A-5D). ALP activity as a marker for early ectoblastic differentiation displayed higher activity on day 28 as compared to day 1 of cell seeding (FIG. 3A). In comparison to controls, the microfiber reinforced scaffolds showed significantly high ALP activity at the end of day 28 ($p \leq 0.01$). Further, amongst the microfiber reinforced scaffolds, ALP activity was highest in scaffolds with medium sized microfibers, followed by the larger and smaller microfibers ($p \leq 0.01$) (FIG. 3A). Further to confirm osteogenesis, transcript levels of osteogenic markers such as ALP, OP, BSP along with collagen (Colla1) were analyzed by real time PCR after day 28 of culture (FIGS. 5A-5D). For all genes, on day 28 transcript levels were significantly higher when compared to day 1, including controls ($p \leq 0.01$). ALP activity increased nearly 20-30-fold, including controls, when compared to day 1, with highest expression measured in the case of scaffolds with the medium sized microfibers, followed by larger and smaller microfibers, respectively ($p \leq 0.01$). In the case of Colla1, gene expression increased by 6-9-fold after day 28 with microfiber reinforced scaffolds showing significantly higher values when compared to controls ($p \leq 0.01$). Similarly for OP and BSP, significantly higher gene expression was observed with 6-9- and 4-6-fold increases, respectively, at the end of the culture period ($p \leq 0.01$). For both OP and BSP, reinforced scaffolds showed higher expression when compared to control HFIP scaffolds (**$p \leq 0.01$).

Figure 6:
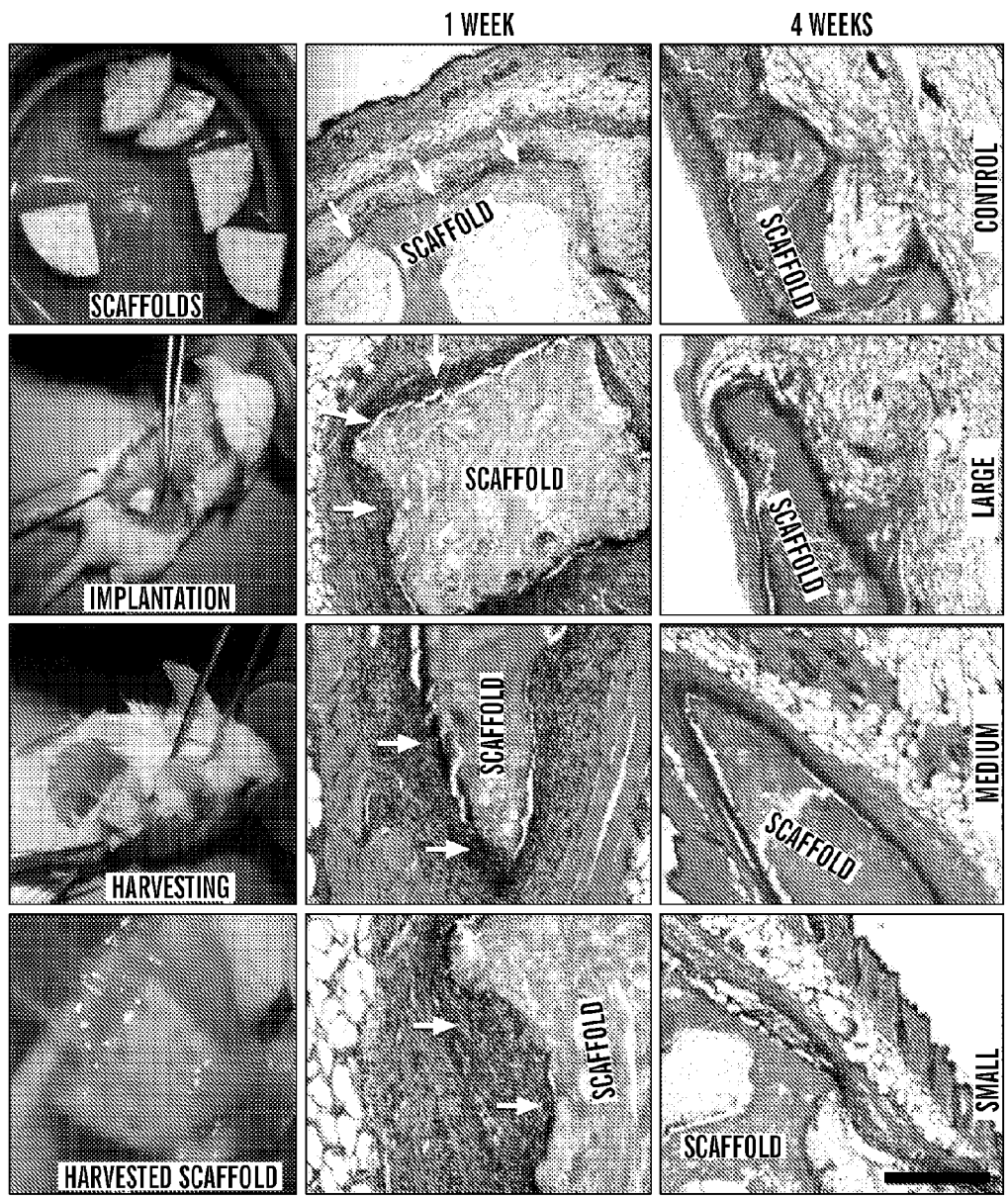
FIG. 6 is a set of histological images showing in vivo immunological response of fabricated silk microfiber scaffolds in mice. Samples sections were stained with H&E. Microscopic images (left panel) show scaffolds implanted subcutaneously in mice and a harvested highly vascularized implant after 4 weeks.

Example 5. In Vivo Responses: Implantation of Silk Microfiber Reinforced Scaffolds To evaluate material immune response and implant integration, the fabricated scaffolds (both silk microfiber-reinforced scaffolds and controls) were implanted into mice subcutaneously at the back of mice and were retrieved after 1 and 4 weeks (FIG. 6). Following retrieval of scaffolds after week 1 and H&E staining, immune cells (marked with arrows) were observed surrounding the implanted scaffolds of all types, a sign of milder, more indolent tissue reaction and a more compact zone of repair. On close examination, the number of immune cells (mainly macrophages) surrounding control, larger and medium microfiber scaffolds were comparatively less compared to the scaffolds with the smaller microfiber-reinforced scaffolds (FIG. 6). Medium microfiber scaffolds showed intermittent numbers of immune cells. The layer of macrophages and fibroblasts were 4-5 cell sheets thick and the macrophages were restricted to the immediate host-implant interface. The interface layer was superimposed by oriented fibroblasts, rare lymphocytes, and devoid of giant cells. However, around the scaffolds with the smaller microfibers higher numbers of macrophages, plasma cells and increased vascularization was present at the rougher surface areas of the scaffolds. The layer of macrophages, fibroblasts and plasma cells was 8-12 cell sheets thick (FIG. 6). Silk degradation was not visibly observed over the time frame of study. Following a 4 week study, the retrieved scaffold samples showed fewer inflammatory cells surrounding the implants in all scaffold samples including the scaffolds with the smaller microfibers, with close integration of the implants and mice tissue. Further, during harvesting of the implants at week 4, dense tissue ingrowth with vascularization surrounding the implants was observed (FIG. 6).

Discussion

Previous studies both in vitro and in vivo using porous silk scaffolds have shown potential towards reconstruction of bone and bone-related grafts due to the intrinsic high mechanical strength and robustness (27, 28, 33, 34, 38, 42). However, greater strength was desired to match bone requirements, thus newer strategies is needed to reduce bone graft failures and also to provide an alternate option of using scaffolds as direct load bearing supports to improve in vivo tissue engineering outcomes. To progress towards this goal of high strength silk scaffolds, a simpler method to achieve micron range fibers from degummed silk fibers by alkali hydrolysis was identified. Subsequently, these different sized silk microfibers were used to reinforce silk scaffolds, with the added benefit of the ability to control microfiber size and particle loading to evaluate impact on mechanical properties towards bone tissue engineering. Further, as these are silk-silk composites, compatibility between the microfiber and bulk silk phases is inherently optimized, permitting maximal benefit in material mechanical properties of the composite silk systems.

Micron silk particle fabrication using ball milling and or jet milling has been reported for the fabrication of particle reinforced scaffolds (26, 43, 44). However, in comparison to methods described herein, the alkali hydrolysis method is faster (seconds), cost effective (in comparison to expensive instruments needed for milling) and can be tuned for various desired properties, such as fiber length, mechanical properties of the reinforced scaffold, and cell response to the reinforced scaffold (FIGS. 1A-1C, 2A-2B, 3A-3B).

While alkaline hydrolysis of proteins is known, silk has never been used in alkaline hydrolysis. More importantly, there is no existing process for generating microfibers from native silk fibers, where the size of the microfibers can be modulated and controlled by adjusting the process parameters. The alkali (sodium hydroxide) initiates hydrolysis of amide bonds by conversion to a carboxylic acid and an amine or ammonia. What is particularly surprising is the stepwise decrease in silk microfiber length, perhaps accounted for due to the specific arrangement of the beta-sheets (crystallites) and less crystalline regions within the silk structure (45). It is speculated that that there is a sequential hydrolysis of silk regions more prone to the reaction, such as the noncrystalline domains. Some amino acids of silk (e.g., arginine (1% in silk) and serine (13% in silk) are destroyed in the process, while others are racemized (46). This is further supported by the rapid exothermic hydrolysis reaction resulting in smaller microfibers in the 1,000 µm range within 5-10 s (FIG. 2A). Similarly, slowing down the hydrolysis process as observed from the microfiber sizes obtained after the initial 15-20 s can be attributed to cleaving the more crystalline regions of the silk, due to the stronger hydrogen bonding, resulting in finer fibers (150-300 µm fibers between 50-720 s) (FIG. 1B, and FIG. 2A). Further, upon supply of external heat (energy to break the bonds) faster hydrolysis was observed, presumably due to rapid cleaving of both less crystalline and crystalline silk regions (45). In approximately 60 s, microfibers ranging 10-20 µm were obtained as compared to 100 µm plus size fibers after 720 s of normal reaction without external heating (FIG. 2A). This slight modification allowed us to fabricate a wider range of microfiber sizes of which three different groups, ~10-20, ~150-200 and ~400-500 µm, were selected and designated as small, medium and large microfibers, respectively, for the silk microfiber-scaffold reinforcement studies described herein (FIG. 1C).

Strong interfacial contact between blended polymers within a composite is critical for achieving higher stiffness (24, 47). Silk was chosen as the common material for both the phases (fiber and bulk matrix) to achieve enhanced interfacial protein-protein compatibility as evident from the SEM images. FIG. 4 shows no evidence of phase separation, demonstrating miscibility of silk microfibers with the silk matrix towards a strong composite via optimal interfacial contact (47). Comparing SEM images, it is evident that the overall surface roughness, including the roughness of pore walls and interconnectivity, increased for both ratios of 1:1 and 1:3 upon the addition of larger microfibers when compared to smaller microfibers, with an average pore size in the range of 500-600 microns (FIG. 4). Medium microfibers showed an intermediate roughness while smaller microfibers had a more compact structure with less fibrous solid walls (FIG. 4). Bonded silk microfibers can be seen intertwined throughout the scaffold making the surface rough and porous with good miscibility (24). This is an added advantage for these new composite scaffolds as interconnected porous structures are important for new bone tissue regeneration, allowing integration via adequate neovascularization and nutrient/metabolic waste diffusion (29, 42, 48). Further, using salt leaching, control over the range of pore sizes and geometry can be attained by choosing the appropriate salt grain size (in this study 800 um grains were used) to mimic bone features related to distinct anatomical bone sites (49-51).

High mechanical stability is a prerequisite for load bearing biomedical implants, especially for bone tissue engineering to withstand high compressive in vivo stresses. Although silk in its natural fiber form is considered a ductile and stiff polymer, its post processing and fabrication steps determine scaffold mechanical properties. In order to achieve high compressive properties, silk microfibers were used as fillers along with a bulk silk matrix to achieve high strength composite scaffolds. Use of reinforcing fillers has been previously used in engineering to enhance composite strength and has been reported for silk (24, 26, 52, 53). However, none of these studies teaches or suggests use of silk microfibers as reinforcing fillers to produce a high strength silk microfiber reinforced scaffold as described herein. Due to the strong protein-protein cohesive bonding, higher compressive modulus values were achieved in microfiber bonded scaffolds (acellular) when compared to control HFIP-silk scaffolds (50-100-fold increase) (FIG. 2B). Surprisingly, differences in compressive properties were observed with the different sized microfibers as well as the change silk microfiber content (FIG. 2B). Higher microfiber amounts (1:1 vs 1:3 ratios) led to greater packing density, yielding stronger composites with higher mechanical properties (24, 26). However, using a similar microfiber content (1:3 ratio), comparable high compressive values were obtained for scaffolds with the larger and medium fibers, in the range of ~10 MPa in the hydrated state (these values represent the strongest silk scaffolds to date), possibly due to the improved bonding of microfibers to the matrix as observed from SEM (FIG. 4). Further, these longer microfibers can possibly help to bind better to the silk matrix by partial dissolution in the presence of HFIP (24). This in turn will help with more effective transfer of load during compression from the matrix to the reinforcement and help eliminate stress buildup, resulting in increased toughness and strength (26, 54). In comparison, smaller microfibers (with similar fiber content of 1:3) due to their short sizes, cannot make a larger connected composite mat resulting in ineffective transfer of load during compression, yielding lower compressive values (FIGS. 3A-3B). Studies using partially dissolved polyphosphazene have reported a similar effect after binding to nano-hydroxyapatite forming stronger reinforced scaffolds (55). The previous silk reinforcement studies using 1-5 micron silk particles obtained through milling has reported compressive values of ~2.8 MPa under hydrated conditions (24, 26), which is about ¼ of the compressive strength measured in the silk microfiber reinforced scaffolds described herein. Accordingly, the role of microfiber size/length on compressive properties of the silk microfiber reinforced scaffold described herein is non-obvious and unexpected. In comparison, control HFIP scaffolds without microfibers, showed lower compressive values of ~85 kPa, related to the presence of intermolecular hydrogen bonds between silk chains in the β-sheets induced due to methanol treatment (24, 26, 56).

When used in lower proportions to the silk matrix (as in 1:1 ratios), silk scaffolds with microfibers of larger size showed contrasting results (FIG. 2B). This is possibly due to uneven packing, where, smaller and medium sized microfibers, due to their greater numbers in comparison to the larger microfibers, distributed better resulting in more even packing and stronger composites (~2-4 MPa) in contrast to larger microfibers (~1 MPa), which can leave gaps (observed during sectioning, images not shown) resulting in lower compressive properties.

The importance of the high compressive data in the 1:3 ratio study group (in the hydrated state) is emphasized when compared with previously reported conventional degradable polymeric biomaterials like collagen, polycaprolactone (PCL), poly-glycolic acid (PLGA), chitosan and gelatin intended for bone tissue engineering. Collagen in pure form is known to have low compressive properties in the hydrated state (2-150 kPa) and even in blends with osteoinductive hydroxyapatite (HA) and bioglass, porous scaffolds have shown low compressive properties in the range of 200 kPA and 2.97 MPa respectively (57, 58). Further using 4.8 wt % chitosan, 2.56 MPa was reached in scaffolds, and in combination with alginate (in equal ratios) there was an increase to 8.1 MPa when tested in the dry state (59). Similarly, PCL/HA and PLGA/β-TCP scaffolds had values of 0.74 MPa and 4.19 MPa, respectively (60, 61), much lower than the values with biodegradable silk microfiber-reinforced scaffolds in the hydrated state.

Further, a possible role of extracellular matrix (ECM) towards mechanical improvements was evaluated using silk-microfiber reinforced scaffolds by culturing and differentiating hMSCs towards bone-like tissue Enhanced biomechanics was observed due to possible deposition of ECM and mineralization as a result of osteogenic differentiation within scaffolds of all ratios and types over time (higher collagen, ALP gene expression) (25, 39. 41). With an increase of ~26%, compressive modulus of scaffolds with medium sized microfibers reached a maximum of ~13 MPa followed by large and smaller sized microfiber scaffolds with enhancement of ~12% (~11 MPa) and ~29% in compressive modulus (~7.5 MPa), respectively (FIG. 2B). However, no statistical difference was observed between compressive values of larger and medium microfiber scaffolds. In the presence of differentiation factors, the hMSCs differentiated towards bone-like cells, as confirmed from higher ALP and gene expression values (FIG. 3A, and FIGS. 5A-5D) (25, 41).

Significant improvements in compressive properties (~13 MPa) of the silk microfiber reinforced scaffolds were observed as compared to that of the existing scaffolds. In some embodiments, the silk microfiber reinforced scaffold can have a compressive strength exceeding values needed for cancellous bone (~10 MPa). In some embodiments, the silk microfiber reinforce scaffold can have a compressive strength comparable to that of native trabecular bone (~100 MPa) (24, 26, 43), e.g., by using these new composite scaffolds as temporary, biodegradable support conduits for native cells to grow and replace with ECM, thus improving biomechanical properties over time. Cellular proliferation, osteogenic potential and in vivo compatibility were evaluated. Seeded cells grew and proliferated with significant expression of collagen (Colα1) within the microfiber reinforced scaffolds, similar to controls (FIGS. 5A-5D). The lower cell proliferation on microfiber scaffolds compared to controls may be due to lower porosity, hindering cell migration (FIG. 3B and FIG. 4) (40). hMSC differentiation towards bone-like cells was observed at an increased rate on the more rigid and rougher microfiber reinforced scaffolds when compared to the controls (FIG. 3A, and FIGS. 5A-5D). Significant increases in levels of OP and BSP were observed for the microfiber reinforced scaffolds as compared to controls, a sign of enhanced osteogenesis (25, 27, 28, 41). Increased roughness and rigidity of scaffolds indicated an enhancement of hMSC differentiation towards bone. A role of matrix stiffness and surface roughness in cell motility and behavior has been reported to influence differentiation (62-64). Particularly, hMSCs differentiating into an osteogenic lineage on stiffer matrices has been reported, including studies on stiffer 3D silk matrices (25, 27, 28, 41, 63-65). Higher OP and BSP transcript levels are indicative of the structure of the mineralized matrix where OP is specifically responsible for cell attachment at bone modeling sites, regulation of crystal formation and growth due to its ability to bind to bind to hydroxyapatite, whereas, BSP enhances nucleation of hydroxyapatite crystals and is a marker for osteogenesis (66-69). Higher levels ALP, a marker for osteoblastic phenotype (41, 63, 64) also showed enhanced differentiation of hMSCs on reinforced scaffolds when compared to the controls (FIGS. 5A-5D).

To assess in vivo inflammatory responses and biocompatibility, these new silk microfiber reinforced scaffolds were implanted subcutaneously in mice. Following 1 week in vivo, minimal inflammatory responses (36, 70) were observed around the control, larger and medium sized microfiber scaffolds (FIG. 6). In comparison, the smaller microfiber reinforced scaffolds showed more immune cells surrounding the implants (FIG. 6). Without wishing to be bound by theory, these differences could be associated with the size of the foreign materials (10-20 μm silk microfibers) inducing greater adhesion and effective phagocytosis by surrounding macrophages compared to larger particles less susceptible to phagocytosis (71). The results presented herein agree with previous reports on less adhesion of immuno-competent cells to de-gummed pure silk fibroin in vitro, as compared to polystyrene and poly(2-hydroxyethyl methacrylate) (70). Further, immune compatibility of pure silk films has been reported in vivo, inducing a lower inflammatory response than collagen films and polylactic acid (PLA) films (36). Similarly, silk non-woven mats implanted subcutaneously in rats induced a weak foreign body response and no fibrosis with little upregulation of inflammatory pathways at the implantation site and no invasion by lymphocytes after six months in vivo (37).

A new method to generate silk microfibers with control of desired lengths is presented herein. As a result, new silk microfiber reinforced 3D scaffolds were fabricated with strong protein-protein interfacial bonding between the microfiber and bulk silk components. These interactions gave rise to enhanced compressive properties aimed towards bone tissue engineering. The developed 3D scaffold systems provided insight on the role of microfiber dimensions on mechanical properties and immune responses. A combination of matrix stiffness and surface roughness favored hMSC differentiation. Further, silk microfiber-protein composite matrices mimicked the mechanical features of native bone and significantly increased osteogenic differentiation of hMSCs when compared to control silk sponges. In some embodiments, the silk microfiber reinforced scaffolds can be tuned for various degradation rates. In some embodiments, the silk microfiber reinforced scaffold can be used for bone formation in vivo.

REFERENCES

1. Drosse I, (2008) Tissue engineering for bone defect healing: an update on a multi-component approach. Injury 39:S9-20.
2. Langer R, Vacanti J P (1993) Tissue Engineering. Science 260:920-926.
3. Marquis M E, et al. (2009) Bone cells biomaterials interactions. Front Biosci 14:1023-1067.
4. Khan Y, Yaszemski M J, Mikos A G, Laurencin C T (2008) Tissue engineering of bone: material and matrix considerations. J Bone Joint Surg Am 90:36-42.
5. Dawson J I, et al. (2008) Development of specific collagen scaffolds to support the osteogenic and chondrogenic differentiation of human bone marrow stromal cells. Biomaterials 29:3105-3116.
6. Pek Y S, Gao S J, Arshad M S M, Leck K J, Ying J Y (2008) Porous collagen apatite nanocomposite foams as bone regeneration scaffolds. Biomaterials 29:4300-4305.
7. Oliveira J M, et al. (2006) Novel hydroxyapatite/chitosan bilayered scaffold for osteochondral tissue engineering applications: Scaffold design and its performance when seeded with goat bone marrow stromal cells. Biomaterials 27:6123-6137.
8. Le Nihouannen D, et al. (2006) Micro-architecture of calcium phosphate granules and fibrin glue composites for bone tissue engineering. Biomaterials 27:2716-2722.
9. Sikavitsas V I, Bancroft G N, Mikos A G (2002) Formation of three-dimensional cell/polymer constructs for bone tissue engineering in a spinner flask and a rotating wall vessel bioreactor. J Biomed Mater Res 62:136-148.
10. Ochi K, et al., (2003) Use of isolated mature osteoblasts in abundance acts as desired-shaped bone regeneration in combination with a modified poly-DL-lactic-co-glycolic acid (PLGA)-collagen sponge. J Cell Physiol 194:45-53.
11. Zhang K, Ma Y, Francis L F (2002) Porous polymer/bioactive glass composites for soft to hard tissue interfaces. J Biomed Mater Res 61:551-563.
12. Hutmacher D W, et al. (2001) Mechanical properties and cell cultural response of polycaprolactone scaffolds designed and fabricated via fused deposition modeling. J Biomed Mater Res 55:203-216.
13. Del Gaudio C, et al. (2006) Assessment of electrospun PCL scaffold for tissue engineering. Int J Artif Organs 29:537-537.
14. Izquierdo R, et al. (2008) Biodegradable PCL scaffolds with an interconnected spherical pore network for tissue engineering. J Biomed Mater Res A 8:25-35.
15. Liao J, Guo X, Nelson D F, Kasper F K, Mikos A G (2010) Modulation of osteogenic properties of biodegradable polymer/extracellular matrix scaffolds generated with a flow perfusion bioreactor. Acta Biomater 6:2386-2393.
16. Xiao Y, Qian H, Young W G, Bartold P M (2003) Tissue engineering for bone regeneration using differentiated alveolar bone cells in collagen scaffolds. Tissue Eng 9:1167-1177.
17. Yang X B B, Bhatnagar R S, Li S, Oreffo R O C (2004) Biomimetic collagen scaffolds for human bone cell growth and differentiation. Tissue Eng 10:1148-1159.
18. Hodgskinson R, Currey J D (1992) Young modulus. Density and material properties in cancellous bone over a large density range. J Mater Sci Mater M 3:377-381.
19. Yaszemski M J, Payne R G, Hayes W C, Langer R, Mikos A G (1996) Evolution of bone transplantation: Molecular, cellular and tissue strategies to engineer human bone. Biomaterials 17:175-185.
20. Khan Y M, Katti D S, Laurencin C T (2004) Novel polymer-synthesized ceramic composite-based system for bone repair: an in vitro evaluation. J Biomed Mater Res A 69:728-737.
21. Thein-Han W W, Shah J, Misra R D K (2009) Superior in vitro biological response and mechanical properties of an implantable nanostructured biomaterial: nano hydroxyapatite-silicone rubber composite. Acta Biomater 5:2668-2679.
22. Wei G B, Ma P X (2004) Structure and properties of nano-hydroxyapatite/polymer composite scaffolds for bone tissue engineering. Biomaterials 25:4749-4757.
23. Zhang Y, Wu C, Friis T, Xiao Y (2010) The osteogenic properties of CaP/silk composite scaffolds. Biomaterials 31:2848-2856.
24. Gil E S, et al. (2011) Mechanical improvements to reinforced porous silk scaffolds. J Biomed Mater Res Part A 99:16-28.
25. Rockwood D N, et al. (2011) Ingrowth of human mesenchymal stem cells into porous silk particle reinforced silk composite scaffolds: An in vitro study. Acta Biomaterialia 7:144-151.
26. Rangam R, et al. (2010) Reinforced silk scaffolds with silk particles. Macromol Biosci 10:599-611.
27. Mandal B B, Kundu S C (2009a) Non-mulberry silk gland fibroin 3D scaffold for enhanced differentiation of human mesenchymal stem cells into osteocytes. Acta Biomaterialia 5:2579-2590.
28. Mandal B B, Kundu S C (2009b) Osteogenic and adipogenic differentiation of rat bone marrow cells on 28. mulberry and non-mulberry silk gland fibroin 3D scaffolds. Biomaterials 30:5019-5030.
29. Salgado A J, Coutinho O P, Reis R L (2004) Bone tissue engineering: State of the art and future trends. Macromol Biosci 4:743-765.
30. Zhou Y F, et al. (2007) Combined marrow stromal cell-sheet techniques and high strength biodegradable composite scaffolds for engineered functional bone grafts. Biomaterials 28:814-824.
31. Leong K F, Cheah C M, Chua C K (2003) Solid freeform fabrication of three-dimensional scaffolds for engineering replacement tissues and organs. Biomaterials 24:2363-2378.
32. Vitale-Brovarone C, Baino F, Verne E (2009) High strength bioactive glass-ceramic scaffolds for bone regeneration. J Mater Sci Mater M 20:643-653.
33. Vepari C, Kaplan D L (2007) Silk as a biomaterial. Prog Polym Sci 32:991-1007.
34. Wang Y, Kim H J, Vunjak-Novakovic G, Kaplan D L (2006) Stem cell-based tissue engineering with silk biomaterials. Biomaterials 27:6064-6082.
35. Altman G H, et al. (2002) Silk matrix for tissue engineered anterior cruciate ligaments. Biomaterials 23:4131-4141.
36. Meinel L, et al. (2005) The inflammatory responses to silk films in vitro and in vivo. Biomaterials 26:147-155.
37. Dal Pra I, Freddi G, Minic J, Chiarini A, Armato U (2005) De novo engineering of reticular connective tissue in vivo by silk fibroin nonwoven materials. Biomaterials 26:1987-1999.
38. Wang Y, et al. (2008) In vivo degradation of three-dimensional silk fibroin scaffolds. Biomaterials 29:3415-3428.
39. Mandal B B, Park S H, Gil E S, Kaplan D L (2011) Multilayered silk scaffolds for meniscus tissue engineering. Biomaterials 32:639-651.
40. Mandal B B, Kundu S C (2009c) Cell proliferation and migration in 3D silk fibroin scaffolds. Biomaterials 30:2956-2965.
41. Park S H, et al. (2010) Relationship between degradability of silk scaffolds and osteogenesis. Biomaterials 31:6162-6172.
42. Kim H J, et al. (2007) Bone regeneration on macroporous aqueous-derived silk 3-D scaffolds. Macromol Biosci 7:643-655.
43. Rangam R, Wang L, Wang X (2008) Ultrafine silk powder preparation through rotary and ball milling. Power Technology 185:87-95.
44. Rangam R, Wang L, Kanwar J, Wang X (2009) Fabrication of ultrafine powder from eri silk through attritor and jet milling. Powder Technology 191:155-163.
45. Shao Z Z, Vollrath F (2002) The surprising strength of silkworm silk. Nature 418:741.
46. Coleman D, Howitt F O, (1947) Studies on Silk Proteins. I. The Properties and Constitution of Fibroin. The Conversion of Fibroin into a Water-Soluble Form and Its Bearing on the Phenomenon of Denaturation. PRS London. Series A, Math Phy Sci 90:145-169.
47. Desai A V, Hague M A (2005) Mechanics of the interface for carbon nanotube-polymer composites. Thin-Walled Struct 43:1787-1803.
48. Kim H J, Kim U J, Vunjak-Novakovic G, Min B H, Kaplan D L (2005) Influence of macroporous protein scaffolds on bone tissue engineering from bone marrow stem cells. Biomaterials 26:4442-4452.
49. Hodgskinson R, Currey J D (1992) Young modulus, Density and material properties in cancellous bone over a large density range. J Mater Sci-Mater M 3:377-381.
50. Banse X, et al. (2001) Inhomogeneity of human vertebral cancellous bone: Systematic density and structure patterns inside the vertebral body. Bone 28:563-571.
51. Muller R, et al. (1998) Morphometric analysis of human bone biopsies: A quantitative structural comparison of histological sections and micro-computed tomography. Bone 23:59-66.
52. Ramakrishna S, Mayer J, Wintermantel E, Leong K W (2001) Biomedical applications of polymer-composite materials: a review. Compos Sci Technol 61:1189-1224.
53. Lau K T, Gu C, Hui D (2006) A critical review on nanotube and nanotube/nanoclay related polymer composite materials. Compos Part B Eng 37:425-436.
54. M. Wang (2003) Developing bioactive composite materials for tissue replacement. Biomaterials 24:2133-2151.
55. Nukavarapu S P, et al. (2008) Polyphosphazene/nano-hydroxyapatite composite microsphere scaffolds for bone tissue engineering. Biomacromolecules 9:1818-1825.
56. Nazarov R, Jin H J, Kaplan D L (2004) Porous 3-D scaffolds from regenerated silk fibroin. Biomacromolecules 5:718-726.
57. Kane R J, Roeder R K (2011) Effects of hydroxyapatite reinforcement on the architecture and mechanical properties of freeze-dried collagen scaffolds. J Mech Behav Biomed Mater (doi:10.1016/j.jmbbm.2011.09.010)
58. Caixia Xu, et al. (2011) Biocompatibility and osteogenesis of biomimetic Bioglass-Collagen-Phosphatidylserine composite scaffolds for bone tissue engineering. Biomaterials 32:1051-1058.
59. Zhensheng Li, et al. (2005) Chitosan-alginate hybrid scaffolds for bone tissue engineering. Biomaterials 26:3919-3928.
60. Kang Y, et al. (2011) Enhanced mechanical performance and biological evaluation of a PLGA coated b-TCP composite scaffold for load-bearing applications. Eur Poly J 47:1569-1577.
61. Wang Y, Dai J, Zhang Q, Xiao Y, Lang M (2010) Improved mechanical properties of hydroxyapatite/poly (caprolactone) scaffolds by surface modification of hydroxyapatite. App Surf Sci 256:6107-6112.
62. Discher D E, Janmey P, Wang Y L (2005) Tissue cells feel and respond to the stiffness of their substrate. Science 310:1139-1143.
63. Balloni S, et al. (2009) Effects of titanium surface roughness on mesenchymal stem cell commitment and differentiation signaling. Int J Oral Maxillofac Implants 24:627-635.
64. Hu X, et al. (2011) The influence of elasticity and surface roughness on myogenic and osteogenic-differentiation of cells on silk elastin biomaterials. Biomaterials 32:8979-8989.
65. Engler A J, Sen S, Sweeney H L, Discher D E (2006) Matrix elasticity directs stem cell lineage specification. Cell 126:677-689.
66. Kasugai S, Nagata T, Sodek J (1992) Temporal studies on the tissue compartmentalization of bonesialoprotein (BSP), Osteopontin (OPN), and SPARC protein during bone formation in vitro. J Cell Physiol 152:467-477.
67. Alford A I, Hankenson K D (2006) Matricellular proteins: extracellular modulators of bone development, remodeling, and regeneration. Bone 38:749-757.

68. Giachelli C M, Steitz S (2000) Osteopontin: a versatile regulator of inflammation and biomineralization. Matrix Biol 19:615-622.
69. Ganss B, Kim R H, Sodek J (1999) Bone sialo protein. Crit Rev Oral Biol Med 10:79-98.
70. Santin M, Motta A, Freddi G, Cannas M (1999) In vitro evaluation of the inflammatory potential of the silk fibroin. J Biomed Mater Res 46:382-389.
71. Jutras I, Desjardins M (2005) Phagocytosis: at the crossroads of innate and adaptive immunity. Ann rev cell dev biol 21:511-527.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method comprising
   contacting a plurality of degummed silk fibers with an alkaline solution under conditions in which the degummed silk fibers undergo alkaline hydrolysis to provide silk microfibers having an aspect ratio of length to width of at least 2:1, and
   reinforcing a matrix material by associating at least some of the silk microfibers with the matrix material to form a composite material.

2. The method of claim 1, wherein the length of the silk microfibers ranges from about 1 μm to about 2 mm.

3. The method of claim 1, wherein the alkaline solution comprises sodium hydroxide, potassium hydroxide, lithium hydroxide, rubidium hydroxide, cesium hydroxide, calcium hydroxide, strontium hydroxide, barium hydroxide, or any combinations thereof.

4. The method of claim 1, wherein the alkaline solution has a concentration of about 0.1 M to about 30 M.

5. The method of claim 1, wherein the contacting is maintained for a duration ranging from about 5 seconds to about 5 hours.

6. The method of claim 1, wherein the contacting is performed at about 4° C. to about 100° C.

7. The method of claim 1, further comprising neutralizing the mixture comprising one or more silk microfibers and the alkaline solution.

8. The method of claim 1, further comprising annealing the silk microfibers.

9. The method of claim 1, further comprising separating a subset of the silk microfibers of a desired length from the plurality of silk microfibers.

10. The method of claim 1, wherein the matrix material is polymeric material, ceramic material or combination thereof.

11. The method of claim 10, wherein the polymeric material is selected from the group consisting of polyethylene oxide, polyethylene glycol, collagen, fibronectin, keratin, silk, silk fibroin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, poly(lactide-co-glycolide) (PLA-PLA-PGA), polymethylmethacrylate, polyanhydride, polyorthoester, polycaprolactone, polyfumarate, chitosan, alginate, and any combination thereof.

12. The method of claim 10, wherein the ceramic material is selected from the group consisting of calcium phosphate, calcium sulfate, hydroxyapatite, bioactive glass, and any combination thereof.

13. The method of claim 1, wherein the composite material is porous.

14. The method of claim 1, wherein the composite material is non-porous.

* * * * *